US010508152B2

(12) United States Patent
Wang et al.

(10) Patent No.: US 10,508,152 B2
(45) Date of Patent: *Dec. 17, 2019

(54) SMART CAR DEVICES, DE CAR POLYPEPTIDES, SIDE CARS AND USES THEREOF

(71) Applicant: Chimera Bioengineering, Inc., Menlo Park, CA (US)

(72) Inventors: Benjamin Wang, Menlo Park, CA (US); Gusti Zeiner, Pacifica, CA (US)

(73) Assignee: Chimera Bioengineering, Inc., Menlo Park, CA (US)

( * ) Notice: Subject to any disclaimer, the term of this patent is extended or adjusted under 35 U.S.C. 154(b) by 162 days.

This patent is subject to a terminal disclaimer.

(21) Appl. No.: 15/707,242

(22) Filed: Sep. 18, 2017

(65) Prior Publication Data

US 2018/0030143 A1 Feb. 1, 2018

Related U.S. Application Data

(63) Continuation of application No. 15/070,352, filed on Mar. 15, 2016, now Pat. No. 9,777,064.

(60) Provisional application No. 62/134,143, filed on Mar. 17, 2015, provisional application No. 62/152,727, filed on Apr. 24, 2015, provisional application No. 62/183,595, filed on Jun. 23, 2015, provisional application No. 62/276,449, filed on Jan. 8, 2016.

(51) Int. Cl.
| | | |
|---|---|---|
| *C07K 16/28* | (2006.01) | |
| *C12N 5/0783* | (2010.01) | |
| *A61K 39/00* | (2006.01) | |

(52) U.S. Cl.
CPC ........ *C07K 16/2887* (2013.01); *C12N 5/0636* (2013.01); *A61K 2039/505* (2013.01); *C07K 2319/03* (2013.01); *C07K 2319/74* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 2009/0048191 A1 | 2/2009 | Rakoczy et al. | |
| 2010/0316609 A1 | 12/2010 | Dewhurst et al. | |
| 2011/0003385 A1 | 1/2011 | Crabtree et al. | |
| 2013/0245096 A1 | 9/2013 | Abitbol | |
| 2014/0120622 A1* | 5/2014 | Gregory | A61K 35/26 435/462 |
| 2014/0242701 A1 | 8/2014 | Shiku et al. | |
| 2014/0271583 A1 | 9/2014 | Allen-Hoffmann et al. | |
| 2014/0286987 A1 | 9/2014 | Spencer et al. | |
| 2014/0349402 A1 | 11/2014 | Cooper et al. | |
| 2015/0307564 A1 | 10/2015 | Young et al. | |

FOREIGN PATENT DOCUMENTS

| | | |
|---|---|---|
| WO | WO 2015092440 | 6/2015 |
| WO | WO 2015/123642 | 8/2015 |
| WO | WO 2015123527 | 8/2015 |
| WO | WO 2015123642 | 8/2015 |
| WO | WO 2015140268 | 9/2015 |
| WO | WO 2015142661 | 9/2015 |
| WO | WO 2015142675 | 9/2015 |
| WO | WO 2015193406 | 12/2015 |
| WO | WO 2016028896 | 2/2016 |
| WO | WO 2016126608 | 8/2016 |

OTHER PUBLICATIONS

Adusumilli et al., Regional Delivery of Mesothelin-Targeted CAR T-cell Therapy Generates Potent . . . Tumor Immunity, Nov. 2014, Sci. Transl. Med. 6:261ra151.
Aranda et al., Adoptive Cell Transfer for Anticancer Immunotherapy, Apr. 2015, OncoImmunol. 3:5, e28344.
Auslander, et al., From Gene Switches to Mammalian Designer Cells: Present and Future Prospects, Mar. 2013, Trends Biotechnol. 31:155-168.
Baker et al., Structural and Dynamic Control of T-cell Receptor Specificity, Cross-Reactivity, and Binding Mechanism, 2012, Immunol. Rev. 250:10-31.
Beilstein, et al., Conditional Control of Mammalian Gene Expression by Tetracycline-Dependent Hammerhead Ribozymes, Sep. 2014, Synth. Biol. 4:526-534.
Berens, et al., RNA Aptamers as Genetic Control Devices: The Potential of Riboswitches as Synthetic Elements for Regulating Gene Expression, 2015, Biotechnol. 10:246-257.
Bonifant, et al., Toxicity and Management in CAR T-cell Therapy, 2016, Oncolytics 3:16011.
Bray, et al., On-Site CAR Parking, 2015, Sci. Transl. Med. 7:275ra22.
Brayer et al., Developing Strategies in the Immunotherapy of Leukemias, Jan. 2013, Cancer Control 20:49-59.
Brentjens, et al., Adoptive Therapy of Cancer with T cells Genetically Targeted to Tumor Associated Antigens Through . . . , May 2011, Am Soc Gene Cell Therap., presentation.
Brudno et al., Allogenic T Cells That Express and Anti-CD19 Chimeric Antigen Receptor Induce Remissions of B-cell . . . , 2016, Am Soc Clin Oncol 34.

(Continued)

*Primary Examiner* — Mindy G Brown

(57) ABSTRACT

The present invention relates generally to the field of RNA Control Devices and/or destabilizing elements (DE) combined with Chimeric Antigen Receptors (CARs) in eukaryotic cells. The present invention also relates to split CARs (Side-CARs) in eukaryotic cells. More specifically, the present invention relates to DEs, RNA Control Devices, and/or side-CARs combined with Chimeric Antigen Receptors to make small molecule actuatable CAR polypeptides. The present invention also relates to DE-CARs, Smart CARs (Smart=small molecule actuatable RNA trigger), Smart-DE-CARs, and/or Side-CARs for use in the treatment of disease.

20 Claims, 3 Drawing Sheets

Specification includes a Sequence Listing.

(56) References Cited

OTHER PUBLICATIONS

Buckley et al., Update on Antigen-Specific Immunotherapy of Acute Myeloid Leukemia, 2015, Curr. Hematol. Malig. Rep. 10:65-75.
Budde et al., Combining a CD20 Chimeric Antigen Receptor and an Inducible Caspace 9 Suicide Switch to Improve the Efficacy . . . , Dec. 2013, PLoS ONE 8:e82742.
Cantelmo, et al., Inhibition of the Glycolytic Activator PFKFB3 in Endothelium Induces Tumor Vessel Normalization . . . , Dec. 2016, Cancer Cell 30:968-985.
Caruso et al., Tuning Sensitivity of CAR to EGFR Density Limits Recognition of Normal Tissue While Maintaining . . . , 2015, Cancer Res. 75:3505-3518.
Chakravarti et al., Synthetic Biology in Cell-Based Cancer Immunotherapy, 2015, Trends Biotechnol. 33:449-461.
Chang et al., Posttranscriptional Control of T Cell Effector Function by Aerobic Glycolysis, Jun. 2013, Cell 153:1239-1251.
Chang et al., Identification and Selective Expansion of Functionally Superior T cells Expressing Chimeric Antigen Receptors, 2015, J. Transl. Med. 13:161.
Cheadle et al., CAR T cells: Driving the Road from the Laboratory to the Clinic, 2013, Immunol. Rev. 257:91-106.
Chen et al., Genetic Control of Mammalian T-cell Proliferation with Synthetic RNA Regulatory Systems, 2010, Proc. Natl Acad. Sci. 107:8531-8536.
Chen et al., Efficient Gene Editing in Primary Human T cells, Nov. 2015, Trends Immunol. 36:667-669.
Cooper et al., Moving from Tinkering in the Garage to Assembly Line Production: the Manufacture of Genetically Modified T cells . . . , 2015, Cancer Gene Therap. 22:64-66.
Darcy et al., Adoptive Immnotherapy: a New Era for the Treatment of Cancer, 2015, Immunotherap. 7:469-471.
Davila et al., Efficacy and Toxicity Management of 19-28z CAR T cell Therapy in B cell Acute Lymphoblastic Leukemia, Feb. 2014, Sci Transl Med 6:224ra25.
Di Stasi et al., Inducible Apoptosis as a Safety Switch for Adoptive Cell Therapy, 2011, N. Engl. J. Med. 265:1673-83.
Dotti et al., Design and Development of Therapies Using Chimeric Antigen Receptor-Expressing T cells, Jan. 2014, Immunol. Rev. 257:107-126.
Elert et al., Calling Cells to Arms, Dec. 2013, Nature 504:S2-S3.
Elfakess et al., Unique Translation Initiation of mRNAs-Containing TISU Element, Jun. 2011, Nucl. Acids. Res. 39:7598-7609.
Ellebrecht et al., Reengineering Chimeric Antigen Receptor T cells for Targeted Therapy of Autoimmune Disease, Jul. 2016, Science 353:179-184.
Farajnia et al., Development Trends for Generation of Single-Chain Antibody Fragments, Aug. 2014, Immunopharmacol. Immunotoxicol. 36:297-308.
Federov et al., PD-1 and CTLA-4 Based Inhibitory Chimeric Antigen Receptors (iCARs) Divert Off-Target Immunotherapy . . . , Dec. 2013, Sci. Transl. Med. 5:215ra172.
Festuccia et al., Allogenic Stem Cell Transplantation in Multiple Myeloma: Immunotherapy and New Drugs, Jun. 2015, Expert Opin. Biol. Therapy 15:857-872.
Garber et al., Adoptive T-cell Therapy for Leukemia, 2014, Molc. Cell. Therap. 2:25.
Garcia-Sanz et al., Translational Control: a General Mechanism for Gene Regulation During T cell Activation, 1998, FASEB J. 12:299-306.
Ghorashian et al., CD19 Chimeric Antigen Receptor T cell Therapy for Haematological Malignancies, Mar. 2015, Brit, J. Haematol. 169:463-478.
Grada et al., TanCAR: A Novel Bispecific Chimeric Antigen Receptor for Cancer Immunotherapy, 2013, Molc. Therap. Nucl. Acids 2:e105.
Hamilton et al., Delineation of a Novel Pathway that Regulates CD154 (CD40 Ligand) Expression, 2003, Molc. Cell. Biol. 23:510-525.
Hjelm et al., Mifepristone-Inducible Transgene Expression in Neural Progenitor Cells in vitro and in vivo, 2016, Gene Therap. 23:424-437.
Horton et al., Recent Advances in Acute Myeloid Leukemia Stem Cell Biology, 2012, Haematolog. 97:966-974.
Huang et al., Driving an Improved CAR for Cancer Immunotherpy, 2016, J. Clin. Invest. 126:2795-2798.
Hudecek et al., The Nonsignaling Extracellular Spacer Domain of Chimeric Antigen Receptors is Decisive for In Vivo . . . , Sep. 2014, Cancer Immunol. Res. 3:125-135.
Hurton et al., Tethered IL-15 Augments Antitumor Activity and Promotes a Stem-Cell Memory Subset in Tumor-Specific T cells, Nov. 2016, Proc. Natl Acad Sci 113:E7788-E7797.
Hussaini et al., Targeting CD123 in AML Using a T-cell Directed Dual-Affinity Re-Targeting (DART) Platform, Nov. 2015, Blood 127:122-131.
Iwamoto et al., A General Chemical Method to Regulate Protein Stability in the Mammalian Central Nervous System, 2010, Chem Biol 17:981-988.
Jensen et al., Enhancing the IQ of CAR Modified T Cells, 2015, Powerpoint Slides.
Jensen et al., Mathematical Modeling of Chimeric TCR Triggering Predicts the Magnitude of target Lysis and its Impairment by TCR . . . , 2010, J. Immunol. 184:4284-4294.
Jensen et al., Design and Implementation of Adoptive Therapy with Chimeric Antigen Receptor-Modified T cells, 2014, Immunol. Rev. 257:127-144.
Jensen, Synthetic Immunobiology Boosts the IQ of T cells, Oct. 2015, Science 350:514-515.
Jensen et al., Designing Chimeric Antigen Receptors to Effectively and Safely Target Tumors, 2015, Curr. Opin. Immunol. 33:9-15.
Johnson et al., Rational Development and Characterization of Humanized Anti-EGFR Variant III Chimeric Antigen Receptor . . . , Feb. 2015, Sci. Transl. Med. 7:275ra22.
Juillerat et al., Design of Chimeric Antigen Receptors with Intergrated Controllable Transient Functions, 2016, Sci. Rep. 6:18950.
June, Drugging the Undruggable Ras—Immunotherapy to the Rescue? 2016, N. Eng. J. Med. 375:2286-2289.
Kakarla et al., CAR T cells for Solid Tumors: Armed and Ready to Go? Mar.-Apr. 2014, Cancer J. 20:151-155.
Kalos et al., Adoptive T cell Transfer for Cancer Immunotherapy in the Era of Synthetic Biology, Jul. 2013, Immunity 39:49-60.
Kawalekar et al., Distinct Signaling of Coreceptors Regulates Specific Metabolism Pathways and Impacts Memory Development . . . , 2016, Immunity 44:380-390.
Kebriaei et al., Future of Therapy in Acute Lymphoblastic Leukemia (ALL)—Potential Role of Immune-Based Therapies, 2015, Curr. Hematol. Malig. Rep. 10:76-85.
Kebriaei et al., Phase I Trials Using Sleeping Beuaty to Generate CD19-Specific CAR T cells, 2016, J. Clin. Invest. 126:3363-3376.
Kershaw et al., Clinical Application of Genetically Modified T cells in Cancer Therapy, May 2014, Clin. Transl. Immunol. 3:e16.
Kim et al., Highly Efficient RNA-Guided Genome Editing in Human Cells via Delivery of Purified Cas9 Ribonucleoproteins, Jun. 2014, Gen. Res. 24:1012-1019.
Kis et al., Mammalian Synthetic Biology: Emerging Medical Applications, Mar. 2015, J. R. Soc. Interface 12:20141000.
Kochenderfer et al., Chemotherapy-Refractory Diffuse Large B-cell Lymphoma and Indolent B-cell Malignancies can be Effectively . . . , Aug. 2014, J. CLin. Oncol. 33:540-549.
Ledford, T-cell Therapy Extends Cancer Survival to Years, Dec. 2015, Nature 516:156.
Liang et al., Engineering Biological Systems with Synthetic RNA Molecules, 2011, Molc. Cell 43:915-926.
Lynn et al., Targeting of Folate Receptor-beta on Acute Myeloid Leukemia Blasts with Chimeric Antigen Receptor-Expressing T cells, May 2015, Blood 125:3466-3476.
Lindsten et al., Regulation of Lymphokine Messenger RNA Stability by a Surface-Mediated T Cell Activation Pathway, 1989, Science 244:339-343.
Liu et al., Affinity Tuned ErbB2 or EGFR Chimeric Antigen Receptor T Cells Exhibit an Increased Therapeutic Index Against Tumors in Mice, Sep. 2015, Cancer Res. 75:3596-3607.

(56) References Cited

OTHER PUBLICATIONS

Long et al., 4-1BB Cotimulation Ameliorates T cell Exhaustion Induced by Tonic Signaling of Chimeric Antigen Receptors, Jun. 2015, Nat Med 21:581-590.
Marcus et al., Allogenic Chimeric Antigen Receptor-Modified Cells for Adoptive Cell Therapy of Cancer, Mar. 2014, Expert Opin Biol Therap 14:947-954.
Mardiros et al., T cells Expressing CD123-Specific Chimeric Antigen Receptors Exhibit Specific Cytolytic Effector Functions . . . , Sep. 2013, Blood 122:3138-3148.
Maude et al., Chimeric Antigen Receptor T cells for Sustained Remissions in Leukemia, Mar. 2014, N. Eng. J. Med. 371:1507-1517.
Maus et al., Antibody-Modified T cells: CARs Take the Front Seat for Hematologic Malignancies, Apr. 2014, Blood 123:2625-2635.
Mayer, Nucleic Acid Aptamers: Selection, Characterization and Application, 2016, Humana Press, Springer Science.
Morgan et al., Case Report of a Serious Adverse Event Following the Administration of T cells Transduced with a Chimeric Antigen Receptor . . . , 2010, Molc Therap 18:843-851.
Nagy et al., Glyceraldehyde-3-phosphate Dehydrogenase Selectively Binds AU-Rich RNA in the NAD+-Binding Region, 1995, J Biol Chem 270:2755-2763.
Neeson, Lewis-Y Chimeric Antigen Receptor T cells Traffic and Persist in the Bone Marrow of Patients with Lewis-Y Positive AML, undated, Powerpoint SLides.
Nelson et al., Novel Immunotherapies for Hematologic Malignancies, Jan. 2015, Immunol. Rev. 263:90-105.
Newick et al., CAR T cell Therapy for Solid Tumors, Jul. 2016, Ann. Rev. Med. 68:3.1-3.14.
Norelli et al., Clinical Pharmacology of CAR-T cells: Linking Cellular Pharmacodynamics to Pharmacokinetics and Antitumor Effects, 2016, Biochim Biophys Acta 1865:90-100.
Okoye et al., The Protein LEM Promotes CD8+ T cell Immunity Through Effects on Mitochondrial Respiration, May 2015, Science 348:995-1001.
Paszkiewicz et al., Targeted Antibody-Mediated Depletion of Murine CD19 CAR T cells Permanently Reverses B cell Aplasia, 2016, J Clin Ivest 126:4262-4272.
Perales-Puchalt et al., Follicle-Stimulating Hormone Receptor is Expressed by Most Ovarian Cancer Subtypes and is a Safe . . . , 2016, Clin. Cancer Res.
Pizzitola et al., Chimeric Antigen Receptors Against CD33/CD123 Antigens Efficiently Target Primary Acute Myeloid Leukemia Cells in vivo, Aug. 2014, Leukemia 28:1596-1605.
Poirot et al., Multiplex Genome-Edited T-cell Manufacturing Platform for "Off-the-Shelf" Adoptive T-cell Immunotherapies, 2015, Cancer Res 75:3853-3864.
Posey et al., Engineered CAR T cells Targeting the Cancer-Associated Tn-Glycoform of the Membrane Mucin MUC1 Control Adenocarcinoma, 2016, Immunity 44:1444-1454.
Qin et al., Systematic Comparison of Constitutive Promoters and the Doxycycline-Inducible Promoter, 2010, PLoS ONE 5:e10611.
Rakhit et al., Chemical Biology Strategies for Posttranslational Control of Protein Function, Sep. 2014, Chem Biol 21:1238-1252.
Reddy, Changing Landscape of Immuno-Oncology: CAR-T Therapy and PD1/PDL1 Blockade, 2016, Boston University Theses.
Renert, Novel Immunotherapeutic Approaches to the Treatment of Cancer: Drug Development and Clinical Application, 2016, Springer International Publishing.
Rodgers et al., Switch-Mediated Activation and Retargeting of CAR-T cells for B-cell Malignancies, 2016, Proc Natl Acad Sci 113:E459-E468.
Rosenberg, Cell Transfer Immunotherapy for Metastataic Solid Cancer—What Clinicians Need to Know, 2011, Nat Rev Clin Oncol 8:577-585.
Rosenberg et al., Adoptive Cell Transfer as Personalized Immunotherapy for Human Cancer, Apr. 2015, Science 348:62-68.
Roybal et al., Precision Tumor Recognition by T cells with Combinatorial Antigen-Sensing Circuits, 2016, Cell 164:770-779.
Roybal et al., Engineering T cells with Customized Therapeutic Response Programs Using Synthetic Notch Receptors, 2016, Cell 167:1-14.
Sadelain et al., Safe Harbours for the Integration of New DNA in the Human Genome, 2012, Nat. Rev. 12:51-58.
Sandberg et al., In Cancer Immunotherapy Legal Battle, It's Now *Juno v. Novartis*, Feb. 2014, Pharma MedTech Bus Intell. 2014900027.
Shi et al., Chimeric Antigen Receptor for Adoptive Immunotherapy of Cancer: Latest Research and Future Prospects, Sep. 2014, Molc Cancer 13:219.
Sommermeyer et al., Chimeric Antigen Receptor-Modified T cells Derived from Defined CD8+ and CD4+ Subsets Confer Superior Antitumor . . . , Feb. 2016 Leukemia 30:492-500.
Srivastava et al., Engineering CAR-T cells: Design Concepts, Aug. 2015, Trends Immunol 36:494-502.
Sun et al., The Quest for Spatio-Temporal Control of CAR T cells, Dec. 2015, Cell Res. 25:1281-1282.
Tettamanti et al., CD123 AML Targeting by Chimeric Antigen Receptors: A Novel Magic Bullet for AML Therapeutics? May 2014, Oncolimmunol 3:e28835.
Till et al., Adoptive Immunotherapy for Idolent Non-Hodgkin Lymphoma and Mantle Cell Lymphoma Using Genetically Modified . . . , 2008, Blood 112:2261-2271.
Turatti et al., Redirected Activity of Human Antitumor Chimeric Immune Receptors is Governed by Antigen and Receptor Expression Levels . . . , 2007, J Immunotherap 30:684-693.
Turtle et al., CD19 CAR-T cells of Defined CD4+:CD8+ Composition in Adult B cell ALL Patients, 2016, J Clin Ivest 126:2123-2138.
Turtle et al., Immunotherapy of Non-Hodgkin's Lymphoma with a Defined Ratio of CD8+ and CD4+ CD19-Specific Chimeric Antigen Receptor . . . , 2016, Sci Transl Med 8:355ra116.
Vanderlugt et al., Epitope Spreading in Immune-Mediated Diseases: Implications for Immunotherapy, 2002, Nat Rev 2:85-95.
Vigano et al., Functional Avidity: a Measure to Predict the Efficacy of Effector T cells? 2012, Clin Develop Immunol 2012:153863.
Wang et al., ZAP-70: An Essential Kinase in T-cell Signaling, 2010, Cold Spring Barb Perspect Biol 2:a002279.
Wang et al., One-Step Generation of Mice Carrying Mutations in Multiple Genes by CRISPR/Cas-Mediated Genome Engineering, 2013, Cell 153:910-918.
Wang et al., Manufacture of tumor- and virus-specific T lymphocytes for adoptive cell therapies, Feb. 2015, Cancer Gene Therapy 22:85-94.
Watanabe et al., Target Antigen Density Governs the Efficacy of Anti-CD20-CD28-CD3 Zeta Chimeric Antigen Receptor-Modified . . . , Dec. 2014, J Immunol 194:911-920.
Weigand et al., Tetracycline Aptamer-Controlled Regulation of Pre-mRNA Splicing in Yeast, 2007, Nucl Acids Res 35:4179-4185.
Win et al., A Modular and Extensible RNA-Based Gene-Regulatory Platform for Engineering Cellular Function, 2007, Proc Natl Acad Sci 104:14283-14288.
Win et al., Frameworks for Programming Biological Function Through RNA Parts and Devices, 2009, Chem Biol 16:298-310.
Wu et al., Remote Control of Therapeutic T cells Through a Small Molecule-Gated Chimeric Receptor, Sep. 2015, Science 350:aab4077.
Xie et al., Mammalian Designer Cells: Engineering Principles and Biomedical Applications, Jul. 2015, Biotechnol J 10:1005-1018.
Xie et al., Synthetic Biology—Application-Oriented Cell Engineering, 2016, Curr. Opin. Biotechnol. 40:139-148.
Ye et al., Synthetic Mammalian Gene Circuits for Biomedical Applications, 2013, Curr. Opin. Chem Biol 17:910-917.
Zhao et al., Structural Design of Engineered Costimulation Determines Tumor Rejection Kinetics and Persistence of CAR T cells, Oct. 2015, Cancer Cell 28:415-428.
Zheng et al., Protein L: A Novel Reagent for the Detection of Chimeric Antigen Receptor (CAR) Expression by Flow Cytometry, 2012, J Transl Med 10:29.
Muti, ASH Conference Review, 2014.
Zhong et al., Rational Design of Aptazyme Riboswitches for Efficient Control of Gene Expression in Mammalian Cells, Nov. 2016, eLife 5:e18858.

(56) References Cited

OTHER PUBLICATIONS

Auslander et al., A ligand-dependent hammerhead ribozyme switch for controlling mammalian gene expression, Molc. Biosys. vol. 6, pp. 807-814 (2010).

Win et al., A modular and estensible RNA-based gene-regulatory platform for engineering cellular function, Proc. Natl Acad. Sci. vol. 104, pp. 14283-14286 (2007).

Jensen et al., Design and implementation of adoptive therapy with chimeric antigen receptor-modified T-cells, 2013, Immunol. Rev. vol. 257, pp. 127-144.

Kloss et al., Combinatorial antigen recognition with balanced signaling promotes selective tumor eradication by engineered T-cells, 2013, Nature Biotechnol. vol. 31, pp. 71-75.

Lienert et al., Synthetic biology in mammalian cells: Next generation research tools and therapeutics, 2014, Nat Rev Molc Cell Biol vol. 15, pp. 95-107.

Iwamoto et al., A general chemical method to regulate protein stability in the mammalian nervous system, 2010, Chem & Biol vol. 17, pp. 981-988.

Rakhit et al, Evaluation of FKBP and DHFR based destabilizing domains in *Saccharomyces cerivisiae*, 2011, Bioorg & Med Chem Lett vol. 21, pp. 4965-4968.

Jena et al., Redirecting T-cell specificity by introducing a tumor-specific chimeric antigen receptor, 2010, Blood vol. 116, pp. 1035-1044.

Nielsen et al., Split-receptors in the tachykinin neurokinin-1 system, 1998, Eur. J. Biochem. vol. 251, pp. 217-226.

Christopherson et al., Classfication of AML using a monoclonal antibody microarray, 2006, Meth in Mocl Med vol. 125, pp. 241-251.

Kondo et al., Binding of glyceraldehyde-3-phoisphate dehydrogenase to the cis-acting element of structure-anchored . . . , 2011, Biochem Biophys Res Comm vol. 405, pp. 382-387.

Palmer et al, Glucose metabolism regulates T cell activation, differentiation, and functions, 2015, Frontiers Immunol vol. 5, pp. 1-6.

Kloss et al, Combinatorial antigen recognition with balanced signalling promotes selective tumor eradication . . . , 2013, Nat Biotechnol vol. 31, pp. 71-75.

\* cited by examiner

SEQUENCE LISTING

```
<160> NUMBER OF SEQ ID NOS: 53

<210> SEQ ID NO 1
<211> LENGTH: 107
<212> TYPE: PRT
<213> ORGANISM: Artificial Sequence
<220> FEATURE:
<223> OTHER INFORMATION: FKBP peptide

<400> SEQUENCE: 1

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
        50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 2
<211> LENGTH: 107
<212> TYPE: PRT
<213> ORGANISM: Artificial Sequence
<220> FEATURE:
<223> OTHER INFORMATION: FKBP variant peptide
<220> FEATURE:
<221> NAME/KEY: Xaa
<222> LOCATION: (15)..(15)
<223> OTHER INFORMATION: Xaa = Phe, Ser
<220> FEATURE:
<221> NAME/KEY: Xaa
<222> LOCATION: (24)..(24)
<223> OTHER INFORMATION: Xaa = Val, Ala
<220> FEATURE:
<221> NAME/KEY: Xaa
<222> LOCATION: (25)..(25)
<223> OTHER INFORMATION: Xaa = His, Arg
<220> FEATURE:
<221> NAME/KEY: Xaa
<222> LOCATION: (36)..(36)
<223> OTHER INFORMATION: Xaa = Phe, Val
<220> FEATURE:
<221> NAME/KEY: Xaa
<222> LOCATION: (60)..(60)
<223> OTHER INFORMATION: Xaa = Glu, Gly
<220> FEATURE:
<221> NAME/KEY: Xaa
<222> LOCATION: (66)..(66)
<223> OTHER INFORMATION: Xaa = Met, Thr
<220> FEATURE:
<221> NAME/KEY: Xaa
<222> LOCATION: (71)..(71)
<223> OTHER INFORMATION: Xaa = Arg, Gly
<220> FEATURE:
<221> NAME/KEY: Xaa
<222> LOCATION: (100)..(100)
```

```
<223> OTHER INFORMATION: Xaa = Asp, Gly, Asn
<220> FEATURE:
<221> NAME/KEY: Xaa
<222> LOCATION: (102)..(102)
<223> OTHER INFORMATION: Xaa = Glu, Gly
<220> FEATURE:
<221> NAME/KEY: Xaa
<222> LOCATION: (105)..(105)
<223> OTHER INFORMATION: Xaa = Lys, Ile
<220> FEATURE:
<221> NAME/KEY: Xaa
<222> LOCATION: (106)..(106)
<223> OTHER INFORMATION: Xaa = Leu, Pro

<400> SEQUENCE: 2

Gly Val Gln Val Glu Thr Ile Ser Pro Gly Asp Gly Arg Thr Xaa Pro
1               5                   10                  15

Lys Arg Gly Gln Thr Cys Val Xaa Xaa Tyr Thr Gly Met Leu Glu Asp
            20                  25                  30

Gly Lys Lys Xaa Asp Ser Ser Arg Asp Arg Asn Lys Pro Phe Lys Phe
        35                  40                  45

Met Leu Gly Lys Gln Glu Val Ile Arg Gly Trp Xaa Glu Gly Val Ala
    50                  55                  60

Gln Xaa Ser Val Gly Gln Xaa Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Xaa Val Glu Leu Leu Xaa Xaa Glu
            100                 105

<210> SEQ ID NO 3
<211> LENGTH: 107
<212> TYPE: PRT
<213> ORGANISM: Artificial Sequence
<220> FEATURE:
<223> OTHER INFORMATION: FKBP variant polypeptide
<220> FEATURE:
<221> NAME/KEY: Xaa
<222> LOCATION: (1)..(107)
<223> OTHER INFORMATION: Xaa = any amino acid

<400> SEQUENCE: 3

Gly Val Gln Val Glu Thr Ile Ser Pro Gly Asp Gly Arg Thr Xaa Pro
1               5                   10                  15

Lys Arg Gly Gln Thr Cys Val Xaa Xaa Tyr Thr Gly Met Leu Glu Asp
            20                  25                  30

Gly Lys Lys Xaa Asp Ser Ser Arg Asp Arg Asn Lys Pro Phe Lys Phe
        35                  40                  45

Met Leu Gly Lys Gln Glu Val Ile Arg Gly Trp Xaa Glu Gly Val Ala
    50                  55                  60

Gln Xaa Ser Val Gly Gln Xaa Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Xaa Val Glu Leu Leu Xaa Xaa Glu
            100                 105

<210> SEQ ID NO 4
<211> LENGTH: 19
<212> TYPE: PRT
<213> ORGANISM: Artificial Sequence
<220> FEATURE:
<223> OTHER INFORMATION: divesity sequence peptide
```

<400> SEQUENCE: 4

Thr Arg Gly Val Glu Glu Val Ala Glu Gly Val Val Leu Arg Arg
1               5                   10                  15

Arg Gly Asn

<210> SEQ ID NO 5
<211> LENGTH: 159
<212> TYPE: PRT
<213> ORGANISM: Artificial Sequence
<220> FEATURE:
<223> OTHER INFORMATION: DHFR peptide

<400> SEQUENCE: 5

Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
                20                  25                  30

Arg Asn Thr Leu Asn Lys Pro Val Ile Met Gly Arg His Thr Trp Glu
            35                  40                  45

Ser Ile Gly Arg Pro Leu Pro Gly Arg Lys Asn Ile Ile Leu Ser Ser
        50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155

<210> SEQ ID NO 6
<211> LENGTH: 159
<212> TYPE: PRT
<213> ORGANISM: Artificial Sequence
<220> FEATURE:
<223> OTHER INFORMATION: DHFR variant peptide
<220> FEATURE:
<221> NAME/KEY: Xaa
<222> LOCATION: (12)..(12)
<223> OTHER INFORMATION: Xaa = His, Leu, Tyr
<220> FEATURE:
<221> NAME/KEY: Xaa
<222> LOCATION: (18)..(18)
<223> OTHER INFORMATION: Xaa = Asn, Thr
<220> FEATURE:
<221> NAME/KEY: Xaa
<222> LOCATION: (19)..(19)
<223> OTHER INFORMATION: Xaa = Ala, Val
<220> FEATURE:
<221> NAME/KEY: Xaa
<222> LOCATION: (42)..(42)
<223> OTHER INFORMATION: Xaa = Met, Thr
<220> FEATURE:
<221> NAME/KEY: Xaa
<222> LOCATION: (61)..(61)
<223> OTHER INFORMATION: Xaa = Ile, Phe
<220> FEATURE:
<221> NAME/KEY: Xaa
<222> LOCATION: (68)..(68)
<223> OTHER INFORMATION: Xaa = Thr, Ser -continued

```
<220> FEATURE:
<221> NAME/KEY: Xaa
<222> LOCATION: (98)..(98)
<223> OTHER INFORMATION: Xaa = Arg, His
<220> FEATURE:
<221> NAME/KEY: Xaa
<222> LOCATION: (100)..(100)
<223> OTHER INFORMATION: Xaa = Tyr, Ile
<220> FEATURE:
<221> NAME/KEY: Xaa
<222> LOCATION: (103)..(103)
<223> OTHER INFORMATION: Xaa = Phe, Leu, Ser
<220> FEATURE:
<221> NAME/KEY: Xaa
<222> LOCATION: (114)..(114)
<223> OTHER INFORMATION: Xaa = His, Arg
<220> FEATURE:
<221> NAME/KEY: Xaa
<222> LOCATION: (121)..(121)
<223> OTHER INFORMATION: Xaa = Gly, Val

<400> SEQUENCE: 6

Met Ile Ser Leu Ile Ala Ala Leu Ala Val Asp Xaa Val Ile Gly Met
1               5                   10                  15

Glu Xaa Xaa Met Pro Trp Asn Leu Pro Ala Asp Leu Ala Trp Phe Lys
            20                  25                  30

Arg Asn Thr Leu Asn Lys Pro Val Ile Xaa Gly Arg His Thr Trp Glu
        35                  40                  45

Ser Ile Gly Arg Pro Leu Pro Gly Arg Lys Asn Ile Xaa Leu Ser Ser
    50                  55                  60

Gln Pro Ser Xaa Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Xaa Val Xaa Glu Gln Xaa Leu Pro Lys Ala Gln Lys Leu Tyr Leu
            100                 105                 110

Thr Xaa Ile Asp Ala Glu Val Glu Xaa Asp Thr His Phe Pro Asp Phe
        115                 120                 125

Glu Pro Asp Asp Trp Glu Ser Val Phe Ser Glu Phe His Asp Ala Asp
130                 135                 140

Ala Gln Asn Ser His Ser Tyr Cys Phe Glu Ile Leu Glu Arg Arg
145                 150                 155

<210> SEQ ID NO 7
<211> LENGTH: 159
<212> TYPE: PRT
<213> ORGANISM: Artificial Sequence
<220> FEATURE:
<223> OTHER INFORMATION: DHFR variant peptide
<220> FEATURE:
<221> NAME/KEY: Xaa
<222> LOCATION: (1)..(159)
<223> OTHER INFORMATION: Xaa = any amino acid

<400> SEQUENCE: 7

Met Ile Ser Leu Ile Ala Ala Leu Ala Val Asp Xaa Val Ile Gly Met
1               5                   10                  15

Glu Xaa Xaa Met Pro Trp Asn Leu Pro Ala Asp Leu Ala Trp Phe Lys
            20                  25                  30

Arg Asn Thr Leu Asn Lys Pro Val Ile Xaa Gly Arg His Thr Trp Glu
        35                  40                  45

Ser Ile Gly Arg Pro Leu Pro Gly Arg Lys Asn Ile Xaa Leu Ser Ser
    50                  55                  60
```

Gln Pro Ser Xaa Asp Asp Arg Val Thr Trp Val Lys Ser Val Asp Glu
 65                  70                  75                  80

Ala Ile Ala Ala Cys Gly Asp Val Pro Glu Ile Met Val Ile Gly Gly
             85                  90                  95

Gly Xaa Val Xaa Glu Gln Xaa Leu Pro Lys Ala Gln Lys Leu Tyr Leu
        100                 105                 110

Thr Xaa Ile Asp Ala Glu Val Glu Xaa Asp Thr His Phe Pro Asp Phe
        115                 120                 125

Glu Pro Asp Asp Trp Glu Ser Val Phe Ser Glu Phe His Asp Ala Asp
        130                 135                 140

Ala Gln Asn Ser His Ser Tyr Cys Phe Glu Ile Leu Glu Arg Arg
145                 150                 155

<210> SEQ ID NO 8
<211> LENGTH: 273
<212> TYPE: PRT
<213> ORGANISM: Artificial Sequence
<220> FEATURE:
<223> OTHER INFORMATION: ERBD Peptide

<400> SEQUENCE: 8

Ser Leu Ala Leu Ser Leu Thr Ala Asp Gln Met Val Ser Ala Leu Leu
 1               5                  10                  15

Asp Ala Glu Pro Pro Ile Leu Tyr Ser Glu Tyr Asp Pro Thr Arg Pro
             20                  25                  30

Phe Ser Glu Ala Ser Met Met Gly Leu Leu Thr Asn Leu Ala Asp Arg
         35                  40                  45

Glu Leu Val His Met Ile Asn Trp Ala Lys Arg Val Pro Gly Phe Val
 50                  55                  60

Asp Leu Thr Leu His Asp Gln Val His Leu Leu Glu Cys Ala Trp Leu
 65                  70                  75                  80

Glu Ile Leu Met Ile Gly Leu Val Trp Arg Ser Met Glu His Pro Gly
             85                  90                  95

Lys Leu Leu Phe Ala Pro Asn Leu Leu Leu Asp Arg Asn Gln Gly Lys
        100                 105                 110

Cys Val Glu Gly Met Val Glu Ile Phe Asp Met Leu Leu Ala Thr Ser
        115                 120                 125

Ser Arg Phe Arg Met Met Asn Leu Gln Gly Glu Glu Phe Val Cys Leu
        130                 135                 140

Lys Ser Ile Ile Leu Leu Asn Ser Gly Val Tyr Thr Phe Leu Ser Ser
145                 150                 155                 160

Thr Leu Lys Ser Leu Glu Glu Lys Asp His Ile His Arg Val Leu Asp
                165                 170                 175

Lys Ile Thr Asp Thr Leu Ile His Leu Met Ala Lys Ala Gly Leu Thr
            180                 185                 190

Leu Gln Gln Gln His Gln Arg Leu Ala Gln Leu Leu Leu Ile Leu Ser
        195                 200                 205

His Ile Arg His Met Ser Asn Lys Gly Met Glu His Leu Tyr Ser Met
    210                 215                 220

Lys Cys Lys Asn Val Val Pro Leu Tyr Asp Leu Leu Leu Glu Met Leu
225                 230                 235                 240

Asp Ala His Arg Leu Gly Gly Ser Gly Gly Ser Thr Arg Lys
                245                 250                 255

His Lys Ile Leu His Arg Leu Leu Gln Asp Ser Ser Arg Arg Arg Gly
                260                 265                 270

Asn

<210> SEQ ID NO 9
<211> LENGTH: 245
<212> TYPE: PRT
<213> ORGANISM: Artificial Sequence
<220> FEATURE:
<223> OTHER INFORMATION: ERBD peptide

<400> SEQUENCE: 9

Ser Leu Ala Leu Ser Leu Thr Ala Asp Gln Met Val Ser Ala Leu Leu
1               5                   10                  15

Asp Ala Glu Pro Pro Ile Leu Tyr Ser Glu Tyr Asp Pro Thr Arg Pro
            20                  25                  30

Phe Ser Glu Ala Ser Met Met Gly Leu Leu Thr Asn Leu Ala Asp Arg
        35                  40                  45

Glu Leu Val His Met Ile Asn Trp Ala Lys Arg Val Pro Gly Phe Val
    50                  55                  60

Asp Leu Thr Leu His Asp Gln Val His Leu Leu Glu Cys Ala Trp Leu
65                  70                  75                  80

Glu Ile Leu Met Ile Gly Leu Val Trp Arg Ser Met Glu His Pro Gly
                85                  90                  95

Lys Leu Leu Phe Ala Pro Asn Leu Leu Leu Asp Arg Asn Gln Gly Lys
            100                 105                 110

Cys Val Glu Gly Met Val Glu Ile Phe Asp Met Leu Leu Ala Thr Ser
        115                 120                 125

Ser Arg Phe Arg Met Met Asn Leu Gln Gly Glu Glu Phe Val Cys Leu
    130                 135                 140

Lys Ser Ile Ile Leu Leu Asn Ser Gly Val Tyr Thr Phe Leu Ser Ser
145                 150                 155                 160

Thr Leu Lys Ser Leu Glu Glu Lys Asp His Ile His Arg Val Leu Asp
                165                 170                 175

Lys Ile Thr Asp Thr Leu Ile His Leu Met Ala Lys Ala Gly Leu Thr
            180                 185                 190

Leu Gln Gln Gln His Gln Arg Leu Ala Gln Leu Leu Leu Ile Leu Ser
        195                 200                 205

His Ile Arg His Met Ser Asn Lys Gly Met Glu His Leu Tyr Ser Met
    210                 215                 220

Lys Cys Lys Asn Val Val Pro Leu Tyr Asp Leu Leu Leu Glu Met Leu
225                 230                 235                 240

Asp Ala His Arg Leu
                245

<210> SEQ ID NO 10
<211> LENGTH: 4
<212> TYPE: PRT
<213> ORGANISM: Artificial Sequence
<220> FEATURE:
<223> OTHER INFORMATION: degron peptide

<400> SEQUENCE: 10

Arg Arg Arg Gly
1

<210> SEQ ID NO 11
<211> LENGTH: 5
<212> TYPE: PRT
<213> ORGANISM: Artificial Sequence
<220> FEATURE:

<223> OTHER INFORMATION: bacterial degron peptide

<400> SEQUENCE: 11

Tyr Ala Leu Ala Ala
1               5

<210> SEQ ID NO 12
<211> LENGTH: 5
<212> TYPE: PRT
<213> ORGANISM: Artificial Sequence
<220> FEATURE:
<223> OTHER INFORMATION: degron peptide

<400> SEQUENCE: 12

Arg Arg Arg Gly Asn
1               5

<210> SEQ ID NO 13
<211> LENGTH: 13
<212> TYPE: PRT
<213> ORGANISM: Artificial Sequence
<220> FEATURE:
<223> OTHER INFORMATION: peptide

<400> SEQUENCE: 13

Lys His Lys Ile Leu His Arg Leu Leu Gln Asp Ser Ser
1               5                   10

<210> SEQ ID NO 14
<211> LENGTH: 144
<212> TYPE: PRT
<213> ORGANISM: Artificial Sequence
<220> FEATURE:
<223> OTHER INFORMATION: AsLOV2 peptide

<400> SEQUENCE: 14

Phe Leu Ala Thr Thr Leu Glu Arg Ile Glu Lys Asn Phe Val Ile Thr
1               5                   10                  15

Asp Pro Arg Leu Pro Asp Asn Pro Ile Ile Phe Ala Ser Asp Ser Phe
                20                  25                  30

Leu Gln Leu Thr Glu Tyr Ser Arg Glu Glu Ile Leu Gly Arg Asn Cys
            35                  40                  45

Arg Phe Leu Gln Gly Pro Glu Thr Asp Arg Ala Thr Val Arg Lys Ile
        50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu His Val Arg Asp Ala Ala Glu Arg Glu Gly Val Met
        115                 120                 125

Leu Ile Lys Lys Thr Ala Glu Asn Ile Asp Glu Ala Ala Lys Glu Leu
    130                 135                 140

<210> SEQ ID NO 15
<211> LENGTH: 144
<212> TYPE: PRT
<213> ORGANISM: Artificial Sequence
<220> FEATURE:
<223> OTHER INFORMATION: AsLOV2 variant peptide
<220> FEATURE:
<221> NAME/KEY: Xaa

```
<222> LOCATION: (14)..(14)
<223> OTHER INFORMATION: Xaa = Val, Ala, Ile
<220> FEATURE:
<221> NAME/KEY: Xaa
<222> LOCATION: (80)..(80)
<223> OTHER INFORMATION: Xaa = Asn, Lys, Arg
<220> FEATURE:
<221> NAME/KEY: Xaa
<222> LOCATION: (120)..(120)
<223> OTHER INFORMATION: Xaa = Asp, Glu, Ala
<220> FEATURE:
<221> NAME/KEY: Xaa
<222> LOCATION: (126)..(126)
<223> OTHER INFORMATION: Xaa = Gly, Ala
<220> FEATURE:
<221> NAME/KEY: Xaa
<222> LOCATION: (127)..(127)
<223> OTHER INFORMATION: Xaa = Val, Asn
<220> FEATURE:
<221> NAME/KEY: Xaa
<222> LOCATION: (130)..(130)
<223> OTHER INFORMATION: Xaa = Ile, Ala
<220> FEATURE:
<221> NAME/KEY: Xaa
<222> LOCATION: (136)..(136)
<223> OTHER INFORMATION: Xaa = Asn, Glu, Asp
<220> FEATURE:
<221> NAME/KEY: Xaa
<222> LOCATION: (142)..(142)
<223> OTHER INFORMATION: Xaa = Lys or No Amino Acid
<220> FEATURE:
<221> NAME/KEY: Xaa
<222> LOCATION: (143)..(143)
<223> OTHER INFORMATION: Xaa = Glu or No Amino Acid
<220> FEATURE:
<221> NAME/KEY: Xaa
<222> LOCATION: (144)..(144)
<223> OTHER INFORMATION: Xaa = Leu or No Amino Acid

<400> SEQUENCE: 15

Phe Leu Ala Thr Thr Leu Glu Arg Ile Glu Lys Asn Phe Xaa Ile Thr
1               5                   10                  15

Asp Pro Arg Leu Pro Asp Asn Pro Ile Ile Phe Ala Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Xaa
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu His Val Arg Xaa Ala Ala Glu Arg Gln Xaa Xaa Met
        115                 120                 125

Leu Xaa Lys Lys Thr Ala Glu Xaa Ile Asp Glu Ala Ala Xaa Xaa Xaa
    130                 135                 140

<210> SEQ ID NO 16
<211> LENGTH: 144
<212> TYPE: PRT
<213> ORGANISM: Artificial Sequence
<220> FEATURE:
<223> OTHER INFORMATION: AsLOV2 variant peptide
<220> FEATURE:
<221> NAME/KEY: Xaa
<222> LOCATION: (1)..(144)
<223> OTHER INFORMATION: Xaa = any amino acid
```

<400> SEQUENCE: 16

Phe Leu Ala Thr Thr Leu Glu Arg Ile Glu Lys Asn Phe Xaa Ile Thr
1               5                   10                  15

Asp Pro Arg Leu Pro Asp Asn Pro Ile Ile Phe Ala Ser Asp Ser Phe
            20                  25                  30

Leu Gln Leu Thr Glu Tyr Ser Arg Glu Ile Leu Gly Arg Asn Cys
        35                  40                  45

Arg Phe Leu Gln Gly Pro Glu Thr Asp Arg Ala Thr Val Arg Lys Ile
50                  55                  60

Arg Asp Ala Ile Asp Asn Gln Thr Glu Val Thr Val Gln Leu Ile Xaa
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu His Val Arg Xaa Ala Ala Glu Arg Glu Xaa Xaa Met
        115                 120                 125

Leu Xaa Lys Lys Thr Ala Glu Xaa Ile Asp Glu Ala Ala Xaa Xaa Xaa
    130                 135                 140

<210> SEQ ID NO 17
<211> LENGTH: 114
<212> TYPE: PRT
<213> ORGANISM: Artificial Sequence
<220> FEATURE:
<223> OTHER INFORMATION: CD3 zeta peptide

<400> SEQUENCE: 17

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Gly Arg Asp Pro Glu Met Gly Gly
        35                  40                  45

Lys Pro Gln Arg Arg Lys Asn Pro Gln Glu Gly Leu Tyr Asn Glu Leu
50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg

<210> SEQ ID NO 18
<211> LENGTH: 42
<212> TYPE: PRT
<213> ORGANISM: Artificial Sequence
<220> FEATURE:
<223> OTHER INFORMATION: Fc epsilon receptor subunit gamma peptide

<400> SEQUENCE: 18

Arg Leu Lys Ile Gln Val Arg Lys Ala Ala Ile Thr Ser Tyr Glu Lys
1               5                   10                  15

Ser Asp Gly Val Tyr Thr Gly Leu Ser Thr Arg Asn Gln Glu Thr Tyr
            20                  25                  30

Glu Thr Leu Lys His Glu Lys Pro Pro Gln
        35                  40

<210> SEQ ID NO 19
<211> LENGTH: 44
<212> TYPE: PRT
<213> ORGANISM: Artificial Sequence
<220> FEATURE:
<223> OTHER INFORMATION: Fc epsilon receptor subunit beta peptide

<400> SEQUENCE: 19

Ile Cys Gly Ala Gly Glu Glu Leu Lys Gly Asn Lys Val Pro Glu Asp
1               5                   10                  15

Arg Val Tyr Glu Glu Leu Asn Ile Tyr Ser Ala Thr Tyr Ser Glu Leu
            20                  25                  30

Glu Asp Pro Gly Glu Met Ser Pro Pro Ile Asp Leu
        35                  40

<210> SEQ ID NO 20
<211> LENGTH: 44
<212> TYPE: PRT
<213> ORGANISM: Artificial Sequence
<220> FEATURE:
<223> OTHER INFORMATION: CD3 gamma peptide

<400> SEQUENCE: 20

Gln Asp Gly Val Arg Gln Ser Arg Ala Ser Asp Lys Gln Thr Leu Leu
1               5                   10                  15

Pro Asn Asp Gln Leu Tyr Gln Pro Leu Lys Asp Arg Glu Asp Asp Gln
            20                  25                  30

Tyr Ser His Leu Gln Gly Asn Gln Leu Arg Arg Asn
        35                  40

<210> SEQ ID NO 21
<211> LENGTH: 44
<212> TYPE: PRT
<213> ORGANISM: Artificial Sequence
<220> FEATURE:
<223> OTHER INFORMATION: CD3 delta peptide

<400> SEQUENCE: 21

His Glu Thr Gly Arg Leu Ser Gly Ala Ala Asp Thr Gln Ala Leu Leu
1               5                   10                  15

Arg Asn Asp Gln Val Tyr Gln Pro Leu Arg Asp Arg Asp Asp Ala Gln
            20                  25                  30

Tyr Ser His Leu Gly Gly Asn Trp Ala Arg Asn Lys
        35                  40

<210> SEQ ID NO 22
<211> LENGTH: 55
<212> TYPE: PRT
<213> ORGANISM: Artificial Sequence
<220> FEATURE:
<223> OTHER INFORMATION: CD3 epsilon peptide

<400> SEQUENCE: 22

Lys Asn Arg Lys Ala Lys Ala Lys Pro Val Thr Arg Gly Ala Gly Ala
1               5                   10                  15

Gly Gly Arg Gln Arg Gly Gln Asn Lys Glu Arg Pro Pro Pro Val Pro
            20                  25                  30

Asn Pro Asp Tyr Glu Pro Ile Arg Lys Gly Gln Arg Asp Leu Tyr Ser
        35                  40                  45

Gly Leu Asn Gln Arg Arg Ile
    50                  55

<210> SEQ ID NO 23
<211> LENGTH: 94
<212> TYPE: PRT
<213> ORGANISM: Artificial Sequence
<220> FEATURE:
<223> OTHER INFORMATION: CD5 peptide

<400> SEQUENCE: 23

Tyr Lys Lys Leu Val Lys Lys Phe Arg Gln Lys Lys Gln Arg Gln Trp
1               5                   10                  15

Ile Gly Pro Thr Gly Met Asn Gln Asn Met Ser Phe His Arg Asn His
            20                  25                  30

Thr Ala Thr Val Arg Ser His Ala Glu Asn Pro Thr Ala Ser His Val
        35                  40                  45

Asp Asn Glu Tyr Ser Gln Pro Pro Arg Asn Ser His Leu Ser Ala Tyr
    50                  55                  60

Pro Ala Leu Glu Gly Ala Leu His Arg Ser Ser Met Gln Pro Asp Asn
65                  70                  75                  80

Ser Ser Asp Ser Asp Tyr Asp Leu His Gly Ala Gln Arg Leu
                85                  90

<210> SEQ ID NO 24
<211> LENGTH: 141
<212> TYPE: PRT
<213> ORGANISM: Artificial Sequence
<220> FEATURE:
<223> OTHER INFORMATION: CD22 peptide

<400> SEQUENCE: 24

Lys Leu Gln Arg Arg Trp Lys Arg Thr Gln Ser Gln Gln Gly Leu Gln
1               5                   10                  15

Glu Asn Ser Ser Gly Gln Ser Phe Phe Val Arg Asn Lys Lys Val Arg
            20                  25                  30

Arg Ala Pro Leu Ser Glu Gly Pro His Ser Leu Gly Cys Tyr Asn Pro
        35                  40                  45

Met Met Glu Asp Gly Ile Ser Tyr Thr Thr Leu Arg Phe Pro Glu Met
    50                  55                  60

Asn Ile Pro Arg Thr Gly Asp Ala Glu Ser Ser Glu Met Gln Arg Pro
65                  70                  75                  80

Pro Pro Asp Cys Asp Asp Thr Val Thr Tyr Ser Ala Leu His Lys Arg
                85                  90                  95

Gln Val Gly Asp Tyr Glu Asn Val Ile Pro Asp Phe Pro Glu Asp Glu
            100                 105                 110

Gly Ile His Tyr Ser Glu Leu Ile Gln Phe Gly Val Gly Glu Arg Pro
        115                 120                 125

Gln Ala Gln Glu Asn Val Asp Tyr Val Ile Leu Lys His
    130                 135                 140

<210> SEQ ID NO 25
<211> LENGTH: 61
<212> TYPE: PRT
<213> ORGANISM: Artificial Sequence
<220> FEATURE:
<223> OTHER INFORMATION: CD79a peptide

<400> SEQUENCE: 25

Arg Lys Arg Trp Gln Asn Glu Lys Leu Gly Leu Asp Ala Gly Asp Glu

```
                1               5                   10                  15
Tyr Glu Asp Glu Asn Leu Tyr Glu Gly Leu Asn Leu Asp Asp Cys Ser
                20                  25                  30

Met Tyr Glu Asp Ile Ser Arg Gly Leu Gln Gly Thr Tyr Gln Asp Val
            35                  40                  45

Gly Ser Leu Asn Ile Gly Asp Val Gln Leu Glu Lys Pro
        50                  55                  60
```

<210> SEQ ID NO 26
<211> LENGTH: 64
<212> TYPE: PRT
<213> ORGANISM: Artificial Sequence
<220> FEATURE:
<223> OTHER INFORMATION: CD79b peptide

<400> SEQUENCE: 26

```
Thr Leu Leu Ile Ile Leu Phe Ile Ile Val Pro Ile Phe Leu Leu Leu
1               5                   10                  15

Asp Lys Asp Asp Ser Lys Ala Gly Met Glu Glu Asp His Thr Tyr Glu
                20                  25                  30

Gly Leu Asp Ile Asp Gln Thr Ala Thr Tyr Glu Asp Ile Val Thr Leu
            35                  40                  45

Arg Thr Gly Glu Val Lys Trp Ser Val Gly Glu His Pro Gly Pro Glu
        50                  55                  60
```

<210> SEQ ID NO 27
<211> LENGTH: 76
<212> TYPE: PRT
<213> ORGANISM: Artificial Sequence
<220> FEATURE:
<223> OTHER INFORMATION: CD66d peptide

<400> SEQUENCE: 27

```
Ala Lys Thr Gly Arg Thr Ser Ile Gln Arg Asp Leu Lys Glu Gln Gln
1               5                   10                  15

Pro Gln Ala Leu Ala Pro Gly Arg Gly Pro Ser His Ser Ser Ala Phe
                20                  25                  30

Ser Met Ser Pro Leu Ser Thr Ala Gln Ala Pro Leu Pro Asn Pro Arg
            35                  40                  45

Thr Ala Ala Ser Ile Tyr Glu Glu Leu Leu Lys His Asp Thr Asn Ile
        50                  55                  60

Tyr Cys Arg Met Asp His Lys Ala Glu Val Ala Ser
65                  70                  75
```

<210> SEQ ID NO 28
<211> LENGTH: 116
<212> TYPE: PRT
<213> ORGANISM: Artificial Sequence
<220> FEATURE:
<223> OTHER INFORMATION: CD2 peptide

<400> SEQUENCE: 28

```
Lys Arg Lys Lys Gln Arg Ser Arg Arg Asn Asp Glu Glu Leu Glu Thr
1               5                   10                  15

Arg Ala His Arg Val Ala Thr Glu Glu Arg Gly Arg Lys Pro His Gln
                20                  25                  30

Ile Pro Ala Ser Thr Pro Gln Asn Pro Ala Thr Ser Gln His Pro Pro
            35                  40                  45

Pro Pro Pro Gly His Arg Ser Gln Ala Pro Ser His Arg Pro Pro Pro
        50                  55                  60
```

Pro Gly His Arg Val Gln His Gln Pro Gln Lys Arg Pro Pro Ala Pro
65                  70                  75                  80

Ser Gly Thr Gln Val His Gln Lys Gly Pro Pro Leu Pro Arg Pro
                85                  90                  95

Arg Val Gln Pro Lys Pro Pro His Gly Ala Ala Glu Asn Ser Leu Ser
            100                 105                 110

Pro Ser Ser Asn
        115

<210> SEQ ID NO 29
<211> LENGTH: 38
<212> TYPE: PRT
<213> ORGANISM: Artificial Sequence
<220> FEATURE:
<223> OTHER INFORMATION: CD4 peptide

<400> SEQUENCE: 29

Arg Cys Arg His Arg Arg Arg Gln Ala Glu Arg Met Ser Gln Ile Lys
1               5                   10                  15

Arg Leu Leu Ser Glu Lys Lys Thr Cys Gln Cys Pro His Arg Phe Gln
            20                  25                  30

Lys Thr Cys Ser Pro Ile
        35

<210> SEQ ID NO 30
<211> LENGTH: 94
<212> TYPE: PRT
<213> ORGANISM: Artificial Sequence
<220> FEATURE:
<223> OTHER INFORMATION: CD5 peptide

<400> SEQUENCE: 30

Tyr Lys Lys Leu Val Lys Lys Phe Arg Gln Lys Lys Gln Arg Gln Trp
1               5                   10                  15

Ile Gly Pro Thr Gly Met Asn Gln Asn Met Ser Phe His Arg Asn His
            20                  25                  30

Thr Ala Thr Val Arg Ser His Ala Glu Asn Pro Thr Ala Ser His Val
        35                  40                  45

Asp Asn Glu Tyr Ser Gln Pro Pro Arg Asn Ser His Leu Ser Ala Tyr
    50                  55                  60

Pro Ala Leu Glu Gly Ala Leu His Arg Ser Ser Met Gln Pro Asp Asn
65                  70                  75                  80

Ser Ser Asp Ser Asp Tyr Asp Leu His Gly Ala Gln Arg Leu
                85                  90

<210> SEQ ID NO 31
<211> LENGTH: 29
<212> TYPE: PRT
<213> ORGANISM: Artificial Sequence
<220> FEATURE:
<223> OTHER INFORMATION: CD8 alpha peptide

<400> SEQUENCE: 31

Asn His Arg Asn Arg Arg Arg Val Cys Lys Cys Pro Arg Pro Val Val
1               5                   10                  15

Lys Ser Gly Asp Lys Pro Ser Leu Ser Ala Arg Tyr Val
            20                  25

<210> SEQ ID NO 32
<211> LENGTH: 15

<212> TYPE: PRT
<213> ORGANISM: Artificial Sequence
<220> FEATURE:
<223> OTHER INFORMATION: CD8 beta peptide

<400> SEQUENCE: 32

Arg Arg Arg Arg Ala Arg Leu Arg Phe Met Lys Gln Phe Tyr Lys
1               5                   10                  15

<210> SEQ ID NO 33
<211> LENGTH: 40
<212> TYPE: PRT
<213> ORGANISM: Artificial Sequence
<220> FEATURE:
<223> OTHER INFORMATION: CD28 peptide

<400> SEQUENCE: 33

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 34
<211> LENGTH: 42
<212> TYPE: PRT
<213> ORGANISM: Artificial Sequence
<220> FEATURE:
<223> OTHER INFORMATION: CD137 TNF receptor member 9 peptide

<400> SEQUENCE: 34

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 35
<211> LENGTH: 37
<212> TYPE: PRT
<213> ORGANISM: Artificial Sequence
<220> FEATURE:
<223> OTHER INFORMATION: CD134 TNF receptor member 4

<400> SEQUENCE: 35

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35

<210> SEQ ID NO 36
<211> LENGTH: 34
<212> TYPE: PRT
<213> ORGANISM: Artificial Sequence
<220> FEATURE:
<223> OTHER INFORMATION: T-cell costimulator (ICOS) peptide

<400> SEQUENCE: 36

Lys Lys Lys Tyr Ser Ser Ser Val His Asp Pro Asn Gly Glu Tyr Met
1               5                   10                  15

```
Phe Met Arg Ala Val Asn Thr Ala Lys Lys Ser Arg Leu Thr Asp Val
            20                  25                  30

Thr Leu

<210> SEQ ID NO 37
<211> LENGTH: 28
<212> TYPE: PRT
<213> ORGANISM: Artificial Sequence
<220> FEATURE:
<223> OTHER INFORMATION: CD28 transmembrane peptide

<400> SEQUENCE: 37

Phe Trp Val Leu Val Val Val Gly Gly Val Leu Ala Cys Tyr Ser Leu
1               5                   10                  15

Leu Val Thr Val Ala Phe Ile Ile Phe Trp Val Arg
            20                  25

<210> SEQ ID NO 38
<211> LENGTH: 22
<212> TYPE: PRT
<213> ORGANISM: Artificial Sequence
<220> FEATURE:
<223> OTHER INFORMATION: GITR, TNF receptor member 18 transmembrane
      element

<400> SEQUENCE: 38

Pro Leu Gly Trp Leu Thr Val Val Leu Leu Ala Val Ala Ala Cys Val
1               5                   10                  15

Leu Leu Leu Thr Ser Ala
            20

<210> SEQ ID NO 39
<211> LENGTH: 61
<212> TYPE: PRT
<213> ORGANISM: Artificial Sequence
<220> FEATURE:
<223> OTHER INFORMATION: CD8 alpha hinge region

<400> SEQUENCE: 39

Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu Asp
    50                  55                  60

<210> SEQ ID NO 40
<211> LENGTH: 61
<212> TYPE: PRT
<213> ORGANISM: Artificial Sequence
<220> FEATURE:
<223> OTHER INFORMATION: CD8 beta spacer element peptide

<400> SEQUENCE: 40

Val Asp Phe Leu Pro Thr Thr Ala Gln Pro Thr Lys Lys Ser Thr Leu
1               5                   10                  15

Lys Lys Arg Val Cys Arg Leu Pro Arg Pro Glu Thr Gln Lys Gly Pro
            20                  25                  30

Leu Cys Ser Pro Ile Thr Leu Gly Leu Leu Val Ala Gly Val Leu Val
        35                  40                  45
```

```
Leu Leu Val Ser Leu Gly Val Ala Ile His Leu Cys Cys
    50                  55                  60
```

<210> SEQ ID NO 41
<211> LENGTH: 82
<212> TYPE: PRT
<213> ORGANISM: Artificial Sequence
<220> FEATURE:
<223> OTHER INFORMATION: CD4 315-396 spacer element

<400> SEQUENCE: 41

```
Val Val Met Arg Ala Thr Gln Leu Gln Lys Asn Leu Thr Cys Glu Val
1               5                   10                  15

Trp Gly Pro Thr Ser Pro Lys Leu Met Leu Ser Leu Lys Leu Glu Asn
                20                  25                  30

Lys Glu Ala Lys Val Ser Lys Arg Glu Lys Ala Val Trp Val Leu Asn
            35                  40                  45

Pro Glu Ala Gly Met Trp Gln Cys Leu Leu Ser Asp Ser Gly Gln Val
        50                  55                  60

Leu Leu Glu Ser Asn Ile Lys Val Leu Pro Thr Trp Ser Thr Pro Val
65                  70                  75                  80

Gln Pro
```

<210> SEQ ID NO 42
<211> LENGTH: 16
<212> TYPE: PRT
<213> ORGANISM: Artificial Sequence
<220> FEATURE:
<223> OTHER INFORMATION: CD28 137-152 spacer element peptide

<400> SEQUENCE: 42

```
Gly Lys His Leu Cys Pro Ser Pro Leu Phe Pro Gly Pro Ser Lys Pro
1               5                   10                  15
```

<210> SEQ ID NO 43
<211> LENGTH: 49
<212> TYPE: PRT
<213> ORGANISM: Artificial Sequence
<220> FEATURE:
<223> OTHER INFORMATION: TNF receptor member 19 peptide

<400> SEQUENCE: 43

```
Arg Ser Gln Cys Met Trp Pro Arg Glu Thr Gln Leu Leu Leu Glu Val
1               5                   10                  15

Pro Pro Ser Thr Glu Asp Ala Arg Ser Cys Gln Phe Pro Glu Glu Glu
                20                  25                  30

Arg Gly Glu Arg Ser Ala Glu Glu Lys Gly Arg Leu Gly Asp Leu Trp
            35                  40                  45

Val
```

<210> SEQ ID NO 44
<211> LENGTH: 30
<212> TYPE: PRT
<213> ORGANISM: Artificial Sequence
<220> FEATURE:
<223> OTHER INFORMATION: GPI signal sequence from CD24

<400> SEQUENCE: 44

```
Thr Asn Ala Thr Thr Lys Ala Ala Gly Gly Ala Leu Gln Ser Thr Ala
1               5                   10                  15

Ser Leu Phe Val Val Ser Leu Ser Leu Leu His Leu Tyr Ser
```

20          25          30

<210> SEQ ID NO 45
<211> LENGTH: 32
<212> TYPE: PRT
<213> ORGANISM: Artificial Sequence
<220> FEATURE:
<223> OTHER INFORMATION: GPI signal sequence from CNTN1

<400> SEQUENCE: 45

Val Ser Gln Val Lys Ile Ser Gly Ala Pro Thr Leu Ser Pro Ser Leu
1               5                   10                  15

Leu Gly Leu Leu Leu Pro Ala Phe Gly Ile Leu Val Tyr Leu Glu Phe
            20                  25                  30

<210> SEQ ID NO 46
<211> LENGTH: 35
<212> TYPE: PRT
<213> ORGANISM: Artificial Sequence
<220> FEATURE:
<223> OTHER INFORMATION: GPI signal sequence from EFNA1

<400> SEQUENCE: 46

Pro Glu Val Arg Val Leu His Ser Ile Gly His Ser Ala Ala Pro Arg
1               5                   10                  15

Leu Phe Pro Leu Ala Trp Thr Val Leu Leu Leu Pro Leu Leu Leu Leu
            20                  25                  30

Gln Thr Pro
        35

<210> SEQ ID NO 47
<211> LENGTH: 35
<212> TYPE: PRT
<213> ORGANISM: Artificial Sequence
<220> FEATURE:
<223> OTHER INFORMATION: GPI signal sequence from EFNA2

<400> SEQUENCE: 47

Glu Ala Pro Glu Pro Ile Phe Thr Ser Asn Asn Ser Cys Ser Ser Pro
1               5                   10                  15

Gly Gly Cys Arg Leu Phe Leu Ser Thr Ile Pro Val Leu Trp Arg Leu
            20                  25                  30

Leu Gly Ser
        35

<210> SEQ ID NO 48
<211> LENGTH: 35
<212> TYPE: PRT
<213> ORGANISM: Artificial Sequence
<220> FEATURE:
<223> OTHER INFORMATION: GPI signal sequence from EFNA3

<400> SEQUENCE: 48

Gln Val Pro Lys Leu Glu Lys Ser Ile Ser Gly Thr Ser Pro Lys Arg
1               5                   10                  15

Glu His Leu Pro Leu Ala Val Gly Ile Ala Phe Phe Leu Met Thr Phe
            20                  25                  30

Leu Ala Ser
        35

<210> SEQ ID NO 49
<211> LENGTH: 35
<212> TYPE: PRT

```
<213> ORGANISM: Artificial Sequence
<220> FEATURE:
<223> OTHER INFORMATION: GPI signal sequence from EFNA5

<400> SEQUENCE: 49

Glu Ser Ala Glu Pro Ser Arg Gly Glu Asn Ala Ala Gln Thr Pro Arg
1               5                   10                  15

Ile Pro Ser Arg Leu Leu Ala Ile Leu Leu Phe Leu Leu Ala Met Leu
            20                  25                  30

Leu Thr Leu
        35

<210> SEQ ID NO 50
<211> LENGTH: 29
<212> TYPE: PRT
<213> ORGANISM: Artificial Sequence
<220> FEATURE:
<223> OTHER INFORMATION: GPI signal sequence from FOLI

<400> SEQUENCE: 50

Tyr Ala Ala Ala Met Ser Gly Ala Gly Pro Trp Ala Ala Trp Pro Phe
1               5                   10                  15

Leu Leu Ser Leu Ala Leu Met Leu Leu Trp Leu Leu Ser
            20                  25

<210> SEQ ID NO 51
<211> LENGTH: 29
<212> TYPE: PRT
<213> ORGANISM: Artificial Sequence
<220> FEATURE:
<223> OTHER INFORMATION: GPI signal sequence from LSAMP

<400> SEQUENCE: 51

Ser Val Arg Gly Ile Asn Gly Ser Ile Ser Leu Ala Val Pro Leu Trp
1               5                   10                  15

Leu Leu Ala Ala Ser Leu Leu Cys Leu Leu Ser Lys Cys
            20                  25

<210> SEQ ID NO 52
<211> LENGTH: 32
<212> TYPE: PRT
<213> ORGANISM: Artificial Sequence
<220> FEATURE:
<223> OTHER INFORMATION: GPI signal sequence from PPB1

<400> SEQUENCE: 52

Thr Thr Asp Ala Ala His Pro Gly Arg Ser Val Val Pro Ala Leu Leu
1               5                   10                  15

Pro Leu Leu Ala Gly Thr Leu Leu Leu Glu Thr Ala Thr Ala Pro
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: GPI signal sequence from RTN4R

<400> SEQUENCE: 53

Asp Ser Glu Gly Ser Gly Ala Leu Pro Ser Leu Thr Cys Ser Leu Thr
1               5                   10                  15

Pro Leu Gly Leu Ala Leu Val Leu Trp Thr Val Leu Gly Pro Cys
            20                  25                  30
```

SMART CAR DEVICES, DE CAR POLYPEPTIDES, SIDE CARS AND USES THEREOF

This application is continuation of U.S. application Ser. No. 15/070,352 filed Mar. 15, 2016, which claims priority to U.S. provisional application Ser. No. 62/134,143 filed Mar. 17, 2015, U.S. provisional application Ser. No. 62/152,727 filed Apr. 24, 2015, U.S. provisional application Ser. No. 62/183,595 filed Jun. 23, 2015, and U.S. provisional application Ser. No. 62/276,449 filed Jan. 8, 2016.

FIELD OF THE INVENTION

The present invention relates generally to the field of RNA Control Devices and/or destabilizing elements (DE) combined with Chimeric Antigen Receptors (CARs) in eukaryotic cells. The present invention also relates to split CARs (Side-CARs) in eukaryotic cells. More specifically, the present invention relates to DEs, RNA Control Devices, and/or side-CARs combined with Chimeric Antigen Receptors to make small molecule actuatable CAR polypeptides. The present invention also relates to DE-CARs, Smart CARs (Smart=small molecule actuatable RNA trigger), Smart-DE-CARs, and/or Side-CARs for use in the treatment of disease.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CBIO010_ST25.txt", a creation date of Mar. 10, 2016, and a size of 40 kilobytes. The Sequence Listing filed via EFS-Web is part of the specification and is incorporated in its entirety by reference herein.

BACKGROUND OF THE INVENTION

CAR T cell therapy has been shown to be effective at inducing complete responses for acute lymphoblastic leukemia and other B-cell-related malignancies and has been shown to be effective at achieving and sustaining remissions for refractory/relapsed acute lymphoblastic leukemia (Maude et al., NEJM, 371:1507, 2014). However, dangerous side effects related to cytokine release syndrome (CRS), tumor lysis syndrome (TLS), B-cell aplasia and on-tumor, off-target toxicities have been seen in some patients.

There are currently two extant strategies to control CAR technology. The first is an inducible "kill switch." In this approach, one or more "suicide" genes that initiate apoptotic pathways are incorporated into the CAR construct (Budde et al. PLoS1, 2013 doi:10.1371/journal.pone.0082742). Activation of these suicide genes is initiated by the addition of AP1903 (also known as rimiducid), a lipid-permeable tachrolimus analog that initiates homodimerization of the human protein FKBP12 (Fv), to which the apoptosis-inducing proteins are translationally fused. In the ideal scenario, these kill switches endeavor to sacrifice the long-term surveillance benefit of CAR technology to safeguard against toxicity. However, in vivo, these suicide switches are not likely to realize this goal, as they are operating against powerful selection pressures for CAR T-cells that do not respond to AP1903, a situation worsened by the inimical error-prone retroviral copying associated with the insertion of stable transgenes into patient T-cells. In this scenario, non-responsive CAR T-cell clones will continue to proliferate and kill target cells in an antigen-dependent manner. Thus, kill switch technology is unlikely to provide an adequate safeguard against toxicity.

The second CAR regulatory approach is transient CAR expression, which can be achieved in several ways. In one approach, T-cells are harvested from unrelated donors, the HLA genes are deleted by genome-editing technology and CAR-encoding transgenes are inserted into the genome of these cells. Upon adoptive transfer, these CAR T-cells will be recognized by the recipient's immune system as being foreign and destroyed, thus the CAR exposure in this system is transient. In another transient CAR exposure approach, mRNA of a CAR-encoding gene is introduced into harvested patient T-cells (Beatty, G L 2014. Cancer Immunology Research 2 (2): 112-20. doi:10.1158/2326-6066.CIR-13-0170). As mRNA has a short half-life and is not replicated in the cell or stably maintained, there is no permanent alteration of the CAR-expressing T-cell, thus the CAR expression and activity will be for a short period of time. However, as with the kill-switch approach, these transient CAR exposure approaches sacrifice the surveillance benefit of CARs. Additionally, with these transient systems acute toxicity can be difficult to control.

SUMMARY OF THE INVENTION

In some embodiments, the invention relates to Smart-CAR, DE-CAR, Side-CAR constructs, and/or combinations thereof for use in eukaryotic cells. In some embodiments, the CAR constructs comprise a nucleic acid encoding a CAR (chimeric antigen receptor) with a nucleic acid encoding a Destabilizing Element or a nucleic acid encoding a RNA control device. In some embodiments, the invention relates to CARs, Smart CARs, DE-CARs, and/or Smart-DE-CARs that are comprised of at least two parts which associate to form a CAR, Smart CAR, DE-CAR and/or Smart-DE-CAR of the invention (Side-CARs).

In some embodiments, the RNA control device comprises a sensor element, a linker element, and an actuator element. In some embodiments, the nucleic acid encoding the CAR comprises nucleic acids encoding an extracellular antigen binding element, a transmembrane element, an intracellular signaling element, and a co-stimulatory element. In some embodiments, the nucleic acid encoding the CAR comprises nucleic acids encoding an extracellular antigen binding element, a transmembrane element, and an intracellular signaling element. In some embodiments the intracellular signaling element also includes a costimulatory sequence and function. In some embodiments, the Smart CAR nucleic acids of the invention are placed into an expression vector suitable for use in a eukaryotic cell. In some embodiments, the nucleic acid is a DNA or a RNA. In some embodiments, the RNA control device inhibits CAR polypeptide expression and when the sensor element of the RNA control device binds ligand CAR polypeptide expression is increased. In some embodiments, the RNA control device inhibits CAR polypeptide expression when ligand is bound to the sensor element, and when ligand is not bound to the sensor element CAR polypeptide expression is increased.

In some embodiments, the Smart CAR, DE-CAR, Smart-DE-CAR, and/or Side-CAR nucleic acids of the invention are placed into an expression vector suitable for use in a eukaryotic cell. In some embodiments, the nucleic acid is a DNA or an RNA. In some embodiments, the Destabilizing Element targets the DE-CAR polypeptide for proteolysis inside the eukaryotic cell. In some embodiments, the DE is capable of binding a ligand. In some embodiments, binding of ligand decreases proteolysis of the DE-CAR polypeptide in the eukaryotic cell. In some embodiments, binding of ligand increases proteolysis of the DE-CAR polypeptide in the eukaryotic cell. In some embodiments, the DE-CAR polypeptide is stable and not targeted for proteolysis when ligand is not bound. In some embodiments, the RNA control device inhibits CAR, DE-CAR, and/or Side-CAR polypeptide expression and when the sensor element of the RNA control device binds ligand CAR, DE-CAR, and/or Side-CAR polypeptide expression is increased. In some embodiments, the RNA control device inhibits CAR, DE-CAR, and/or Side-CAR polypeptide expression when ligand is bound to the sensor element, and when ligand is not bound to the sensor element CAR, DE-CAR, and/or Side-CAR polypeptide expression is increased.

In some embodiments, the two parts of the CAR, Smart CAR, DE-CAR and/or Smart-DE-CAR associate in response to a small molecule, polypeptide, or other stimulus (e.g., light, heat, etc.) In some embodiments, these split constructs are referred to as Side-CARs. In some embodiments, one part of the CAR, Smart-CAR, DE-CAR, and/or Smart-DE-CAR is membrane bound through a transmembrane polypeptide segment and the other part is not. In some embodiments, the non-membrane bound part is free in solution. In some embodiments, the non-membrane bound part is associated with the membrane through a tether. In some embodiments, the tether is through a glycophosphatidylinositol (GPI). In this embodiment, the non-membrane bound part includes a GPI signal sequence on its C-terminal end. In some embodiments, each part has a side-CAR element and the side-CAR elements associate to form a functional CAR or DE-CAR after a binding interaction primes the Side-CARs to associate. In some embodiments, an extracellular element of the CAR or DE-CAR binds to the target antigen which causes a conformational change in the extracellular element allowing it to associate with other parts of the CAR or DE-CAR. In some embodiments, the molecule that brings the two parts together is an antibody. In some embodiments, the molecule that causes the association of the two parts is a small molecule.

In some embodiments, the invention relates to a eukaryotic cell comprising a nucleic acid encoding Smart CAR(s), DE-CAR(s), Smart-DE-CAR(s), and/or Side-CARs of the invention. In some embodiments, the eukaryotic cell comprises an expression vector with nucleic acids encoding Smart CAR(s), DE-CAR(s), Smart-DE-CAR(s), and/or Side-CARs of the invention. In some embodiments, the eukaryotic cell of the invention is a mammalian cell. In some embodiments, the eukaryotic cell is a human cell or a murine cell. In some embodiments, the eukaryotic cell is a cell within the hematopoietic lineage. In some embodiments, the eukaryotic cell is a T-lymphocyte, a natural killer cell, a B-lymphocyte, or a macrophage. In some embodiments, the eukaryotic cell of the invention has a desired amount of CAR, DE-CAR, and/or Side-CAR polypeptide(s). In some embodiments, the eukaryotic cell has a desired amount of CAR, DE-CAR, and/or Side-CAR polypeptide(s) on its surface. In some embodiments, the eukaryotic cell with the CAR, DE-CAR, and/or Side-CAR polypeptide(s) of the invention has a desired amount of activity. In some embodiments, the desired amount of activity yields a proliferative activity. In some embodiments, the desired amount of activity is an amount of target binding or an amount of an effector activity (e.g., target cell killing).

In some embodiments, the RNA control device is expressed in cis to the mRNA encoding the CAR, DE-CAR, and/or Side-CAR. In some embodiments, the RNA control device is expressed in trans to the mRNA encoding the CAR, DE-CAR, and/or Side-CAR. In some embodiments, the invention relates to a eukaryotic cell with Smart CAR(s), DE-CAR(s), Smart-DE-CAR(s), and/or Side-CARs that incorporates several independent, orthogonal RNA control devices that respond to different small molecule ligands. In some embodiments, the invention provides for a eukaryotic cell which incorporates a multiple of Smart CAR(s), DE-CAR(s), Smart-DE-CAR(s), and/or Side-CARs with similar or distinct target specificities. In some embodiments, the multiple Smart CAR(s), DE-CAR(s), Smart-DE-CAR(s), and/or Side-CARs in the eukaryotic cell respond to a distinct set of small molecule ligands. In some embodiments, the multiple Smart CAR(s), DE-CAR(s), Smart-DE-CAR(s), and/or Side-CARs respond to different ligands, or the same ligands, or to overlapping sets of ligands.

In some embodiments, the invention relates to eukaryotic cells with custom CAR, custom DE-CAR, and/or custom Side-CAR polypeptide(s) expression. In this embodiment, the DE, RNA control device, and/or Side-CAR is/are used to customize the amount of CAR, DE-CAR and/or Side-CAR displayed on the surface of the eukaryotic cell. In some embodiments, the customized CAR, DE-CAR and/or Side-CAR display gives a desired level of activity against a target, and/or a desired level of proliferative activity when the eukaryotic cells with the customized CAR, DE-CAR and/or Side-CAR expression are placed into a subject. In some embodiments, the customized CAR, DE-CAR and/or Side-CAR expression gives a desired rate of target cell killing. In some embodiments, the customized CAR, DE-CAR and/or Side-CAR expression gives a desired rate of proliferation for the eukaryotic cell with the CAR, DE-CAR and/or Side-CAR polypeptide. In some embodiments, the customized CAR, DE-CAR and/or Side-CAR expression gives a desired rate of memory cell formation when the eukaryotic cell is an appropriate immune cell. In some embodiments, the customized CAR, DE-CAR and/or Side-CAR expression gives a desired amount of effector function in an appropriate eukaryotic cell, e.g., an immune cell.

In some embodiments, the invention relates to methods for making eukaryotic cells with customized levels of CAR, DE-CAR and/or Side-CAR expression using the Smart CAR(s), DE-CAR(s), Smart-DE-CAR(s), and/or Side-CARs of the invention. In some embodiments, the invention relates to methods for making eukaryotic cells with a desired amount of CAR, DE-CAR and/or Side-CAR polypeptide(s). In some embodiments, the invention relates to methods for making eukaryotic cells with Smart CAR(s), DE-CAR(s), Smart-DE-CAR(s), and/or Side-CARs that have a desired level of activity against a target. In some embodiments, the invention relates to methods of making eukaryotic cells with a desired activity level for target cell killing. In some embodiments, the invention relates to methods for making eukaryotic cells with Smart CAR(s), DE-CAR(s), Smart-DE-CAR(s), and/or Side-CARs that have a desired level of proliferation when placed in a subject. Other eukaryotic cell activities that may be customized include any activities useful in the treatment of disease, including, for example, rate of memory cell formation, release rate of cytokines, phagocytosis, binding of target, recruitment of innate myeloid or lymphoid cells, and epitope spreading.

In some embodiments, Smart CAR(s), DE-CAR(s), Smart-DE-CAR(s), and/or Side-CARs of the invention are introduced into a mammalian cell as a RNA(s) which encode a Smart CAR, DE-CAR, Smart-DE-CAR, and/or Side-CARs. In some embodiments the RNA which encodes the Smart CAR, DE-CAR, Smart-DE-CAR, and/or Side-CARs is a viral vector derived from a retrovirus, a lentivirus, an alphavirus, or another RNA virus, or an adenovirus or another DNA virus, or combinations thereof. In some embodiments, these vectors may harbor a library of Smart CAR, DE-CAR, Smart-DE-CAR, and/or Side-CAR devices encoded in conjunction with a reporter gene, and transduced cells that display desired Smart CAR, DE-CAR, Smart-DE-CAR, and/or Side-CAR behavior can be isolated based on activity and subject to further rounds of refinement. In some embodiments, the RNA encoding the Smart CAR, DE-CAR, Smart-DE-CAR, and/or Side-CAR is the reverse-complement strand (sometimes also called the antisense strand). In some embodiments, the RNA is derived from a retrovirus vector, lentivirus vector, alphavirus vector, or other RNA virus vector, and the RNA encoding the Smart CAR, DE-CAR, Smart-DE-CAR, and/or Side-CAR is the reverse complement (or antisense strand) relative to the + strand (or sense strand) of these RNA virus vectors, such that the Smart CAR, DE-CAR, Smart-DE-CAR, and/or Side-CAR is transcribed in the reverse-complement orientation during viral genome synthesis and packaging.

In some embodiments, the polynucleotide encoding the Smart CAR, DE-CAR, Smart-DE-CAR, and/or Side-CAR is/are integrated into a chromosome of the eukaryotic cell. In some embodiments, the polynucleotide encoding the Smart CAR, DE-CAR, Smart-DE-CAR, and/or Side-CAR is present in the eukaryotic cell extra-chromosomally. In some embodiments, the polynucleotide encoding the Smart CAR, DE-CAR, Smart-DE-CAR, and/or Side-CAR is integrated using a genome editing enzyme (CRISPR, TALEN, Zinc-Finger nuclease), and appropriate nucleic acids (including nucleic acids encoding the Smart CAR, DE-CAR, the Smart-DE-CAR, and/or Side CAR). In an embodiment, the genome editing enzymes and nucleic acids integrate the nucleic acid encoding the Smart CAR, DE-CAR, Smart-DE-CAR, and/or Side-CAR at a genomic safe harbor site, such as, for example, the CCR5, AAVS1, human ROSA26, or PSIP1 loci. In some embodiments, the eukaryotic cell is a human T-lymphocyte and the nucleic acid encoding the Smart CAR, DE-CAR, Smart-DE-CAR, and/or Side-CAR is integrated at the CCR5 or PSIP1 loci.

In some embodiments, the invention provides methods for selecting RNA aptamers with high specificity and selectivity for selected small molecule ligands. In some embodiments, the invention provides methods for increasing higher sensitivity, selectivity, or both to a target ligand of RNA control devices, achieved through the use of bacteriophage in live culture. In some embodiments, the invention provides methods for increasing higher sensitivity, selectivity, or both to a target ligand of RNA control devices, achieved through the use of replication-competent murine retrovirus or lentivirus in murine cell culture. In some embodiments, the invention provides methods for combining RNA aptamers with ribozymes, yielding a RNA control device. In some embodiments, the invention provides methods for incorporating RNA control devices into plant, bacterial or mammalian cells.

DETAILED DESCRIPTION OF THE INVENTION

Figure 1:
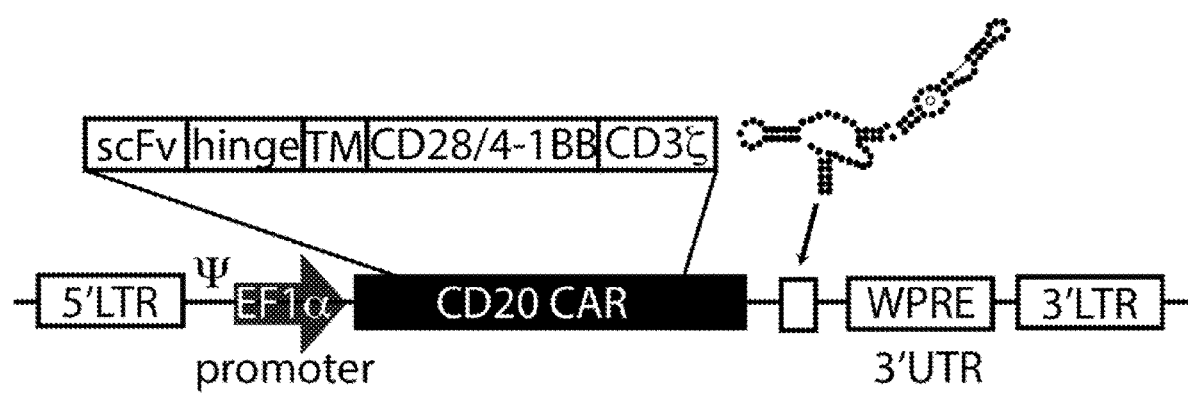
FIG. 1 provides a schematic diagram of a chimeric antigen receptor—RNA control device (Smart CAR).
Figure 2:
FIG. 2 provides a schematic diagram of a chimeric antigen receptor—Destabilizing Element (DE-CAR).
Figure 3:
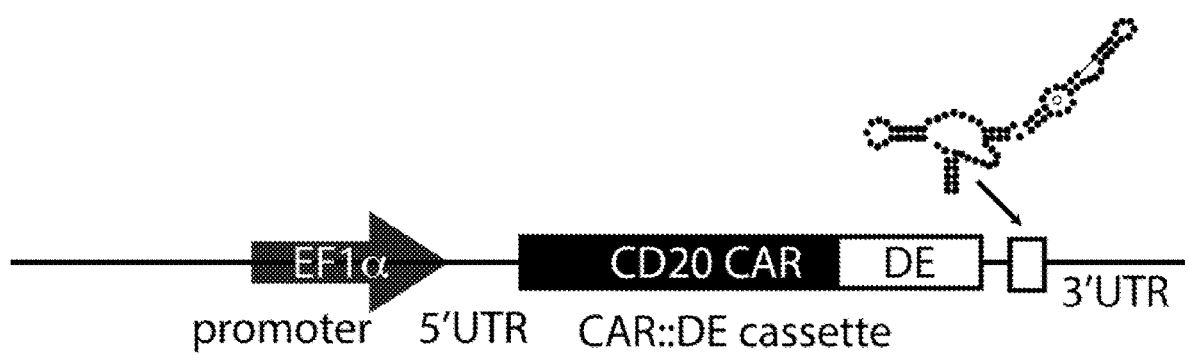
FIG. 3 provides a schematic diagram of a chimeric antigen receptor—Destabilizing Element—RNA control device (Smart-DE-CAR).

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. Numerical limitations given with respect to concentrations or levels of a substance are intended to be approximate, unless the context clearly dictates otherwise. Thus, where a concentration is indicated to be (for example) 10 µg, it is intended that the concentration be understood to be at least approximately or about 10 µg.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

As used herein, an "actuator element" is defined to be a domain that encodes the system control function of the RNA control device. In some embodiments, the actuator domain encodes the gene-regulatory function.

As used herein, an "antibody" is defined to be a protein functionally defined as a ligand-binding protein and structurally defined as comprising an amino acid sequence that is recognized by one of skill as being derived from the variable region of an immunoglobulin. An antibody can consist of one or more polypeptides substantially encoded by immunoglobulin genes, fragments of immunoglobulin genes, hybrid immunoglobulin genes (made by combining the genetic information from different animals), or synthetic immunoglobulin genes. The recognized, native, immunoglobulin genes include the kappa, lambda, alpha, gamma, delta, epsilon and mu constant region genes, as well as myriad immunoglobulin variable region genes and multiple D-segments and J-segments. Light chains are classified as either kappa or lambda. Heavy chains are classified as gamma, mu, alpha, delta, or epsilon, which in turn define the immunoglobulin classes, IgG, IgM, IgA, IgD and IgE, respectively. Antibodies exist as intact immunoglobulins, as a number of well characterized fragments produced by digestion with various peptidases, or as a variety of fragments made by recombinant DNA technology. Antibodies can derive from many different species (e.g., rabbit, sheep, camel, human, or rodent, such as mouse or rat), or can be synthetic. Antibodies can be chimeric, humanized, or humaneered. Antibodies can be monoclonal or polyclonal, multiple or single chained, fragments or intact immunoglobulins.

As used herein, an "antibody fragment" is defined to be at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either $V_L$ or $V_H$), camelid VHH domains, and multi-specific antibodies formed from antibody fragments. The term "scFv" is defined to be a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

As used herein, an "antigen" is defined to be a molecule that provokes an immune response. This immune response may involve either antibody production, or the activation of specific immunologically-competent cells, or both. The skilled artisan will understand that any macromolecule, including, but not limited to, virtually all proteins or peptides, including glycosylated polypeptides, phosphorylated polypeptides, and other post-translation modified polypeptides including polypeptides modified with lipids, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be synthesized or can be derived from a biological sample, or can be a macromolecule besides a polypeptide. Such a biological sample can include, but is not limited to a tissue sample, a tumor sample, a cell or a fluid with other biological components.

As used herein, an "antisense RNA" is defined to be a ribonucleic acid that is the reverse-complement of a target nucleic acid sequence, and under physiological conditions, is capable of hybridization to its cognate target sequence.

As used herein, an "aptamer" is defined to be a nucleic acid sequence that interacts with a ligand under normal physiological conditions.

As used herein, the terms "Chimeric Antigen Receptor" and the term "CAR" are used interchangeably. As used herein, a "CAR" is defined to be a fusion protein comprising antigen recognition moieties and cell-activation elements.

As used herein, a "CAR T-cell" or "CAR T-lymphocyte" are used interchangeably, and are defined to be a T-cell containing the capability of producing CAR polypeptide, regardless of actual expression level. For example a cell that is capable of expressing a CAR is a T-cell containing nucleic acid sequences for the expression of the CAR in the cell.

As used herein, a "costimulatory element" or "costimulatory signaling domain" or "costimulatory polypeptide" are defined to be the intracellular portion of a costimulatory polypeptide. A costimulatory polypeptide can be represented in the following protein families: TNF receptor proteins, Immunoglobulin-like proteins, cytokine receptors, integrins, signaling lymphocytic activation molecules (SLAM proteins), and activating natural killer cell receptors. Examples of such polypeptides include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, MyD88, and the like.

As used herein, a "destabilizing element" or a "DE" or a "Degron" are used interchangeably, and are defined to be a polypeptide sequence that is inducibly resistant or susceptible to degradation in the cellular context by the addition or subtraction of a ligand, and which confers this stability modulation to a co-translated polypeptide to which it is fused in cis.

As used herein, an "effective amount" or "therapeutically effective amount" are used interchangeably, and defined to be an amount of a compound, formulation, material, or composition, as described herein effective to achieve a particular biological result.

As used herein, an "epitope" is defined to be the portion of an antigen capable of eliciting an immune response, or the portion of an antigen that binds to an antibody. Epitopes can be a protein sequence or subsequence that is recognized by an antibody.

As used herein, an "expression vector" and an "expression construct" are used interchangeably, and are both defined to be a plasmid, virus, or other nucleic acid designed for protein expression in a cell. The vector or construct is used to introduce a gene into a host cell whereby the vector will interact with polymerases in the cell to express the protein encoded in the vector/construct. The expression vector and/or expression construct may exist in the cell extrachromosomally or integrated into the chromosome. When integrated into the chromosome the nucleic acids comprising the expression vector or expression construct will be an expression vector or expression construct.

As used herein, an "extracellular element" is defined as the antigen binding or recognition element of a Chimeric Antigen Receptor.

As used herein, a "helix-slipping mechanism" is defined to be an information transmission mechanism that is based on an element that functions through a helix-slipping event. Such a helix-slipping event uses a communication module (or helix-slipping element) within the general transmission region of the sensor element (e.g., the base stem of the aptamer) to result in disruption or restoration of the regulatory element in response to restoration of the sensor element.

As used herein, a "hematopoietic cell" is defined to be a cell that arises from a hematopoietic stem cell. This includes but is not limited to myeloid progenitor cells, lymphoid progenitor cells, megakaryocytes, erythrocytes, mast cells, myeloblasts, basophils, neutrophils, eosinophils, macrophages, thrombocytes, monocytes, natural killer cells, T lymphocytes, B lymphocytes and plasma cells.

As used herein, an "information transmission element" refers to a nucleic acid that transmits information between the sensor element and the regulatory element.

As used herein, an "intracellular element" is defined as the portion of a Chimeric Antigen Receptor that resides on the cytoplasmic side of the eukaryotic cell's cytoplasmic membrane, and transmits a signal into the eukaryotic cell. The "intracellular signaling element" is that portion of the intracellular element which transduces the effector function signal which directs the eukaryotic cell to perform a specialized function.

As used herein, a "regulatory element" is defined to be a nucleic acid that encodes the system control function of the RNA control device. The regulatory element has an RNA sequence that produces a distinct behavior in an RNA control device in response to ligand binding. Examples of regulatory elements include ribozymes, antisense RNA, RNAi, siRNA, shRNA, RNase III substrates, splicing elements, ribosome binding sites, IRES sequences, transcription terminators, attenuators, and other RNA secondary structures that regulate polypeptide expression.

As used herein, "reverse-complement strand" or "RNA virus (−) strand" are defined to be the complementary polynucleotide strand or the antisense strand to the (+) strand or sense strand of an RNA virus.

As used herein, a "ribozyme" is defined to be a natural or engineered ribonucleic acid capable of performing enzymatic catalysis. Examples of natural ribozymes are the hepatitis delta ribozyme, hairpin ribozymes, hammerhead ribozymes, varkud satellite ribozymes, and glmS ribozyme.

As used herein, a "RNA control device" is defined to be an RNA molecule that can adopt different structures and behaviors that correspond to different gene regulatory activities.

As used herein, a "RNase III substrate" is defined to be an RNA sequence motif that is recognized and cleaved by an endoribonuclease of the RNase III family.

As used herein, a "RNAi substrate" is defined to be an RNA sequence that is bound and/or cleaved by a short interfering RNA (siRNA) complexed to an effector endonuclease of the Argonaute family.

As used herein, a "RNA virus (+) strand" is defined to be a polynucleotide of the sense strand encoding an element of an RNA virus.

As used herein, a "sensor element" is defined to be a nucleic acid that that can bind a ligand. Ligand binding by the sensor element changes the activity of the regulatory element of the RNA control device.

As used herein, a "single chain antibody" (scFv) is defined as an immunoglobulin molecule with function in antigen-binding activities. An antibody in scFv (single chain fragment variable) format consists of variable regions of heavy ($V_H$) and light ($V_L$) chains, which are joined together by a flexible peptide linker.

As used herein, a "strand-displacement element" refers to a subset of information transmission elements that act through a strand-displacement mechanism.

As used herein, a "T-lymphocyte" or T-cell" is defined to be a hematopoietic cell that normally develops in the thymus. T-lymphocytes or T-cells include, but are not limited to, natural killer T cells, regulatory T cells, helper T cells, cytotoxic T cells, memory T cells, gamma delta T cells and mucosal invariant T cells.

As used herein, a "transcription terminator" is defined to be a nucleic acid sequence present on DNA and/or nascently synthesized RNA that signals the termination of RNA elongation by RNA polymerases.

As used herein, "transfected" or "transformed" or "transduced" are defined to be a process by which exogenous nucleic acid is transferred or introduced into a host cell. A "transfected" or "transformed" or "transduced" cell is one which has been transfected, transformed or transduced with exogenous nucleic acid. The cell includes the primary subject cell and its progeny.

As used herein, a "transmembrane element" is defined as the element between the extracellular element and the intracellular element. A portion of the transmembrane element exists within the cell membrane.

Destabilizing Elements

Destabilizing elements (DE) are stability-affecting polypeptides capable of interacting with a small-molecule ligand, the presence, absence, or amount of which ligand is used to modulate the stability of the DE-polypeptide of interest. In some embodiments, the polypeptide of interest is an immunomodulatory polypeptide. In some embodiments, the polypeptide of interest is a CAR. In some embodiments, binding of ligand by a DE-CAR reduces the degradation rate of the DE-CAR polypeptide in the eukaryotic cell. In some embodiments, binding of ligand by the DE-CAR increases the degradation rate of the DE-CAR in the eukaryotic cell.

In some embodiments, the DE is derived from a naturally-occurring ligand binding protein. In some embodiments, the ligand binding protein is a variant of the FKBP protein. In some embodiments, the variant FKBP polypeptide has one or more of the following substitutions: F15S, V24A, H25R, F36V, E60G, M66T, R71G, D100G, D100N, E102G, K105I, and L106P from SEQ ID NO: 1. In some embodiments, the variant FKBP has the polypeptide sequence of SEQ ID NOS: 2 or 3. In some embodiments, the variant FKBP polypeptide has the polypeptide TRGVEEVAEGV-VLLRRRGN (SEQ ID NO: 4) fused to the C-terminus of the FKBP. In some embodiments, the variant FKBP ligand is Shield 1, or a small molecule structurally related to rapamycin. In some embodiments, binding of ligand to the variant FKBP polypeptide in the DE-CAR stabilizes the DE-CAR and reduces the degradation rate of the DE-CAR in the eukaryotic cell. In some embodiments binding of ligand to the variant FKBP polypeptide in the DE-CAR destabilizes the DE-CAR and increases the degradation rate of the DE-CAR in the eukaryotic cell. Examples of variant FKBP nucleic acids and polypeptides are described in US published patent application 20120178168 A1 published on Jul. 12, 2012, which is hereby incorporated by reference in its entirety for all purposes.

In some embodiments, the ligand binding protein is a variant of the DHFR protein. In some embodiments, the variant DHFR polypeptide has one or more of the following substitutions: H12L, H12Y, N18T, A19V, M42T, I61F, T68S, R98H, Y100I, F103L, F103S, H114R, and G121V from SEQ ID NO: 5. In some embodiments, the variant DHFR has the polypeptide sequence of SEQ ID NOS: 6 or 7. In some embodiments, the variant DHFR polypeptide has one or more of the following groups of substitutions: H12L/Y100I, H12Y/Y100I, N18T/A19V, M42T/H114R, I61F/T68S, and R98H/F103S from SEQ ID NO: 5. In some embodiments, the variant DHFR ligand is trimethoprim, or a structurally related variant of trimethoprim. In some embodiments, binding of ligand to the variant DHFR polypeptide in the DE-CAR reduces the degradation rate of the DE-CAR in the eukaryotic cell. In some embodiments binding of ligand to the variant DHFR polypeptide in the DE-CAR increases the degradation rate of the DE-CAR in the eukaryotic cell. Examples of variant DHFR nucleic acids and polypeptides are described in US published patent application 20120178168 A1 published on Jul. 12, 2012, which is hereby incorporated by reference in its entirety for all purposes.

In some embodiments, the ligand binding protein is an estrogen receptor binding domain (ERBD) with a degron fused to the C-terminus of the ERBD (a variant ERBD). In some embodiments, the ERBD is derived from SEQ ID NO: 8 or 9. In some embodiments, a "degron" is an amino acid sequence that interacts with the cellular protein degradation machinery and specifies degradation of itself and any fusion protein of which it is a part. In some embodiments, the degron may be, for example, RRRG; (SEQ ID NO: 10), the bacterial YALAA peptide (SEQ ID NO: 11), the yeast CL1 degron, RRRGN (SEQ ID NO: 12), where N is an amino acid. In some embodiments, a peptide RRRG (SEQ ID NO: 10), optionally having a fifth residue is contemplated. In some embodiments, the ligand for the variant ERBD is CMP8 (9a-(4-Chlorobenzyl)-7-hydroxy-4-[4-(2-piperidin-1-yletoxy)phenyl]-1,2,9-, 9a-tetrahydro-3H-fluoren-3-one), 4-hydroxytamoxifen, fulvestrant or raloxifene. In some embodiments, the variant ERBD has a spacer peptide between the estrogen receptor binding domain and the degron. In some embodiments, the spacer is between 2-20, 4-20, 4-18, 4-16, 4-14, 4-12, 4-10, 4-8, 6-8 or 8 amino acid residues. In some embodiments, the variant ERBD has a polypeptide having at least about 60%, 70%, 80%, 85%, 90%, or 95% sequence identity to KHKILHRLLQDSS (SEQ ID NO: 13), wherein this polypeptide is located between the spacer and the degron, or between the ERBD and the degron. Examples of variant ERBD nucleic acids, polypeptides, and ligands are described in published US patent application 20140255361, which is hereby incorporated by reference in its entirety for all purposes.

In some embodiments, the DE is derived from phototropin 1 of *Avena sativa* (AsLOV2). In some embodiments, the DE is an AsLOV2 (SEQ ID NO: 14) that has a degron attached to the C-terminus of phototropin 1 (a variant AsLOV2). In some embodiments, the degron fused to the C-terminus of phototropin 1 is RRRG (SEQ ID NO: 9) or RRRGN (SEQ ID NO: 11). In some embodiments, the variant AsLOV2 includes one or more of the amino acid substitutions: V416A, V416I, N482K, N482R, D522E, D522A, G528A, V529N, I532A, and N538E (positions 14, 80, 120, 126, 127, 130, and 136, respectively, of SEQ ID NO: 14). In some embodiments, the variant AsLOV2 is SEQ ID NOS: 15 or 16 and the variant AsLOV2 is fused to a degron at the C-terminus. When these DE's are exposed to blue light the degron at the C-terminus is exposed and degradation of the DE-polypeptide of interest is increased. In some embodiments, a variant AsLOV2 is fused with a CAR to make a DE-CAR that is regulated by blue light.

Examples of variant AsLOV2 DEs are described in Bonger et al., ACS Chem. Biol. 2014, vol. 9, pp. 111-115, and Usherenko et al., BMC Systems Biology 2014, vol. 8, pp. 128-143, which are incorporated by reference in their entirety for all purposes.

Other DEs can be derived from other ligand binding polypeptides by fusing in frame a nucleic acid encoding the ligand binding polypeptide with a nucleic acid encoding a reporter. This construct is mutagenized by well-known methods, and then mutants with increased or decreased reporter activity in response to ligand binding are identified by a selection or screening. In some embodiments, variants obtained in a first round of mutagenesis and selection/screening are further mutagenized using random mutagenesis and/or creation of combinatorial libraries of the amino acid substitutions obtained in the first round of mutagenesis and/or substitution of other amino acids at the positions identified in the first round of mutagenesis. In some embodiments, the reporter polypeptide is a light emitting polypeptide such as green fluorescent polypeptide (GFP). In some embodiments, the reporter polypeptide can be used in a selection such as, for example, a reporter polypeptide that provides a cell with antibiotic resistance or the ability to grow in a certain nutrient environment or the ability to make a certain essential nutrient (e.g., the enzyme DHFR can be used in selection schemes with certain mammalian cell lines).

Other DEs can be derived from other ligand binding polypeptides using a degron as described above for ERBD. In some embodiments, a degron is fused to the C-terminus of the ligand binding polypeptide. In some embodiments, the degron is fused to the N-terminus of the ligand binding polypeptide. In some embodiments, the ligand binding polypeptide is a ligand binding domain derived from the ligand binding polypeptide, or is some other truncated form of the ligand binding polypeptide that has the ligand binding property. In some embodiments, a nucleic acid encoding the ligand binding domain fused to a degron is fused in frame with a nucleic acid encoding a reporter. This construct is mutagenized by well-known methods, and then mutants with increased or decreased reporter activity in response to ligand binding are identified by a selection or screening. In some embodiments, variants obtained in a first round of mutagenesis and selection/screening are further mutagenized using random mutagenesis and/or creation of combinatorial libraries of the amino acid substitutions obtained in the first round of mutagenesis and/or substitution of other amino acids at the positions identified in the first round of mutagenesis.

Other ligand binding polypeptides from which variants can be made for use as DEs, include for example, enzymes, antibodies or antibody fragments or antibody fragments engineered by recombinant DNA methods with the variable domain, ligand binding receptors, or other proteins. Examples of enzymes include bromodomain-containing proteins, FKBP variants, or prokaryotic DHFR variants. Examples of receptor elements useful in making DEs include: variant ERBD, or other receptors that have ligands which are nontoxic to mammals, especially humans.

In some embodiments, the ligand(s) for the DE are selected for optimization of certain attributes for therapeutic attractiveness. These attributes include, specificity to the target DE, affinity to the DE, bioavailability, stability, commercial availability, cost, available related chemical, bio-orthogonality, or combinations thereof. In some embodiments, the ligands are permeable to the plasma membrane, or are transported across the plasma membrane of a eukaryotic cell. In some embodiments, the ligand is orally dosable to a subject. In some embodiments, the ligand is inert (a pro-ligand) and is converted to the active ligand by, for example, chemical means, electromagnetic radiation, or metabolism by normal flora or the subject to produce the active ligand. In some embodiments, the ligand has a serum half-life greater than 1 hour, 2 hours, 4 hours, 6 hours, 8 hours, 12 hours, 24 hours, 48 hours, 96 hours or more. In some embodiments, the ligand has a serum half-life less than 96 hours, 48 hours, 24 hours, 18 hours, 12 hours, 10 hours, 8 hours, 6 hours, 4 hours, 2 hours or 1 hour or less. In some embodiments the ligand has a serum half-life between 1 and 96 hours, between 2 and 48 hours, between 8 and 36 hours, between 10 and 28 hours, between 12 and 24 hours, between 12 and 48 hours, between 8 and 48 hours or between 16 and 18 hours. In some embodiments, the ligand can cross the blood-brain barrier. In some embodiments, the ligand is small and lipophilic. In some embodiments, the ligand cannot normally exist in human bodies or be introduced by normal diet. In some embodiments, the affinity, as measured by Kd, of the ligands to the target DE is less than 1M, 500 mM, 100 mM, 50 mM, 20 mM, 10 mM, 5 mM, 1 mM, 500 µM, 100 µM, 50 µM, 20 µM, 10 µM, 5 µM, 1 µM, 500 nM, 100 nM, 50 nM, 20 nM, 10 nM, 5 nM, 4 nM, 3 nM, 2 nM, 1 nM, 0.5 nM, 0.1 nM or less. In some embodiments, the affinity, as measured by Kd, of the ligands to the target DE is between 1M and 1 pM, between 1 mM and 1 nM, between 100 uM and 1 nM, between 10 uM and 1 nM, between 10 uM and 10 nM, between 10 uM and 100 nM, between 10 uM and 1 uM and between 50 uM and 5 uM, between 1 uM and 500 nM. In some embodiments the ligand is a protein. In some embodiments, the ligand is a small molecule. In some embodiments, the ligand is a nucleic acid.

RNA Control Devices

In some embodiments, the Ribonucleic acid (RNA) control devices of the invention exhibit tunable regulation of gene expression, design modularity, and target specificity. The RNA control devices of the invention can act to rewire information flow through cellular networks and reprogram cellular behavior in response to changes in the cellular environment. In regulating polypeptide expression, the RNA control devices of the invention can serve as synthetic cellular sensors to monitor temporal and spatial fluctuations in the levels of diverse input molecules. RNA control devices represent powerful tools for constructing ligand-controlled gene regulatory systems tailored to modulate the expression of CAR, DE-CAR, and/or Side-CAR polypeptides of the invention in response to specific effector molecules enabling RNA regulation of target CAR, DE-CAR, and/or Side-CAR constructs in various living systems.

The RNA control devices of the invention may be either trans-acting or cis-acting. By trans-acting, it is meant that the RNA control device exerts its ligand-dependent activity on a molecule, e.g. another nucleic acid, that is different from the RNA control device, e.g. not linked through a phosphodiester (or equivalent) backbone linker, and even more preferably not covalently linked to the RNA control device at all. By cis-acting, it is meant that the RNA control device exerts its ligand-dependent activity on the same contiguous nucleic acid, i.e., a nucleic acid that is covalently linked to the RNA control device, e.g., through a phosophodiester (or equivalent) backbone linker.

In some embodiments, the RNA control devices of the invention comprise a regulatory element and a sensor element. In some embodiments, the RNA control devices of the invention comprise a single element with both a regulatory and sensory function. In some embodiments, the RNA control devices of the invention comprise a regulatory function and a sensory function. In some embodiments, the RNA control devices of the invention comprise a regulatory element, a sensor element, and an information transmission element (ITE) that functionally couples the regulatory element and the sensor element. In some embodiments, the ITE of the subject invention is based on, for example, a strand-displacement mechanism, an electrostatic interaction, a conformation change, or a steric effect. In some embodiments, the sensing function of the RNA control device leads to a structural change in the RNA control device, leading to altered activity of the acting function. Some mechanisms whereby these structural changes can occur include steric effects, hydrophobicity driven effects (log p), electrostatically driven effects, nucleotide modification effects (such as methylation, pseudouradination, etc.), secondary ligand interaction effects and other effects. In some embodiments, a strand-displacement mechanism uses competitive binding of two nucleic acid sequences (e.g., the competing strand and the RNA control device strand) to a general transmission region of the RNA control device (e.g., the base stem of the aptamer) to result in disruption or restoration of the regulatory element in response to ligand binding to the sensor element.

In some embodiments, the sensor element-regulated nucleic acids is designed such that it can adopt at least two distinct conformations. In one conformation, the sensor element is capable of binding to a ligand, and the regulatory element may be in one activity state (e.g., more active state or less active state). In the other conformation, the sensor element is incapable of binding to the ligand, and regulatory element may be in another activity state. The conformation change of the sensor element may be transmitted through the information transmission element to the coupled regulatory element, so that the regulatory element adopts one of the two activity states depending on whether the sensor element can or cannot bind the ligand.

In some embodiments, the aptamer-regulated nucleic acid platform is fully modular, enabling ligand response and regulatory function (e.g., transcript targeting) to be engineered by swapping elements within the subject regulated nucleic acid. This provides a platform for the construction of tailor-made sensor element regulated nucleic acids for a variety of different ligands. Ligand binding of the sensor element in sensor-regulated nucleic acids is designed separately from the targeting capability of the regulatory element by swapping only the sensor element. Likewise, the targeting capability of the regulatory element can be designed separately from the ligand binding of the sensor element by swapping the regulatory element so that a different gene or molecule is targeted without affecting the sensor element. Thus, the subject sensor element-regulated nucleic acids present a powerful, flexible method of tailoring spatial and temporal gene expression in both natural and engineered contexts.

In some embodiments, the RNA control devices are cis-acting RNA sequences that regulate the production of cognate protein encoded by a messenger RNA (mRNA). In some embodiments RNA control devices comprise RNA with sequences that enable direct or indirect binding of a ligand. In some embodiments, binding of a ligand to the RNA control device results in the level of protein product derived from the mRNA is augmented or diminished. In some embodiments, RNA control devices comprise riboswitches which are segments of mRNA that binds a small molecule.

An example of an RNA control device is the theophylline responsive switch, comprising an aptamer (a ligand binding component) and hammerhead ribozyme (gene regulating component) (Win and Smolke 2007 PNAS 104 (36): 14283-88, which is hereby incorporated by reference in its entirety for all purposes). Upon aptamer binding of theophylline, the ribozyme becomes inactive and enables the expression of the desired transgene. In the absence of binding of theophylline, the ribozyme self cleaves, leading to nuclease driven degradation of mRNA, inhibiting expression.

In some embodiments, the RNA control device comprises a sensor element and a regulatory element. In some embodiments the sensor element is an RNA aptamer. In some embodiments, the RNA control device comprises more than one sensor element. In some embodiments the regulatory element is a ribozyme. In some embodiments the ribozyme is a hammerhead ribozyme. In some embodiments, the ribozyme is a hairpin ribozyme, or a hepatitis delta virus (HDV) ribozyme, or a Varkud Satellite (VS) ribozyme, or a glmS ribozyme. In other embodiments the ribozyme is a ribozyme known in the art.

In some embodiments, the RNA control device is embedded within a nucleic acid that encodes a transgene. In some embodiments the transgene of interest encodes a chimeric antigen receptor or a DE-chimeric antigen receptor.

In some embodiments an RNA control device or devices are embedded within a DNA sequence. In some embodiments, the RNA control device is encoded for in messenger RNA. In some embodiments multiple RNA control devices are encoded in cis with a transgene-encoding mRNA. In some embodiments, the RNA control device is repeated. In some embodiments the nucleic acid that is used to encode the RNA control device is repeated. By including multiple RNA control devices, sensitivity and dose response may be tailored or optimized. In some embodiments multiple RNA control devices are included, with each RNA control device being specific for a different ligand. This embodiment can mitigate unintentional expression due to endogenously produced ligands that interact with the sensor element.

RNA Control Devices: Sensor Elements

In some embodiments, the sensor-regulated polynucleotides may further comprise a functional group or a functional agent, e.g., an intercalator or an alkylating agent. In some embodiments, the sensor-regulated polynucleotides may comprise synthetic or non-natural nucleotides and analogs (e.g., 6-mercaptopurine, 5-fluorouracil, 5-iodo-2'-deoxyuridine and 6-thioguanine) or may include modified nucleic acids. Exemplary modifications include cytosine exocyclic amines, substitution of 5-bromo-uracil, backbone modifications, methylations, and unusual base-pairing combinations. Additional analogs include at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

In some embodiments, the sensor element comprises an aptamer that responds to ligand binding to favor an allosteric change in the regulatory element that alters the ability of the regulatory element to interact with its target molecule. Ligand binding in this embodiment switches the regulatory element from "off" to "on," or vice versa. The sensor-element, therefore, acts as a switch that turns the activity of the RNA control device "off" and/or "on" in response to ligand binding. In some embodiments, the response of the sensor (aptamer) element to the ligand may also depend on the ligand identity and/or the amount or concentration of ligand exposed to the sensor (aptamer) element. In some embodiments, an aptamer may bind small molecules, such as drugs, metabolites, intermediates, cofactors, transition state analogs, ions, metals, nucleic acids, and toxins. Alternatively, an aptamer may bind natural and synthetic polymers, including proteins, peptides, nucleic acids, polysaccharides, glycoproteins, hormones, receptors and cell surfaces such as cell walls and cell membranes.

In some embodiments, an "aptamer" is a nucleic acid molecule, such as RNA or DNA that is capable of binding to a specific molecule with high affinity and specificity (Ellington et al., Nature 346, 818-22 (1990); and Tuerk et al., Science 249, 505-10 (1990), which are hereby incorporated by reference in their entirety for all purposes). Exemplary ligands that bind to an aptamer include, without limitation, small molecules, such as drugs, metabolites, intermediates, cofactors, transition state analogs, ions, metals, nucleic acids, and toxins. In some embodiments, aptamers may also bind natural and synthetic polymers, including proteins, peptides, nucleic acids, polysaccharides, glycoproteins, hormones, receptors and cell surfaces such as cell walls and cell membranes. In some embodiments, the binding of a ligand to an aptamer, which is typically RNA, causes or favors a conformational change in the regulatory element and alters its ability to interact with its target molecule. In some embodiments, ligand binding affects the regulatory element's ability to mediate gene inactivation, transcription, translation, or otherwise interfere with the normal activity of the target gene or mRNA.

Aptamers can be made that bind to a wide variety of molecules. Each of these aptamer molecules can be used as a modulator of gene expression using the methods of the invention. In some embodiments, organic molecules, nucleotides, amino acids, polypeptides, target features on cell surfaces, ions, metals, salts, saccharides, are used as ligands for making an aptamer that can specifically bind to the respective ligand. In some embodiments, organic dyes such as Hoechst 33258 are used as target ligands for in vitro aptamer selection (Werstuck and Green, Science 282:296-298 (1998), which is hereby incorporated by reference in its entirety for all purposes). In some embodiments, small organic molecules like dopamine, theophylline, sulforhodamine B, and cellobiose are used as ligands in the isolation of aptamers. In some embodiments, aptamers re isolated that bind to antibiotics such as kanamycin A, lividomycin, tobramycin, neomycin B, viomycin, chloramphenicol and streptomycin. For a review of aptamers that recognize small molecules, see Famulok, Science 9:324-9 (1999), which is hereby incorporated by reference in its entirety for all purposes.

In some embodiments, the RNA control device of the invention is comprised of RNA. In other embodiments of the invention, the RNA control device can instead be composed entirely of DNA, or partially of DNA, or partially of other nucleotide analogs. In some embodiments, translation is inhibited in vivo with an RNA control device comprised of RNA. Such aptamer-regulated RNAs are preferably introduced into a cell as a DNA that encodes the RNA control device such that transcription results in the RNA control device. In some embodiments, the RNA control device itself can be introduced into a cell.

In some embodiments, the binding affinity of the aptamer for its ligand must be sufficiently strong and the structure formed by the aptamer when bound to its ligand must be significant enough so as to switch an RNA control device of the invention between "on" and "off" states. In some embodiments, the association constant for the aptamer and associated ligand is preferably such that the ligand functions to bind to the aptamer and have the desired effect at the concentration of ligand obtained upon administration of the ligand to a subject. For in vivo use, for example, the association constant should be such that binding occurs well below the concentration of ligand that can be achieved in the serum or other tissue, preferably well below the concentration of ligand that can be achieved intracellularly since cellular membranes may not be sufficiently permeable to allow the intracellular ligand concentration to approach the level in the serum or extracellular environment. In some embodiments, the required ligand concentration for in vivo use is also below that which could have undesired effects on the organism.

Ligands for RNA Control Devices

RNA control devices can be controlled via the addition of exogenous or endogenous ligands. In some embodiments, the ligands are selected for optimization of certain attributes for therapeutic attractiveness. These attributes include, specificity to the target RNA control device, affinity to the RNA control device, bioavailability, stability, commercial availability, cost, available related chemical, bio-orthogonality, or combinations thereof. In some embodiments, the ligands are permeable to the plasma membrane, or are transported across the plasma membrane of a eukaryotic cell. In some embodiments, the ligand is orally dosable to a subject. In some embodiments, the ligand is inert (a pro-ligand) and is metabolized by normal flora or the subject to produce the active ligand. In some embodiments, the ligand has a serum half-life greater than 1 hour, 2 hours, 4 hours, 6 hours, 8 hours, 12 hours, 24 hours, 48 hours, 96 hours or more. In some embodiments, the ligand has a serum half-life less than 96 hours, 48 hours, 24 hours, 18 hours, 12 hours, 10 hours, 8 hours, 6 hours, 4 hours, 2 hours or 1 hour or less. In some embodiments the ligand has a serum half-life between 1 and 96 hours, between 2 and 48 hours, between 8 and 36 hours, between 10 and 28 hours, between 12 and 24 hours, between 12 and 48 hours, between 8 and 48 hours or between 16 and 18 hours. In some embodiments, the ligand can cross the blood-brain barrier. In some embodiments, the ligand is small and lipophilic. In some embodiments, the ligand cannot normally exist in human bodies or be introduced by normal diet. In some embodiments, the affinity, as measured by Kd, of the ligands to the target RNA control device is less than 1M, 500 mM, 100 mM, 50 mM, 20 mM, 10 mM, 5 mM, 1 mM, 500 µM, 100 µM, 50 µM, 20 µM, 10 µM, 5 µM, 1 µM, 500 nM, 100 nM, 50 nM, 20 nM, 10 nM, 5 nM, 4 nM, 3 nM, 2 nM, 1 nM, 0.5 nM, 0.1 nM or less. In some embodiments, the affinity, as measured by Kd, of the ligands to the target DE is between 1M and 1 pM, between 1 mM and 1 nM, between 100 uM and 1 nM, between 10 uM and 1 nM, between 10 uM and 10 nM, between 10 uM and 100 nM, between 10 uM and 1 uM and between 50 uM and 5 uM, between 1 uM and 500 nM. In some embodiments the ligand is a protein. In some embodiments, the ligand is a small molecule. In some embodiments, the ligand is a nucleic acid.

In some embodiments, the ligand is a naturally occurring, secreted metabolite. For example, a ligand that is uniquely produced by a tumor, or present in the tumor microenvironment is the ligand for the sensor element and binding of this ligand to the sensor element changes the activity of the RNA control device. Thus the control device is responsive and controlled through chemical signaling or proximity to a tumor.

In some embodiments, the ligand is selected for its pharmacodynamic or ADME behavior. For example ligands may be preferentially localized to specific portions of the human anatomy and physiology. For example certain molecules are preferentially absorbed or metabolized in the gut, the liver, the kidney etc. In some embodiments the ligand is selected to demonstrate preferential pharmacodynamic behavior in a particular organ. For example, it would be useful to have a ligand that preferentially localizes to the colon for a colorectal carcinoma so that the peak concentration of the ligand is at the required site, whereas the concentrations in the rest of the body is minimized, preventing undesired, nonspecific toxicity. In some embodiments the ligand is selected to demonstrate non preferential pharmacodynamic behavior. For example, for disseminated tumors like hematological malignancies, it would be useful to have non variant concentration of the ligand throughout the body.

RNA Control Device Discovery Via Virus Assisted Continuous Evolution

Directed evolution has been used to derive wide libraries of biomolecules with desired properties. However limitations of the typical batch like process in laboratory evolution has limited the scope with which directed evolution can be used to rapidly and effectively create these biomolecules. Recently, a continuous technique for directed evolution, known as phage assisted continuous evolution (PACE) has been used to create novel RNA polymerase systems quickly (Esvelt et al., Nature, 472:499, 2011, which is hereby incorporated by reference in its entirety for all purposes). In some embodiments, the method of evolving desired RNA control devices relies on PACE.

In some embodiments, an RNA control device is operably linked to a nucleic acid necessary for reproduction of the virus, such that reproduction of the virus is controlled by the RNA control device. In some embodiments, the RNA control device binds a ligand that activates the RNA control device. In some embodiments, the RNA control device binds a ligand whereby the RNA control device is inhibited after ligand binding. In some embodiments, the RNA control device promotes reproduction of the virus. In some embodiments, the RNA control device inhibits reproduction of the virus. In some embodiments, growth of the virus in appropriate host cells and with appropriate levels of ligand for the RNA control device selects for (or screens for) RNA control devices with desired properties. In some embodiments, the viral nucleic acids encoding the RNA control device are replicated by an error prone polymerase. In some embodiments, the viral nucleic acids encoding the RNA control device are subject to other, well-known methods of mutagenesis to generate variants of the RNA control device. In some embodiments the method of evolving RNA control devices comprises the use of M13 phage libraries lacking the M13 P3 infectivity factor. Without wishing to be bound by theory it is believed that the RNA control devices are lightly mutagenized once per round and thus harbor subtle RNA control device variants that impact the expression of T7 RNA polymerase in the presence of the cognate ligand. Subsequently, T7 RNAP transcribes M13 P3 from an ectopic locus harbored by the infected E. coli host. High levels of P3 production directly correlates with M13 phage infectivity, thus M13 clones that harbor RNA control devices with the selected properties are subject to purifying selection over multiple rounds. In some embodiments the method comprises a non-classical bacteriophage PACE system. In some embodiments this non-classical bacteriophage PACE system comprises the use of an RNA phage of the Leviviridae family which harbors an RNA control device. In some embodiments this RNA phage is subject to multiple rounds of infection in the presence of the small molecule inhibitor of the RNA control device function. In some embodiments the assembled RNA control devices are placed within infectious bacteriophage and introduced into live bacterial cultures in a manner compatible with one or more implementations of PACE. Without wishing to be bound by theory, it is believed that the activity of the RNA control device is directly coupled to propagation and fitness of successive rounds of progeny phage infections. In some embodiments, the method of evolving RNA devices comprises the use of the canonical M13-based PACE system. In this embodiment, without wishing to be bound by theory, the M13 clones harboring RNA control device variants that are responsive to the cognate small molecule ligand are subject to multiple cycles of mutation and selection, yielding evolved RNA control devices that display desirable performance properties in bacteria. In some embodiments, the method for evolving an RNA control device comprises the use of an RNA phage of the Leviviridae family. In some embodiments, the RNA phage harboring an RNA control device is subject to multiple rounds of mutation via error prone genome copying and negative selection via genome cleavage, yielding evolved RNA control devices that display desirable performance properties in bacteria. In some embodiments, the method for evolving RNA control devices is a novel PACE system.

A number of other methods are well-known in the art for generating libraries of variants for directed evolution of the RNA control device. For example, EpPCR, which introduces random point mutations by reducing the fidelity of DNA polymerase in PCR reactions (Pritchard et al., J. Theor. Biol. 234:497-509 (2005) which is hereby incorporated by reference in its entirety for all purposes); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., Nucleic Acids Res. 32:e145 (2004); and Fujii et al., Nat. Protoc. 1:2493-2497 (2006), which are hereby incorporated by reference in their entirety for all purposes); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, Proc. Natl. Acad. Sci. U.S.A. 91:10747-10751 (1994); and Stemmer, Nature 370:389-391 (1994), which are hereby incorporated by reference in their entirety for all purposes); Staggered Extension (StEP), which entails template priming followed by repeated cycles of 2 step PCR with denaturation and very short duration of annealing/ extension (as short as 5 sec) (Zhao et al., Nat. Biotechnol. 16:258-261 (1998), which is hereby incorporated by reference in its entirety for all purposes); Random Priming Recombination (RPR), in which random sequence primers are used to generate many short DNA fragments complementary to different segments of the template (Shao et al., Nucleic Acids Res 26:681-683 (1998), which is hereby incorporated by reference in its entirety for all purposes).

RNA Control Devices: Regulatory Elements

In some embodiments, the regulatory element comprises a ribozyme, or an antisense nucleic acid, or an RNAi sequence or precursor that gives rise to a siRNA or miRNA, or an shRNA or precursor thereof, or an RNAse III substrate, or an alternative splicing element, or a transcription terminator, or a ribosome binding site, or an IRES, or a polyA site.

In some embodiments, the regulatory element of an RNA control device comprises an antisense sequence and acts through an antisense mechanism in modulating expression of a target gene. For instance, an RNA control device may comprise a regulatory element that comprises an antisense sequence for inhibiting expression of a target gene and an aptamer element that binds to a ligand. The binding of the ligand to the aptamer element causes a conformational change in the RNA control device that alters the ability of the antisense sequence of the regulatory element to inhibit expression of the target sequence.

In some embodiments, an RNA control device, for example, can be a component of an expression plasmid which, when transcribed in the eukaryotic cell, modulates expression of a target through the regulatory element. Alternatively, the RNA control device can be generated outside of the target cell, subsequently introduced into the target cell to modulate expression of the target. RNA control devices may be modified so that they are resistant to endogenous nucleases, e.g. exonucleases and/or endonucleases, and are therefore stable in vivo. Exemplary nucleic acid molecules for use in RNA control devices are phosphoramidate, phosphothioate and methylphosphonate analogs of DNA (see also U.S. Pat. Nos. 5,176,996; 5,264,564; and 5,256,775, which are hereby incorporated by reference in their entirety for all purposes). General approaches to constructing oligomers useful in antisense technology have been reviewed, for example, by van der Krol et al. (1988) Biotechniques 6:958-976; and Stein et al. (1988) Cancer Res 48:2659-2668, which are hereby incorporated by reference in their entirety for all purposes.

In some embodiments, the regulatory element of an RNA control device comprises a regulatory element that comprises an RNAi sequence and acts through an RNAi or miRNA mechanism in modulating expression of a target gene. For instance, an RNA control device may comprise a regulatory element that comprises a miRNA or siRNA sequence for inhibiting expression of a target gene and an aptamer element that binds to a ligand. The binding of the ligand to the aptamer element causes a conformational change in the aptamer-regulated nucleic acid that alters the ability of the miRNA or siRNA sequence of the regulatory element to inhibit expression of the target sequence. In some embodiments, a regulatory element comprises a miRNA or siRNA sequence that is between about 19 nucleotides and about 35 nucleotides in length, or preferably between about 25 nucleotides and about 35 nucleotides. In some embodiments, the regulatory element is a hairpin loop that may be processed by RNase III enzymes. As used herein, the term "RNAi" means an RNA-mediated mechanism for attenuating gene expression and includes small RNA-mediated silencing mechanisms. RNA-mediated silencing mechanisms include inhibition of mRNA translation and directed cleavage of targeted mRNAs. The sequence targeted by the regulatory element can be selected from untranscribed sequences that regulate transcription of a target gene at the genomic level.

In some embodiments, an RNAi construct contains a nucleotide sequence that hybridizes under the physiologic conditions of the cell to the nucleotide sequence of at least a portion of the mRNA transcript for the gene to be inhibited (i.e., the "target" gene). The double-stranded RNA only needs to be sufficiently similar to natural RNA for its ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may abolish cleavage of the target RNA. In contrast, nucleotides at the 3' end of the siRNA strand that is complementary to the target RNA do not significantly contribute to specificity of target recognition. However, certain miRNA designs, such as the mir-30 based miRNA designs, may feature a bulge of about a few nucleotides in the middle of the guide sequence.

In some embodiments, the subject RNAi constructs are "siRNAs." These nucleic acids are between about 19-35 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex or translation is inhibited. In a particular embodiment, the 21-23 nucleotides siRNA molecules comprise a 3' hydroxyl group.

In some embodiments, the subject RNAi constructs are "miRNAs." microRNAs (miRNAs) are small non-coding RNAs that direct post transcriptional regulation of gene expression through interaction with homologous mRNAs. miRNAs control the expression of genes by binding to complementary sites in target mRNAs. miRNAs are processed by nucleolytic cleavage from larger double-stranded precursor molecules. These precursor molecules are often hairpin structures of about 70 nucleotides in length, with 25 or more nucleotides that are base-paired in the hairpin. The RNase III-like enzymes Drosha and Dicer (which may also be used in siRNA processing) cleave the miRNA precursor to produce an miRNA. The processed miRNA is single-stranded and incorporates into a protein complex, termed RISC or miRNP. This RNA-protein complex targets a complementary mRNA. miRNAs inhibit translation or direct cleavage of target mRNAs. (Brennecke et al., Genome Biology 4:228 (2003); Kim et al., Mol. Cells. 19:1-15 (2005), which are hereby incorporated by reference in their entirety for all purposes).

In some embodiments, the regulatory element is a ribozyme. In some embodiments, the ribozyme self-cleaves its phosphate backbone in the presence of appropriate cofactors, such as divalent metals. The products of this intramolecular RNA cleavage yield a 2',3'-cyclic phosphate on the upstream cleavage fragment, and a 5'OH on the downstream cleavage fragment. An example of a self-cleaving ribozyme is a hammerhead ribozyme that cleaves the 3' untranslated region of the gene product mRNA. The ribozyme can be coupled to a sensor element that binds a ligand so that the ribozyme cleaves the mRNA either in the presence or absence of the ligand. Binding of the ligand can either induce ribozyme cleavage or inhibit ribozyme cleavage depending on the design of the RNA control device.

In some embodiments, the RNA control devices have multiple regulatory elements, and/or multiple sensor elements. In some embodiments, the multiple sensor elements recognize different ligands. In some embodiments, the multiple sensor elements have different effects on the regulatory element.

Chimeric Antigen Receptors

In some embodiments, chimeric antigen receptors (CARs) are fused proteins comprising an extracellular antigen-binding/recognition element, a transmembrane element that anchors the receptor to the cell membrane and at least one intracellular element. These CAR elements are known in the art, for example as described in patent application US20140242701, which is incorporated by reference in its entirety for all purposes herein. In some embodiments, the CAR of the invention is a recombinant polypeptide construct comprising at least an extracellular antigen binding element, a transmembrane element and an intracellular signaling element comprising a functional signaling element derived from a stimulatory molecule. In some embodiments, the stimulatory molecule is the zeta chain associated with the T cell receptor complex. In some embodiments, the cytoplasmic signaling element further comprises one or more functional signaling elements derived from at least one costimulatory molecule. In some embodiments, the costimulatory molecule is chosen from 4-1BB (i.e., CD137), CD27 and/or CD28. In some embodiments, the CAR comprises a chimeric fusion protein comprising an extracellular antigen recognition element, a transmembrane element and an intracellular signaling element comprising a functional signaling element derived from a stimulatory molecule. In some embodiments, the CAR comprises a chimeric fusion protein comprising an extracellular antigen recognition element, a transmembrane element and an intracellular signaling element comprising a functional signaling element derived from a co-stimulatory molecule and a functional signaling element derived from a stimulatory molecule. In some embodiments, the CAR comprises a chimeric fusion protein comprising an extracellular antigen recognition element, a transmembrane element and an intracellular signaling element comprising two functional signaling elements derived from one or more co-stimulatory molecule(s) and a functional signaling element derived from a stimulatory molecule. In some embodiments, the CAR comprises a chimeric fusion protein comprising an extracellular antigen recognition element, a transmembrane element and an intracellular signaling element comprising at least two functional signaling elements derived from one or more co-stimulatory molecule(s) and a functional signaling element derived from a stimulatory molecule. In some embodiments, the CAR comprises an optional leader sequence at the amino-terminus (N-ter) of the CAR fusion protein. In some embodiments, the CAR further comprises a leader sequence at the N-terminus of the extracellular antigen recognition element, wherein the leader sequence is optionally cleaved from the antigen recognition element (e.g., a scFv) during cellular processing and localization of the CAR to the cellular membrane.

Chimeric Antigen Receptor—Extracellular Element

In some embodiments, the "extracellular element capable of binding to an antigen" used for the CAR of the present invention is an element comprising an oligopeptide or polypeptide that can bind to a target antigen, and includes, for example, an antigen-binding domain of an antibody and a ligand-binding domain of a receptor. In some embodiments, this element binds to and interacts with an antigen, for example, an antigen present on a cell surface of a target cell, and thereby imparts specificity to a cell expressing a CAR. Particularly useful examples of the extracellular element in the present invention include extracellular elements derived from antibodies (H chain and L chain) and variable regions of a TCR (TCRα, TCRβ, TCRγ, TCR δ), CD8α, CD8β, CD11A, CD11B, CD11C, CD18, CD29, CD49A, CD49B, CD49D, CD49E, CD49F, CD61, CD41, and CD51. In some embodiments, the entire protein may be used effectively. In some embodiments, a domain capable of binding to an antigen or a ligand, for example, an extracellular domain of an antibody Fab fragment, an antibody variable region [V region of H chain (VH) and V region of L chain (VL)] or a receptor can be used. In some embodiments, a scFv can be used. In some embodiments, the extracellular element is selected to be from a polypeptide that is native to the species of the subject which will be administered the eukaryotic cell with the Smart CAR, DE-CAR, Smart-DE-CAR, and/or Side-CAR. In some embodiments, a portion of a domain can be used as long as it retains the ability to bind antigen.

As described in U.S. Pat. Nos. 5,359,046, 5,686,281 and 6,103,521 (which are hereby incorporated by reference in their entirety for all purposes), the extracellular element may be obtained from any of the wide variety of extracellular elements or secreted proteins associated with ligand binding and/or signal transduction. In some embodiments, the extracellular element is part of a protein which is monomeric, homodimeric, heterodimeric, or associated with a larger number of proteins in a non-covalent complex. In some embodiments, the extracellular element may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed or all or part of the hinge region may be removed.

In some embodiments, the extracellular element for the CAR of the present invention may be an extracellular element that binds to only one antigen or ligand, or an extracellular element that binds to two or more antigens or ligands. In some embodiments, Smart CAR(s), DE-CAR(s), Smart-DE-CAR(s), and/or Side-CARs of the invention comprise one extracellular element or two or more extracellular elements. In some embodiments, the Smart CAR, DE-CAR, Smart-DE-CAR, and/or Side CAR is a bispecific CAR and targets two different antigens. In some embodiments, the bispecific Smart CAR, DE-CAR, Smart-DE-CAR, and/or Side CAR controls an inhibitory CAR and an amplifying CAR, each addressable by different ligands. This embodiment provides positive and negative control over the activity of the eukaryotic cell. In some embodiments, the antigen-specific targeting regions of the Smart CAR, DE-CAR, Smart-DE-CAR, and/or Side CAR may be arranged in tandem and may be separated by linker peptides. In some embodiments, the antigens targeted by the Smart CAR, DE-CAR, Smart-DE-CAR, and/or Side CAR may be antigens on a diseased cell (such as a cancerous B-cell) or antigens that are expressed on separate cells that each contribute to a disease. In some embodiments, the antigens targeted by the Smart CAR, DE-CAR, Smart-DE-CAR, and/or Side CAR are antigens which are either directly or indirectly involved in the disease.

In some embodiments, the extracellular element can be selected from antibodies recognizing a target antigen or molecules interacting with the antigen. Examples of antigens include a viral antigen, a bacterial (particularly, infectious bacterial) antigen, a parasite antigen, a cell surface marker on a target cell related to a certain condition (e.g. a tumor antigen), and a surface molecule of an immunity-related cell.

The extracellular element can be any polypeptide that binds to the antigen including but not limited to a monoclonal antibody, a polyclonal antibody, a recombinant antibody, a human antibody, a humanized antibody, single chain antibodies, polyvalent antibodies, polyspecific antibodies, diabodies, and a functional fragment thereof, including but not limited to a single-domain antibody such as a heavy chain variable domain (VH), a light chain variable domain (VL) and a variable domain (VHH) of a camelid derived nanobody, and to an alternative scaffold known in the art to function as antigen binding domain, such as a recombinant fibronectin domain, and the like. In some embodiments, it is beneficial for the antigen binding element to be derived from the same species in which the CAR will ultimately be used. For example, for use in humans, it may be beneficial for the antigen binding element of the Smart CAR, DE-CAR, Smart-DE-CAR, and/or Side CAR to comprise human or humanized or humaneered or human chimeric residues for the antigen binding element of an antibody or antibody fragment.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), which are incorporated by reference in their entirety for all purposes). Another method uses a particular framework derived from the consensus sequence of all human antibodies of a particular subgroup of light or heavy chains. The same framework may be used for several different humanized antibodies (see, e.g., Nicholson et al. Mol. Immun. 34 (16-17): 1157-1165 (1997); Carter et al., Proc. Natl. Acad. Sci. USA, 89:4285 (1992); Presta et al., J. Immunol., 151:2623 (1993), which are incorporated herein by reference in their entirety for all purposes). In some embodiments, the framework region, e.g., all four framework regions, of the heavy chain variable region are derived from a $VH4_{-4-59}$ germline sequence. In one embodiment, the framework region can comprise, one, two, three, four or five modifications, e.g., substitutions, e.g., from the amino acid at the corresponding murine sequence. In one embodiment, the framework region, e.g., all four framework regions of the light chain variable region are derived from a $VK3_{-1-25}$ germline sequence. In one embodiment, the framework region can comprise, one, two, three, four or five modifications, e.g., substitutions, e.g., from the amino acid at the corresponding murine sequence.

A "humaneered" antibody refers to an engineered human antibody having a binding specificity of a reference antibody. A "humaneered" antibody for use in this invention has an immunoglobulin molecule that contains minimal sequence derived from a donor immunoglobulin. Typically, an antibody is "humaneered" by joining a DNA sequence encoding a binding specificity determinant (BSD) from the CDR3 region of the heavy chain of the reference antibody to human $V_H$ segment sequence and a light chain CDR3BSD from the reference antibody to a human $V_L$ segment sequence. A "BSD" refers to a CDR3-FR4 region, or a portion of this region that mediates binding specificity. A binding specificity determinant therefore can be a CDR3-FR4, a CDR3, a minimal essential binding specificity determinant of a CDR3 (which refers to any region smaller than the CDR3 that confers binding specificity when present in the V region of an antibody), the D segment (with regard to a heavy chain region), or other regions of CDR3-FR4 that confer the binding specificity of a reference antibody. Methods for humaneering are provided in US patent application publication no. 20050255552 and US patent application publication no. 20060134098 (which are incorporated by reference in their entirety for all purposes).

In some embodiments, there is provided a Smart CAR, DE-CAR, Smart-DE-CAR, and/or Side-CAR capable of binding to an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus.

In some embodiments, antigens specific for infectious diseases targeted by the Smart CAR(s), DE-CAR(s), Smart-DE-CAR(s), and/or Side-CARs of the invention include but are not limited to any one or more of anthrax toxin, CCR5, CD4, clumping factor A, cytomegalovirus, cytomegalovirus glycoprotein B, endotoxin, *Escherichia coli*, hepatitis B surface antigen, hepatitis B virus, HIV-1, Hsp90, Influenza A hemagglutinin, lipoteichoic acid, *Pseudomonas aeruginosa*, rabies virus glycoprotein, respiratory syncytial virus and TNF-α. Other antigens specific for infectious diseases will be apparent to those of skill in the art and may be used in connection with alternate embodiments of the invention.

In some embodiments, there is provided a Smart CAR, DE-CAR, Smart-DE-CAR, and/or Side CAR capable of binding to an antigen derived from a bacterial strain of *Staphylococci, Streptococcus, Escherichia coli, Pseudomonas*, or *Salmonella*. In some embodiments, a phagocytic immune cell is engineered with a Smart CAR, DE-CAR, Smart-DE-CAR, and/or Side CAR specific for these or other pathogenic bacteria. Such Smart CAR, DE-CAR, Smart-DE-CAR, and/or Side CAR engineered immune cells are useful in treating septicemia. Examples of bacterial pathogens that can be targeted by such Smart CAR(s), DE-CAR(s), Smart-DE-CAR(s), and/or Side-CARs include, *Staphylococcus aureus, Neisseria gonorrhoeae, Streptococcus pyogenes*, Group A *Streptococcus*, Group B *Streptococcus* (*Streptococcus agalactiae*), *Streptococcus pneumoniae*, and *Clostridium tetani*. In some embodiments, there is provided a Smart CAR, DE-CAR, Smart-DE-CAR, and/or Side CAR capable of binding to an antigen found on host cells infected with an infectious pathogen (e.g., a virus, a bacteria, a protozoan, or a fungus). Examples of bacterial pathogens that may infect host cells include, *Helicobacter pyloris, Legionella pneumophilia*, a bacterial strain of *Mycobacteria* sps. (e.g. *M. tuberculosis, M. avium, M. intracellulare, M. kansaii*, or *M. gordonea*), *Neisseria meningitides, Listeria monocytogenes, R. rickettsia, Salmonella* spp., *Brucella* spp., *Shigella* spp., or certain *E. coli* strains or other bacteria that have acquired genes with invasive factors. Examples of viral pathogens that may infect host cells include, Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus.

In some embodiments, there is provided a Smart CAR, DE-CAR, Smart-DE-CAR, and/or Side CAR capable of binding to a tumor antigen such as any one or more of 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD21, CD22, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, alpha 5β1-integrin, integrin αvβ3, MORAb-009, MS4A1, MUC1, mucin CanAg, N-glycolylneuraminic acid, NPC-1C, PDGF-Rα, PDL192, phosphatidylserine, prostatic carcinoma cells, RANKL, RON, ROR1, SCH 900105, SDC1, SLAMF7, TAG-72, tenascin C, TGF β2, TGF-β, TRAIL-R1, TRAIL-R2, tumor antigen CTAA16.88, VEGF-A, VEGFR-1, VEGFR2, 707-AP, ART-4, B7H4, BAGE, β-catenin/m, Bcr-abl, MN/C IX antibody, CAMEL, CAP-1, CASP-8, CD25, CDC27/m, CDK4/m, CT, Cyp-B, DAM, ErbB3, ELF2M, EMMPRIN, ETV6-AML1, G250, GAGE, GnT-V, Gp100, HAGE, HLA-A*0201-R170I, HPV-E7, HSP70-2M, HST-2, hTERT (or hTRT), iCE, IL-2R, IL-5, KIAA0205, LAGE, LDLR/FUT, MAGE, MART-1/melan-A, MART-2/Ski, MC1R, myosin/m, MUM-1, MUM-2, MUM-3, NA88-A, PAP, proteinase-3, p190 minor bcr-abl, Pml/RARα, PRAME, PSA, PSM, PSMA, RAGE, RU1 or RU2, SAGE, SART-1 or SART-3, survivin, TPI/m, TRP-1, TRP-2, TRP-2/INT2, WT1, NY-Eso-1 or NY-Eso-B or vimentin. Other antigens specific for cancer will be apparent to those of skill in the art and may be used in connection with alternate embodiments of the invention.

In some embodiments, antigens specific for inflammatory diseases are targeted by the Smart CAR(s), DE-CAR(s), Smart-DE-CAR(s), and/or Side-CARs of the invention including but not limited to any one or more of AOC3 (VAP-1), CAM-3001, CCL11 (eotaxin-1), CD125, CD147 (basigin), CD154 (CD40L), CD2, CD20, CD23 (IgE receptor), CD25 (.alpha. chain of IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, *Lama glama*, LFA-1 (CD11 a), MEDI-528, myostatin, OX-40, rhuMAb .beta.7, scleroscin, SOST, TGF β1, TNF-α or VEGF-A. Other antigens specific for inflammatory diseases will be apparent to those of skill in the art and may be used in connection with alternate embodiments of the invention.

In some embodiments, antigens specific for neuronal disorders targeted by the Smart CAR(s), DE-CAR(s), Smart-DE-CAR(s), and/or Side-CARs of the invention include but are not limited to any one or more of beta amyloid or MABT5102A. Other antigens specific for neuronal disorders will be apparent to those of skill in the art and may be used in connection with alternate embodiments of the invention.

In some embodiments, antigens specific for diabetes targeted by the Smart CAR(s), DE-CAR(s), Smart-DE-CAR(s), and/or Side-CARs of the invention include but are not limited to any one or more of L-1β or CD3. Other antigens specific for diabetes or other metabolic disorders will be apparent to those of skill in the art and may be used in connection with alternate embodiments of the invention.

In some embodiments, antigens specific for senescent cells are targeted by the CAR, DE-CAR, Smart-DE-CAR, and/or Side-CARs of the invention include but are not limited to any one or more of DEP1, NTAL, EBP50, STX4, VAMP3, ARMX3, B2MG, LANCL1, VPS26A, or PLD3. Other antigens specific for senescent cells will be apparent to those of skill in the art and may be used in connection with alternate embodiments of the invention. See, e.g., Althubiti et al., Cell Death and Disease vol. 5, p. e1528 (2014), which is incorporated by reference in its entirety for all purposes.

In some embodiments, antigens specific for cardiovascular diseases targeted by the Smart CAR(s), DE-CAR(s), Smart-DE-CAR(s), and/or Side-CARs of the invention include but are not limited to any one or more of C5, cardiac myosin, CD41 (integrin α-IIb), fibrin II, beta chain, ITGB2 (CD18) and sphingosine-1-phosphate. Other antigens specific for cardiovascular diseases will be apparent to those of skill in the art and may be used in connection with alternate embodiments of the invention.

Intracellular Element

In some embodiments, the intracellular element is a molecule that can transmit a signal into a cell when the extracellular element of the Smart CAR, DE-CAR, Smart-DE-CAR, and/or Side CAR binds to (interacts with) an antigen. In some embodiments, the intracellular signaling element is generally responsible for activation of at least one of the normal effector functions of the immune cell in which the Smart CAR, DE-CAR, Smart-DE-CAR, and/or Side CAR has been introduced. The term "effector function" refers to a specialized function of a cell. Effector function of a T cell, for example, may be cytolytic activity or helper activity including the secretion of cytokines. Thus the term "intracellular signaling element" refers to the portion of a protein which transduces the effector function signal and directs the cell to perform a specialized function. While the entire intracellular signaling domain can be employed, in many cases the intracellular element or intracellular signaling element need not consist of the entire domain. To the extent that a truncated portion of the intracellular signaling domain is used, such truncated portion may be used as long as it transduces the effector function signal. The term intracellular signaling element is thus also meant to include any truncated portion of the intracellular signaling domain sufficient to transduce the effector function signal. Examples of intracellular signaling elements for use in the Smart CAR, DE-CAR, Smart-DE-CAR, and/or Side CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

In some embodiments, the intracellular signaling element of the Smart CAR, DE-CAR, Smart-DE-CAR, and/or Side CAR can comprise the CD3-zeta signaling domain by itself or it can be combined with any other desired intracellular signaling element(s) useful in the context of a Smart CAR, DE-CAR, Smart-DE-CAR, and/or Side CAR of the invention. For example, the intracellular signaling element of the Smart CAR, DE-CAR, Smart-DE-CAR, and/or Side CAR can comprise a CD3 zeta chain portion and a costimulatory signaling element. The costimulatory signaling element refers to a portion of the Smart CAR, DE-CAR, Smart-DE-CAR, and/or Side CAR comprising the intracellular element of a costimulatory molecule. In some embodiments, a costimulatory molecule is a cell surface molecule other than an antigen receptor or its ligands that enhances response of lymphocytes to an antigen. Examples of such molecules include CD27, CD28, 4-1BB (CD137), OX40, CD30, CD40, PD1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CAR T-cells in vitro and augments human T-cell persistence and antitumor activity in vivo (Song et al. Blood. 2012; 119(3):696-706, which is incorporated by reference in its entirety for all purposes). In some embodiments, the Smart CAR, DE-CAR, Smart-DE-CAR, and/or Side CAR of the present invention comprises the primary cytoplasmic signaling sequence and/or the secondary cytoplasmic signaling sequence as the intracellular element.

In some embodiments, the Smart CAR, DE-CAR, Smart-DE-CAR, and/or Side CAR of the present invention comprises an intracellular element of a GITR as the intracellular element. The intracellular element of a GITR includes variants having the same function. The term "variant" means any variant comprising substitution, deletion or addition of one or a few to plural amino acids, provided that the variant substantially retains the same function as the original sequence possesses. An example of the intracellular element of a GITR used in the present invention includes an intracellular domain comprising amino acid numbers 193 to 241 of a GITR (NCBI RefSeq: NP_004186.1, SEQ ID NO: 43).

For the Smart CAR, DE-CAR, Smart-DE-CAR, and/or Side CAR of the present invention, in addition to the intracellular element of a GITR, an intracellular element derived from other polypeptides can be used. Examples of other intracellular elements include cytoplasmic sequences derived from a TCR complex and a costimulatory molecule, and any variant having the same function as those sequences.

The primary cytoplasmic signaling sequence regulates primary activation of a TCR complex. The primary cytoplasmic signaling sequence that stimulates the activation may comprise a signal transduction motif known as an immunoreceptor tyrosine-based activation motif (ITAM) [Nature, vol. 338, pp. 383-384 (1989)]. On the other hand, the primary cytoplasmic signaling sequence that acts in an inhibitory way comprises a signal transduction motif known as an immunoreceptor tyrosine-based inhibition motif (ITIM) [J Immunol., vol. 162, No. 2, pp. 897-902 (1999)]. In the present invention, an intracellular element having an ITAM or an ITIM can be used.

In some embodiments, the intracellular element having an ITAM includes intracellular elements having ITAM derived from CD3ζ, FcRγ, FcRβ, CD3γ, CD3δ, CD3ε, CD5, CD22, CD79a, CD79b, and CD66d. Examples of the ITAM include peptides having sequences of amino acid numbers 51 to 164 of CD3ζ (NCBI RefSeq: NP_932170.1, SEQ ID NO: 17), amino acid numbers 45 to 86 of FcεRIγ (NCBI RefSeq: NP_004097.1, SEQ ID NO: 18), amino acid numbers 201 to 244 of FcεRIβ (NCBI RefSeq: NP_000130.1, SEQ ID NO: 19), amino acid numbers 139 to 182 of CD3γ (NCBI RefSeq: NP_000064.1, SEQ ID NO: 20), amino acid numbers 128 to 171 of CD3 δ (NCBI RefSeq: NP_000723.1, SEQ ID NO: 21), amino acid numbers 153 to 207 of CD3ε (NCBI RefSeq: NP_000724.1, SEQ ID NO: 22), amino acid numbers 402 to 495 of CD5 (NCBI RefSeq: NP_055022.2, SEQ ID NO:23), amino acid numbers 707 to 847 of CD22 (NCBI RefSeq: NP_001762.2, SEQ ID NO: 24), amino acid numbers 166 to 226 of CD79a (NCBI RefSeq: NP_001774.1, SEQ ID NO: 25, amino acid numbers 182 to 229 of CD79b (NCBI RefSeq: NP_000617.1, SEQ ID NO: 26), and amino acid numbers 177 to 252 of CD66d (NCBI RefSeq: NP_001806.2, SEQ ID NO: 27), and their variants having the same function as these peptides have. The amino acid number based on amino acid sequence information of NCBI RefSeq ID or GenBank described herein is numbered based on the full length of the precursor (comprising a signal peptide sequence etc.) of each protein.

Examples of the intracellular element comprising a secondary cytoplasmic signaling sequence that can be used in the present invention include sequences derived from CD2, CD4, CD5, CD8α, CD8β, CD28, CD134, CD137, ICOS, and CD154.

Specific examples thereof include peptides having sequences of amino acid numbers 236 to 351 of CD2 (NCBI RefSeq: NP_001758.2, SEQ ID NO: 28), amino acid numbers 421 to 458 of CD4 (NCBI RefSeq: NP_000607.1, SEQ ID NO: 29), amino acid numbers 402 to 495 of CD5 (NCBI RefSeq: NP_055022.2, SEQ ID NO: 30), amino acid numbers 207 to 235 of CD8α (NCBI RefSeq: NP_001759.3, SEQ ID NO: 31), amino acid numbers 196 to 210 of CD8β (GenBank: AAA35664.1, SEQ ID NO: 32), amino acid numbers 181 to 220 of CD28 (NCBI RefSeq: NP_006130.1, SEQ ID NO: 33), amino acid numbers 214 to 255 of CD137 (4-1BB, NCBI RefSeq: NP_001552.2, SEQ ID NO: 34), amino acid numbers 241 to 277 of CD134 (OX40, NCBI RefSeq: NP_003318.1, SEQ ID NO: 35), and amino acid numbers 166 to 199 of ICOS (NCBI RefSeq: NP_036224.1, SEQ ID NO: 36), and their variants having the same function as these peptides have.

The present invention includes a Smart CAR, DE-CAR, Smart-DE-CAR, and/or Side CAR comprising only an intracellular element of a GITR as the intracellular element, and a Smart CAR, DE-CAR, Smart-DE-CAR, and/or Side CAR comprising one or more, for example, 2 or more intracellular elements in addition to the intracellular element of a GITR. Examples include a Smart CAR, DE-CAR, Smart-DE-CAR, and/or Side CAR comprising an intracellular element of a GITR and an intracellular element of CD3ζ as the intracellular elements, and a Smart CAR, DE-CAR, Smart-DE-CAR, and/or Side CAR comprising an intracellular element of a GITR, an intracellular element of CD3ζ and an intracellular element of CD28 as the intracellular elements. In some embodiments, the Smart CAR, DE-CAR, Smart-DE-CAR, and/or Side CAR comprises two or more copies of the same intracellular element which are linked in tandem. In some embodiments, the present invention provides a Smart CAR, DE-CAR, Smart-DE-CAR, and/or Side CAR in which an intracellular element of a GITR is arranged on a C-terminal side relative to an intracellular element of CD3ζ, that is, a Smart CAR, DE-CAR, Smart-DE-CAR, and/or Side CAR comprising an intracellular element of CD3ζ and an intracellular element of a GITR which are linked in this order from the N-terminal side. In some embodiments, the Smart CAR(s), DE-CAR(s), Smart-DE-CAR(s), and/or Side-CARs are obtained by further adding an intracellular element of CD28 to the aforementioned Smart CAR, DE-CAR, Smart-DE-CAR, and/or Side CAR, that is, a Smart CAR, DE-CAR, Smart-DE-CAR, and/or Side CAR comprising an intracellular element of CD28, an intracellular element of CD3ζ, and an intracellular element of a GITR which are linked in this order from the N-terminal side, and a Smart CAR, DE-CAR, Smart-DE-CAR, and/or Side CAR comprising an intracellular element of CD3ζ, an intracellular element of a GITR, and an intracellular element of CD28 which are linked in this order from the N-terminal side. In some embodiments, the Smart CAR, DE-CAR, Smart-DE-CAR, and/or Side CAR has an intracellular element of a GITR arranged on a C-terminal side.

In some embodiments, a Smart CAR, DE-CAR, Smart-DE-CAR, and/or Side CAR comprising a plurality of intracellular elements has an oligopeptide linker or a polypeptide linker inserted between the intracellular elements to link the elements. In some embodiments, the linker has a length of 2 to 10 amino acids. In some embodiments, the linker has a glycine-serine continuous sequence.

In some embodiments, depending on the intracellular domain, the CAR, Smart CAR, DE-CAR, Smart-DE-CAR, and/or Side-CAR are capable of eliciting polyfunctional responses in a T-cell, natural killer cell, and/or B-cell. For example, in some embodiments, Smart CAR, DE-CAR, Smart-DE-CAR, and/or Side CAR expressing cell described herein can further express another agent, e.g., an agent which enhances the activity of a Smart CAR, DE-CAR, Smart-DE-CAR, and/or Side CAR expressing cell. For example, an agent which increases the activity of the cell. Molecules that increase the activity of the cells include cytokine, interleukins, chemokines, immunomodulatory proteins, including, for example, IL1, IL2, IL6, IL12, TNFα, IFNγ.

In some embodiments, the intracellular domain comprises polypeptides which activate alternative signaling pathways, including other T cell signaling pathways, NOTCH, TGFa, GPCR mediated pathways, survival factors, death factors, WNT or Hedgehog, etc.

In some embodiments, Smart CAR, DE-CAR, Smart-DE-CAR, and/or Side CAR expressing cells described herein can further express another agent, e.g., an agent which enhances the activity of a Smart CAR, DE-CAR, Smart-DE-CAR, and/or Side CAR expressing cell. For example, an agent which inhibits an inhibitory molecule. Inhibitory molecules, e.g., PD1, can, in some embodiments, decrease the ability of a Smart CAR, DE-CAR, Smart-DE-CAR, and/or Side CAR expressing cell to mount an immune effector response. Examples of inhibitory molecules include PD1, PD-L1, CTLA4, TIM3, LAG3, VISTA, BTLA, TIGIT, LAIR1, CD160, 2B4, DO, NDO, and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling element described herein. In one embodiment, the agent comprises a first polypeptide, e.g., of an inhibitory molecule such as PD1, LAG3, CTLA4, CD160, BTLA, LAIR1, TIM3, 2B4 and TIGIT, or a fragment of any of these (e.g., at least a portion of an extracellular domain of any of these), and a second polypeptide which is an intracellular signaling element described herein (e.g., comprising a costimulatory element (e.g., 41BB, CD27 or CD28, e.g., as described herein) and/or a primary signaling element (e.g., a CD3 zeta signaling element described herein). In some embodiments, the agent comprises a first polypeptide of PD1 or a fragment thereof (e.g., at least a portion of an extracellular element of PD1), and a second polypeptide of an intracellular signaling element described herein (e.g., a CD28 signaling element described herein and/or a CD3 zeta signaling element described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75, which is incorporated by reference in its entirety for all purposes). Two ligands for PD1, PD-L1 and PD-L2 have been shown to downregulate T cell activation upon binding to PD1 (Freeman et al. 2000 J Exp Med 192:1027-34; Latchman et al. 2001 Nat Immunol 2:261-8; Carter et al. 2002 Eur J Immunol 32:634-43, which are incorporated by reference in their entirety for all purposes). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094, which are incorporated by reference in their entirety for all purposes). Immune suppression can be reversed by inhibiting the local interaction of PD1 with PD-L1.

Transmembrane Element and Spacer Element

The Smart CAR, DE-CAR, Smart-DE-CAR, and/or Side CAR of the present invention comprises a transmembrane element. The transmembrane element is attached to the extracellular element of the Smart CAR, DE-CAR, Smart-DE-CAR, and/or Side CAR. In some embodiments, a transmembrane element includes one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In some embodiments, the transmembrane element is associated with one of the other elements used in the Smart CAR, DE-CAR, Smart-DE-CAR, and/or Side CAR. In some embodiments, the transmembrane element is selected or modified by amino acid substitution to avoid binding of such elements to the transmembrane elements of the same or different surface membrane proteins, e.g., to minimize interactions with other members of the receptor complex. In some embodiments, the transmembrane element is capable of homodimerization with another Smart CAR, DE-CAR, Smart-DE-CAR, and/or Side CAR on the cell surface. In some embodiments, the amino acid sequence of the transmembrane element may be modified or substituted so as to minimize interactions with the binding elements of the native binding partner present in the same cell.

The transmembrane element may be contributed by the protein contributing the multispecific extracellular inducer clustering element, the protein contributing the effector function signaling element, the protein contributing the proliferation signaling portion, or by a totally different protein. For the most part it will be convenient to have the transmembrane element naturally associated with one of the elements. In some cases it will be desirable to employ the transmembrane element of the ζ, η or FcεR1γ chains which contain a cysteine residue capable of disulfide bonding, so that the resulting chimeric protein will be able to form disulfide linked dimers with itself, or with unmodified versions of the ζ, η or FcεR1γ chains or related proteins. In some embodiments, the transmembrane element will be selected or modified by amino acid substitution to avoid binding of such elements to the transmembrane elements of the same or different surface membrane proteins to minimize interactions with other members of the receptor complex. In some embodiments it will be desirable to employ the transmembrane element of ζ, η, FcεR1-γ and -β, MB1 (Igα), B29 or CD3-γ, ζ, or ε, in order to retain physical association with other members of the receptor complex.

In some embodiments, the transmembrane element is derived from a natural polypeptide, or may be artificially designed. Transmembrane elements derived from a natural polypeptide can be obtained from any membrane-binding or transmembrane protein. For example, a transmembrane element of a T cell receptor a or β chain, a CD3ζ chain, CD28, CD3ε, CD45, CD4, CD5, CD8, CD9, CD16, CD22, CD33, CD37, CD64, CD8β, CD86, CD134, CD137, ICOS, CD154, or a GITR can be used. An artificially designed transmembrane element n is a polypeptide mainly comprising hydrophobic residues such as leucine and valine. In some embodiments, a triplet of phenylalanine, tryptophan and valine is found at each end of the synthetic transmembrane element. In some embodiments, a short oligopeptide linker or a polypeptide linker, for example, a linker having a length of 2 to 10 amino acids can be arranged between the transmembrane element and the intracellular element. In some embodiments, a linker sequence having a glycine-serine continuous sequence can be used.

In some embodiments, a transmembrane element having a sequence of amino acid numbers 153 to 180 of CD28 (NCBI RefSeq: NP_006130.1, SEQ ID NO: 37) can be used as the transmembrane element. In some embodiments, a transmembrane element having a sequence of amino acid numbers 162 to 183 of a GITR (NCBI RefSeq: NP_004186.1, SEQ ID NO: 38) can be used.

In some embodiments, a spacer element can be arranged between the extracellular element and the transmembrane element, or between the intracellular element and the transmembrane element. In some embodiments, a spacer element is an oligopeptide or polypeptide that serves to link the transmembrane element with the extracellular element and/or the transmembrane element with the intracellular element. In some embodiments, the spacer element comprises up to 300 amino acids, or 10 to 100 amino acids, or 25 to 50 amino acids.

In some embodiments, the spacer element has a sequence that promotes binding of a Smart CAR, DE-CAR, Smart-DE-CAR, and/or Side CAR with an antigen and/or enhances signaling into a cell. Examples of such amino acids include cysteine, a charged amino acid, and serine and threonine in a potential glycosylation site, and these amino acids can be used as an amino acid constituting the spacer element.

In some embodiments, the spacer element comprises amino acid numbers 118 to 178 which is a hinge region of CD8α (NCBI RefSeq: NP_001759.3, SEQ ID NO: 39), amino acid numbers 135 to 195 of CD8β (GenBank: AAA35664.1, SEQ ID NO: 40), amino acid numbers 315 to 396 of CD4 (NCBI RefSeq: NP_000607.1, SEQ ID NO: 41), or amino acid numbers 137 to 152 of CD28 (NCBI RefSeq: NP_006130.1, SEQ ID NO: 42). In some embodiments, the spacer element is a part of a constant region of an antibody H chain or L chain (CH1 region or CL region). In some embodiments, the spacer element may be an artificially synthesized sequence.

In some embodiments, the Smart CAR, DE-CAR, Smart-DE-CAR, and/or Side CAR of the present invention forms a polymer, particularly, a dimer. For example, cysteine is inserted into the spacer element and/or the transmembrane element to polymerize (dimerize) the Smart CAR, DE-CAR, Smart-DE-CAR, and/or Side CAR.

In some embodiments, a signal peptide sequence can be linked to the N-terminus of a Smart CAR, DE-CAR, Smart-DE-CAR, and/or Side CAR nucleic acid or polypeptide. The signal peptide sequence exists at the N-terminus of many secretory proteins and membrane proteins, and has a length of 15 to 30 amino acids. Since many of the protein molecules mentioned above as the intracellular element have signal peptide sequences, the signal peptides can be used as a signal peptide for the Smart CAR, DE-CAR, Smart-DE-CAR, and/or Side CAR of the present invention.

Chimeric Antigen Receptors Coupled with Destabilizing Elements (DE-CAR)

In some embodiments of the present invention, destabilizing elements, as described above, are combined in cis with a CAR, as described above, so that the amount of the CAR polypeptide in the eukaryotic cell is under the control of the DE. This is one embodiment of the DE-CAR of the invention.

In some embodiments, destabilizing elements are selected for use with a CAR depending upon the eukaryotic cell that will host the DE-CAR, or the target of the DE-CAR, or the subject to be administered the eukaryotic cell with a DE-CAR, or a combination of the foregoing.

In some embodiments, the DE-CAR will have DE(s) that can be induced to increase polypeptide stability in the eukaryotic cell and/or the DE-CAR will have DE(s) that can be induced to increase the degradation rate of the DE-CAR polypeptide in the eukaryotic cell. In some embodiments, the DE(s) of the DE-CAR can be induced to decrease the degradation rate of DE-CAR polypeptide in the eukaryotic cell.

In some embodiments, the amount of DE-CAR in the host cell is modulated by the presence, absence and/or amount of ligand for the DE. The presence, absence and/or amount of ligand alters the degradation rare of the DE-CAR in the host cell and results in a gain, loss or maintenance of the amount of DE-CAR in the host cell. In this manner, the presence, absence and/or amount of is used to change (or maintain) the amount of DE-CAR in the cell and thus change (or maintain) the reactivity of the host cell towards the target of the DE-CAR.

Chimeric Antigen Receptors: Side-CARs

In some embodiments, the CARs, Smart CARs, DE-CAR, and/or Smart-DE-CARs of the invention are comprised of at least two parts which associate to form a functional CAR or DE-CAR. In some embodiments, the extracellular antigen binding element is expressed as a separate part from the transmembrane element, optional spacer, and the intracellular element of a CAR. In some embodiments, the separate extracellular binding element is associated with the host cell membrane (through a means other than a transmembrane polypeptide). In some embodiments, the intracellular element is expressed as a separate part from the extracellular element, transmembrane element, and optionally the spacer. In some embodiments the extracellular element and intracellular element are expressed separately and each has a transmembrane element, and optionally a spacer. In some embodiments, each part of the CAR or DE-CAR has an association element ("Side-CAR") for bringing the two parts together to form a functional CAR or DE-CAR.

In some embodiments, host cells make both parts of the CAR or DE-CAR. In some embodiments, different host cells make one part of the CAR or DE-CAR. In some embodiments, one part is made ex vivo, and a host cell makes the other part of the CAR or DE-CAR. In this embodiment, and the host cell expressing one part and the ex vivo part may be administered together or separately to the subject. In some embodiments, the nucleic acids encoding one or both parts of the CAR or DE-CAR are under the control of an inducible control region, an RNA control device, and/or a degron, providing control at transcription, mRNA stability, translation, and polypeptide stability stages.

In some embodiments, the Side-CAR acts in response to a small molecule, polypeptide, or other stimulus (e.g., light, heat, etc.) Upon binding with the small molecule, polypeptide, or interacting with the other stimulus, the Side-CAR is able to associate with the other Side-CAR element bringing together the two parts of the CAR or DE-CAR. In some embodiments, one part of the CAR or DE-CAR is membrane bound through a transmembrane polypeptide segment and the other part is not. In this embodiment, a Side-CAR is attached to transmembrane portion of membrane bound part on the opposite site of the membrane from the CAR part attached to the transmembrane element. In some embodiments, the Side-CAR is attached to the transmembrane element through a spacer polypeptide.

In some embodiments, the Side-CAR is, for example, FK506 binding protein (FKBP), calcineurin subunit A, cyclophilin, FKBP-rapamycin associated protein, Gyrase B (gyrB), DHFR, DmrB, PYL, ABI, Cry2, CIB1, GAI and/or GID1. In some embodiments, the small molecule that interacts with the Side-CAR is, for example, rapamycin, rapamycin analog, courmermycin, methotrexate, AP20187, abscisic acid, and/or gibberellin. In some embodiments, the stimulus is binding to the small molecule, or adsorption of light, for example, blue light. In some embodiments, the Side-CAR is activated to react chemically with the other Side-CAR.

In some embodiments, an antibody is used to associate the two Side-CARs and form an active CAR and/or DE-CAR. In some embodiments, the two Side-CARs shares epitopes that are bound by the antibody so that the antibody can crosslink the side-CARs together. In some embodiments, the Side-CARs have different epitopes and the antibody is a bispecific antibody with one arm of the antibody binding to one of the epitopes on one of the Side-CARs and the other arm of the antibody binding to a different epitope on the other Side-CAR. In some embodiments, the extracellular element does not have a Side-CAR and the bispecific antibody recognizes an epitope on the extracellular element. In some embodiments, no Side-CAR is used and the bispecific antibody recognizes an epitope on the extracellular element and an epitope on the extracellular side of the transmembrane element. In some embodiments, the antibody for crosslinking the Side-CARs has the same specie origin as the patient. In some embodiments, the antibody is a chimeric antibody, humanized antibody, humaneered antibody, or other combination antibody formed from framework regions taken from an antibody of one specie combined with all or part of the CDRs of another antibody from a different species. In some embodiments, the antibody is a human, mouse, rat, or other mammalian antibody. In some embodiments, the Side-CAR and its epitope are recognized as self. In some embodiments, the bispecific antibody is made of framework regions from one species. In some embodiments, the framework regions of the bispecific antibody are human. In some embodiments, the bispecific antibody is made from two fully human antibodies. In some embodiments, the bispecific antibody is made from two antibodies from the same species.

In some embodiments, the extracellular element is not membrane associated and is free in solution. In this embodiment, the extracellular element and the host cell with the transmembrane element-intracellular element must find each other before they associate through the Side-CARs and/or via an antibody. This search phase adds another level of post-translational control over CAR and/or DE-CAR polypeptide activity. In some embodiments, the extracellular element is made ex vivo and the amount of extracellular element administered to the patient is used to control the activity of the CAR and/or DE-CAR polypeptide. The half-life of the extracellular element can also be controlled by selecting a full length, or fragment of the extracellular element with the desired half-life. The extracellular element can also be modified to raise or lower its half-life. For example, the extracellular element could be glycosylated or PEGylated to increase its half-life. Controlling the half-life of the extracellular element will impact the level of control achieved by administering different doses of extracellular element during treatment. In some embodiments, the extracellular element has an Fc portion that is bound by the host-cell Side-CAR when the extracellular element is bound to its epitope. In some embodiments, the host cell Side-CAR is CD16, which binds to Fc regions of the extracellular element when the extracellular element is bound to epitope.

In some embodiments, the extracellular element is associated with the host cell membrane through a tether. In some embodiments, the tether is through a glycophosphatidylinositol (GPI) which binds to the phosphate groups of the membrane bilayer. In this embodiment, the extracellular element includes a GPI signal sequence on its C-terminal end. In some embodiments, the human GPI signal sequence is, for example:

```
(CD24)
                                        SEQ ID NO: 44
TNATTKAAGGALQSTASLFVVSLSLLHLYS (CNTN1)
                                        SEQ ID NO: 45
VSQVKISGAPTLSPSLLGLLLPAFGILVYLEF (EFNA1)
                                        SEQ ID NO: 46
PEVRVLHSIGHSAAPRLFPLAWTVLLLPLLLLQTP (EFNA2)
                                        SEQ ID NO: 47
EAPEPIFTSNNSCSSPGGCRLFLSTIPVLWRLLGS (EFNA3)
                                        SEQ ID NO: 48
QVPKLEKSISGTSPKREHLPLAVGIAFFLMTFLAS (EFNA5)
                                        SEQ ID NO: 49
ESAEPSRGENAAQTPRIPSRLLAILLFLLAMLLTL (FOLI)
                                        SEQ ID NO: 50
YAAAMSGAGPWAAWPFLLSLALMLLWLLS (LSAMP)
                                        SEQ ID NO: 51
SVRGINGSISLAVPLWLLAASLLCLLSKC (PPB1)
                                        SEQ ID NO: 52
TTDAAHPGRSVVPALLPLLAGTLLLLETATAP (RTN4R)
                                        SEQ ID NO: 53
DSEGSGALPSLTCSLTPLGLALVLWTVLGPC
```

In this embodiment, the extracellular element also has an N-terminal signal sequence that directs the extracellular element into the endoplasmic reticulum during translation. In this embodiment, the extracellular element is tethered to the cell membrane through GPI and so the Side-CAR of the extracellular element and the Side-CAR of the transmembrane element—intracellular element can associate upon interaction with the appropriate small molecule, polypeptide (e.g., antibody), or physical stimuli. In addition, in this embodiment, activity of the CAR or DE-CAR polypeptide can be controlled by reducing the amount of membrane tethered extracellular element using an enzyme, for example, phospholipase C which can cleave the GPI link liberating the extracellular element from the host cell. This cleavage of the GPI link reduces CAR or DE-CAR polypeptide activity because the interaction between the two parts of the CAR or DE-CAR polypeptide is reduced (the extracellular element is diluted by this cleavage). In some embodiments, the activity of the enzyme, e.g., phospholipase C, is regulated. In some embodiments, the enzyme activity is regulated by a competitive inhibitor, e.g., inhibitors of phospholipase c are commercially available from Sigma-Aldrich and Santa Cruz Biotechnology.

Lymphocyte Expansion Molecule and Other Regulatory Factors

In some embodiments, a lymphocyte expansion molecule ("LEM") is used in the invention. Examples of LEMs include, but are not limited to mouse LEM or the BC05111 gene as found at Uniprot or NCBI, human LEM or the C1ORF177 gene as found at Uniprot or NCBI, and other polypeptides having homology to human or mouse LEM and the activity of LEM. Nucleic acids encoding these LEMs are also part of this aspect of the invention. In some embodiments, ILL IL2, IL4, IL5, IL6, IL7, IL10, IL12, IL15, GM-CSF, G-CSF, TNFα, and/or IFNγ are used in the invention.

In some embodiments, the LEM, ILL IL2, IL4, IL5, IL6, IL7, IL10, IL12, IL15, GM-CSF, G-CSF, TNFα, and/or IFNγ are combined with a DE to regulate the expression of the LEM. When a DE is used, it is operably placed in cis to the LEM, ILL IL2, IL4, IL5, IL6, IL7, IL10, IL12, IL15, GM-CSF, G-CSF, TNFα, and/or IFNγ, so the amount of LEM, ILL IL2, IL4, IL5, IL6, IL7, IL10, IL12, IL15, GM-CSF, G-CSF, TNFα, and/or IFNγ polypeptide in the eukaryotic cell is under the control of the DE.

In some embodiments, destabilizing elements are selected for use with a LEM, ILL IL2, IL4, IL5, IL6, IL7, IL10, IL12, IL15, GM-CSF, G-CSF, TNFα, and/or IFNγ depending upon the eukaryotic cell that will host the DE-LEM, DE-IL1, DE-IL2, DE-IL4, DE-IL5, DE-IL6, DE-IL7, DE-IL10, DE-IL12, DE-IL15, DE-GM-CSF, DE-G-CSF, DE-TNFα, and/or DE-IFNγ, or the target cell of the DE-LEM, DE-IL1, DE-IL2, DE-IL4, DE-IL5, DE-IL6, DE-IL7, DE-IL10, DE-IL12, DE-IL15, DE-GM-CSF, DE-G-CSF, DE-TNFα, and/or DE-IFNγ, or the subject to be administered the eukaryotic cell with a DE-LEM, DE-IL1, DE-IL2, DE-IL4, DE-IL5, DE-IL6, DE-IL7, DE-IL10, DE-IL12, DE-IL15, DE-GM-CSF, DE-G-CSF, DE-TNFα, and/or DE-IFNγ, or a combination of the foregoing.

In some embodiments, one or more DEs with the same or different ligands are placed in cis with the LEM, ILL IL2, IL4, IL5, IL6, IL7, IL10, IL12, IL15, GM-CSF, G-CSF, TNFα, and/or IFNγ. In some embodiments, some or all of the DEs can be induced to increase the amount of DE-LEM, DE-IL1, DE-IL2, DE-IL4, DE-IL5, DE-IL6, DE-IL7, DE-IL10, DE-IL12, DE-IL15, DE-GM-CSF, DE-G-CSF, DE-TNFα, and/or DE-IFNγ polypeptide in the eukaryotic cell and/or some or all of the DE(s) can be induced to decrease the amount of DE-LEM, DE-IL1, DE-IL2, DE-IL4, DE-IL5, DE-IL6, DE-IL7, DE-IL10, DE-IL12, DE-IL15, DE-GM-CSF, DE-G-CSF, DE-TNFα, and/or DE-IFNγ polypeptide in the eukaryotic cell. In some embodiments, the ligands for the different DEs can be added in a coordinated fashion to produce different amounts of DE-LEM, DE-IL1, DE-IL2, DE-IL4, DE-IL5, DE-IL6, DE-IL7, DE-IL10, DE-IL12, DE-IL15, DE-GM-CSF, DE-G-CSF, DE-TNFα, and/or DE-IFNγ polypeptide in the eukaryotic cell over time. In some embodiments, the ligands for the different DEs can be added in a coordinated fashion to produce a constant or stable amount of DE-LEM, DE-IL1, DE-IL2, DE-IL4, DE-IL5, DE-IL6, DE-IL7, DE-IL10, DE-IL12, DE-IL15, DE-GM-CSF, DE-G-CSF, DE-TNFα, and/or DE-IFNγ polypeptide in the eukaryotic cell over a period of time.

In some embodiments, binding of ligand to the DE of the DE-LEM, DE-IL1, DE-IL2, DE-IL4, DE-IL5, DE-IL6, DE-IL7, DE-IL10, DE-IL12, DE-IL15, DE-GM-CSF, DE-G-CSF, DE-TNFα, and/or DE-IFNγ induces a change in the conformation of the DE-LEM, DE-IL1, DE-IL2, DE-IL4, DE-IL5, DE-IL6, DE-IL7, DE-IL10, DE-IL12, DE-IL15, DE-GM-CSF, DE-G-CSF, DE-TNFα, and/or DE-IFNγ that increases or decreases the degradation rate of the DE-LEM, DE-IL1, DE-IL2, DE-IL4, DE-IL5, DE-IL6, DE-IL7, DE-IL10, DE-IL12, DE-IL15, DE-GM-CSF, DE-G-CSF, DE-TNFα, and/or DE-IFNγ polypeptide in the eukaryotic cell.

In some embodiments of the present invention, RNA control devices, as described above, are combined in cis with a LEM, ILL IL2, IL4, IL5, IL6, IL7, IL10, IL12, IL15, GM-CSF, G-CSF, TNFα, and/or IFNγ as described above, so that the expression level of the LEM, ILL IL2, IL4, IL5, IL6, IL7, IL10, IL12, IL15, GM-CSF, G-CSF, TNFα, and/or IFNγ is under the control of the RNA control device. In some embodiments of the present invention, the RNA control device operates in trans to the LEM, IL1, IL2, IL4, IL5, IL6, IL7, IL10, IL12, IL15, GM-CSF, G-CSF, TNFα, and/or IFNγ so that the expression level of the LEM, IL1, IL2, IL4, IL5, IL6, IL7, IL10, IL12, IL15, GM-CSF, G-CSF, TNFα, and/or IFNγ is under the control of the RNA control device.

In some embodiments, RNA control devices are selected for use with a LEM, IL1, IL2, IL4, IL5, IL6, IL7, IL10, IL12, IL15, GM-CSF, G-CSF, TNFα, and/or IFNγ depending upon the eukaryotic cell that will host the Smart LEM, Smart ILL Smart IL2, Smart IL4, Smart IL5, Smart IL6, Smart IL7, Smart IL10, Smart IL12, Smart IL15, Smart GM-CSF, Smart G-CSF, Smart TNFα, and/or Smart IFNγ or the target cell of the Smart LEM, or the subject to be administered the eukaryotic cell with a Smart LEM, Smart IL1, Smart IL2, Smart IL4, Smart IL5, Smart IL6, Smart IL7, Smart IL10, Smart IL12, Smart IL15, Smart GM-CSF, Smart G-CSF, Smart TNFα, and/or Smart IFNγ, or a combination of the foregoing.

In some embodiments, the Smart LEM, Smart IL1, Smart IL2, Smart IL4, Smart IL5, Smart IL6, Smart IL7, Smart IL10, Smart IL12, Smart IL15, Smart GM-CSF, Smart G-CSF, Smart TNFα, and/or Smart IFNγ will have regulatory element(s) that can be induced to increase polypeptide expression in the eukaryotic cell and/or the Smart LEM, Smart ILL Smart IL2, Smart IL4, Smart IL5, Smart IL6, Smart IL7, Smart IL10, Smart IL12, Smart IL15, Smart GM-CSF, Smart G-CSF, Smart TNFα, and/or Smart IFNγ will have regulatory element(s) that can be induced to decrease polypeptide expression in the eukaryotic cell. In some embodiments, the ligands for the different RNA control devices can be added in a coordinated fashion to produce different amounts of LEM, IL1, IL2, IL4, IL5, IL6, IL7, IL10, IL12, IL15, GM-CSF, G-CSF, TNFα, and/or IFNγ polypeptide in the eukaryotic cell over time. In some embodiments, the ligands for the different RNA control devices can be added in a coordinated fashion to maintain a constant or stable amount of LEM, IL1, IL2, IL4, IL5, IL6, IL7, IL10, IL12, IL15, GM-CSF, G-CSF, TNFα, and/or IFNγ polypeptide in the eukaryotic cell over a period of time.

The regulatory element of the Smart LEM, Smart ILL Smart IL2, Smart IL4, Smart IL5, Smart IL6, Smart IL7, Smart IL10, Smart IL12, Smart IL15, Smart GM-CSF, Smart G-CSF, Smart TNFα, and/or Smart IFNγ may operate through any of the means described above (e.g., ribozyme activity, antisense, RNAi, secondary structure sequestration of mRNA structures, etc.). Binding of ligand to the sensor element of the Smart LEM, Smart ILL Smart IL2, Smart IL4, Smart IL5, Smart IL6, Smart IL7, Smart IL10, Smart IL12, Smart IL15, Smart GM-CSF, Smart G-CSF, Smart TNFα, and/or Smart IFNγ RNA induces a change in the conformational equilibria of the Smart LEM which increase or decreases translation of the LEM, ILL IL2, IL4, IL5, IL6, IL7, IL10, IL12, IL15, GM-CSF, G-CSF, TNFα, and/or IFNγ RNA into LEM, IL1, IL2, IL4, IL5, IL6, IL7, IL10, IL12, IL15, GM-CSF, G-CSF, TNFα, and/or IFNγ polypeptide.

In some embodiments, the LEM, ILL IL2, IL4, IL5, IL6, IL7, IL10, IL12, IL15, GM-CSF, G-CSF, TNFα, and/or IFNγ is under the control of both DE(s) and RNA control device(s). In some embodiments, some or all of the DEs and some or all of the RNA control devices will have regulatory element(s) that can be induced to increase the amount of LEM, ILL IL2, IL4, IL5, IL6, IL7, IL10, IL12, IL15, GM-CSF, G-CSF, TNFα, and/or IFNγ polypeptide in the eukaryotic cell and/or some or all of the DEs and some or all of the RNA control devices will have regulatory element(s) that can be induced to decrease the amount of LEM, ILL IL2, IL4, IL5, IL6, IL7, IL10, IL12, IL15, GM-CSF, G-CSF, TNFα, and/or IFNγ polypeptide in the eukaryotic cell. In some embodiments, the ligands for the different DEs and RNA control devices can be added in a coordinated fashion to produce different amounts of DE-LEM, DE-IL1, DE-IL2, DE-IL4, DE-IL5, DE-IL6, DE-IL7, DE-IL10, DE-IL12, DE-IL15, DE-GM-CSF, DE-G-CSF, DE-TNFα, and/or DE-IFNγ polypeptide in the eukaryotic cell over time. In some embodiments, the ligands for the different DEs and RNA control devices can be added in a coordinated fashion to maintain a constant or stable amount of DE-LEM, DE-IL1, DE-IL2, DE-IL4, DE-IL5, DE-IL6, DE-IL7, DE-IL10, DE-IL12, DE-IL15, DE-GM-CSF, DE-G-CSF, DE-TNFα, and/or DE-IFNγ polypeptide in the eukaryotic cell over a period of time.

Eukaryotic Cells

In the present invention, various eukaryotic cells can be used as the eukaryotic cell of the invention. In some embodiments, the eukaryotic cells of the invention are animal cells. In some embodiments, the eukaryotic cells are mammalian cells, such as mouse, rat, rabbit, hamster, porcine, bovine, feline, or canine. In some embodiments, the mammalian cells are cells of primates, including but not limited to, monkeys, chimpanzees, gorillas, and humans. In some embodiments, the mammalians cells are mouse cells, as mice routinely function as a model for other mammals, most particularly for humans (see, e.g., Hanna, J. et al., *Science* 318:1920-23, 2007; Holtzman, D. M. et al., *J Clin Invest.* 103(6):R15-R21, 1999; Warren, R. S. et al., *J Clin Invest.* 95: 1789-1797, 1995; each publication is incorporated by reference in its entirety for all purposes). Animal cells include, for example, fibroblasts, epithelial cells (e.g., renal, mammary, prostate, lung), keratinocytes, hepatocytes, adipocytes, endothelial cells, and hematopoietic cells. In some embodiments, the animal cells are adult cells (e.g., terminally differentiated, dividing or non-dividing) or embryonic cells (e.g., blastocyst cells, etc.) or stem cells. In some embodiments, the eukaryotic cell is a cell line derived from an animal or other source.

In some embodiments, the eukaryotic cells are stem cells. A variety of stem cells types are known in the art and can be used as eukaryotic cells of the invention, including for example, embryonic stem cells, inducible pluripotent stem cells, hematopoietic stem cells, neural stem cells, epidermal neural crest stem cells, mammary stem cells, intestinal stem cells, mesenchymal stem cells, olfactory adult stem cells, testicular cells, and progenitor cells (e.g., neural, angioblast, osteoblast, chondroblast, pancreatic, epidermal, etc.). In some embodiments, the stem cells are stem cell lines derived from cells taken from a subject.

In some embodiments, the eukaryotic cell is a cell found in the circulatory system of a mammal, including humans.

Exemplary circulatory system cells include, among others, red blood cells, platelets, plasma cells, T-cells, natural killer cells, B-cells, macrophages, neutrophils, or the like, and precursor cells of the same. As a group, these cells are defined to be circulating eukaryotic cells of the invention. In some embodiments, the eukaryotic cells are derived from any of these circulating eukaryotic cells. The present invention may be used with any of these circulating cells or eukaryotic cells derived from the circulating cells. In some embodiments, the eukaryotic cell is a T-cell or T-cell precursor or progenitor cell. In some embodiments, the eukaryotic cell is a helper T-cell, a cytotoxic T-cell, a memory T-cell, a regulatory T-cell, a natural killer T-cell, a mucosal associated invariant T-cell, a gamma delta T cell, or a precursor or progenitor cell to the aforementioned. In some embodiments, the eukaryotic cell is a natural killer cell, or a precursor or progenitor cell to the natural killer cell. In some embodiments, the eukaryotic cell is a B-cell, or a B-cell precursor or progenitor cell. In some embodiments, the eukaryotic cell is a neutrophil or a neutrophil precursor or progenitor cell. In some embodiments, the eukaryotic cell is a megakaryocyte or a precursor or progenitor cell to the megakaryocyte. In some embodiments, the eukaryotic cell is a macrophage or a precursor or progenitor cell to a macrophage.

In some embodiments the eukaryotic cells are plant cells. In some embodiments the plant cells are cells of monocotyledonous or dicotyledonous plants, including, but not limited to, alfalfa, almonds, asparagus, avocado, banana, barley, bean, blackberry, brassicas, broccoli, cabbage, canola, carrot, cauliflower, celery, cherry, chicory, citrus, coffee, cotton, cucumber, eucalyptus, hemp, lettuce, lentil, maize, mango, melon, oat, papaya, pea, peanut, pineapple, plum, potato (including sweet potatoes), pumpkin, radish, rapeseed, raspberry, rice, rye, sorghum, soybean, spinach, strawberry, sugar beet, sugarcane, sunflower, tobacco, tomato, turnip, wheat, zucchini, and other fruiting vegetables (e.g. tomatoes, pepper, chili, eggplant, cucumber, squash etc.), other bulb vegetables (e.g., garlic, onion, leek etc.), other pome fruit (e.g. apples, pears etc.), other stone fruit (e.g., peach, nectarine, apricot, pears, plums etc.), Arabidopsis, woody plants such as coniferous and deciduous trees, an ornamental plant, a perennial grass, a forage crop, flowers, other vegetables, other fruits, other agricultural crops, herbs, grass, or perennial plant parts (e.g., bulbs; tubers; roots; crowns; stems; stolons; tillers; shoots; cuttings, including un-rooted cuttings, rooted cuttings, and callus cuttings or callus-generated plantlets; apical meristems etc.). The term "plants" refers to all physical parts of a plant, including seeds, seedlings, saplings, roots, tubers, stems, stalks, foliage and fruits.

In other embodiments, the eukaryotic cells are algal, including but not limited to algae of the genera *Chlorella, Chlamydomonas, Scenedesmus, Isochrysis, Dunaliella, Tetraselmis, Nannochloropsis,* or *Prototheca*. In some embodiments, the eukaryotic cells are fungi cells, including, but not limited to, fungi of the genera *Saccharomyces, Klyuveromyces, Candida, Pichia, Debaromyces, Hansenula, Yarrowia, Zygosaccharomyces,* or *Schizosaccharomyces*.

In some embodiments, a source of cells is obtained from a subject. The subject may be any living organisms. In some embodiments, the cells are derived from cells obtained from a subject. Examples of subjects include humans, dogs, cats, mice, rats, and transgenic species thereof. In some embodiments, T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available in the art, may be used. In some embodiments, T cells can be obtained from a unit of blood collected from a subject using any number of techniques known to the skilled artisan, such as Ficoll separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In an alternative aspect, the wash solution lacks calcium and may lack magnesium or may lack many if not all divalent cations. Initial activation steps in the absence of calcium can lead to magnified activation.

Enrichment of a T cell population by negative selection can be accomplished with a combination of antibodies directed to surface markers unique to the negatively selected cells. In some embodiments, cells are enriched by cell sorting and/or selection via negative magnetic immunoadherence or flow cytometry using a cocktail of monoclonal antibodies directed to cell surface markers present on the cells. For example, to enrich for CD4+ cells, a monoclonal antibody cocktail typically includes antibodies to CD14, CD20, CD11b, CD16, HLA-DR, and CD8. In some embodiments, it may be desirable to enrich for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005, each of which is incorporated by reference in its entirety for all purposes.

In some embodiments, NK cells may be expanded in the presence of a myeloid cell line that has been genetically modified to express membrane bound IL-15 and 4-1BB ligand (CD137L). A cell line modified in this way which does not have MEW class I and II molecules is highly susceptible to NK cell lysis and activates NK cells. For example, K562 myeloid cells can be transduced with a chimeric protein construct consisting of human IL-15 mature peptide fused to the signal peptide and transmembrane domain of human CD8α and GFP. Transduced cells can then be single-cell cloned by limiting dilution and a clone with the highest GFP expression and surface IL-15 selected. This clone can then be transduced with human CD137L, creating a K562-mb15-137L cell line. To preferentially expand NK cells, peripheral blood mononuclear cell cultures containing NK cells are cultured with a K562-mb15-137L cell line in the presence of 10 IU/mL of IL-2 for a period of time sufficient to activate and enrich for a population of NK cells. This period can range from 2 to 20 days, preferably about 5 days. Expanded NK cells may then be transduced with the anti-CD19-BB-ζ chimeric receptor.

Nucleic Acids

In some embodiments, the present invention relates to the nucleic acids that encode, at least in part, the individual peptides, polypeptides, proteins, and RNA control devices of the present invention. In some embodiments, the nucleic acids may be natural, synthetic or a combination thereof. The nucleic acids of the invention may be RNA, mRNA, DNA or cDNA.

In some embodiments, the nucleic acids of the invention also include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, e.g., mammalian cells, the expression vector can be integrated into the host cell chromosome and then replicate with the host chromosome. Similarly, vectors can be integrated into the chromosome of prokaryotic cells.

Expression vectors also generally contain a selection gene, also termed a selectable marker. Selectable markers are well-known in the art for prokaryotic and eukaryotic cells, including host cells of the invention. Generally, the selection gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. In some embodiments, an exemplary selection scheme utilizes a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art.

An example of a promoter that is capable of expressing a Smart CAR, DE-CAR, Smart-DE-CAR, and/or Side CAR transgene in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009), which is incorporated by reference in its entirety for all purposes. Another example of a promoter is the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to the simian virus 40 (SV40) early promoter, mouse mammary tumor virus promoter (MMTV), human immunodeficiency virus (HIV) long terminal repeat (LTR) promoter, MoMuLV promoter, phosphoglycerate kinase (PGK) promoter, MND promoter (a synthetic promoter that contains the U3 region of a modified MoMuLV LTR with myeloproliferative sarcoma virus enhancer, see, e.g., Li et al., J. Neurosci. Methods vol. 189, pp. 56-64 (2010) which is incorporated by reference in its entirety for all purposes), an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention is not limited to the use of constitutive promoters.

Inducible promoters are also contemplated as part of the invention. Examples of inducible promoters include, but are not limited to a metallothionine promoter, a glucocorticoid promoter, a progesterone promoter, a tetracycline promoter, a c-fos promoter, the T-REx system of ThermoFisher which places expression from the human cytomegalovirus immediate-early promoter under the control of tetracycline operator(s), and RheoSwitch promoters of Intrexon. Karzenowski, D. et al., BioTechiques 39:191-196 (2005); Dai, X. et al., Protein Expr. Purif 42:236-245 (2005); Palli, S. R. et al., Eur. J. Biochem. 270:1308-1515 (2003); Dhadialla, T. S. et al., Annual Rev. Entomol. 43:545-569 (1998); Kumar, M. B, et al., J. Biol. Chem. 279:27211-27218 (2004); Verhaegent, M. et al., Annal. Chem. 74:4378-4385 (2002); Katalam, A. K., et al., Molecular Therapy 13:S103 (2006); and Karzenowski, D. et al., Molecular Therapy 13:S194 (2006), U.S. Pat. Nos. 8,895,306, 8,822,754, 8,748,125, 8,536,354, all of which are incorporated by reference in their entirety for all purposes.

Expression vectors of the invention typically have promoter elements, e.g., enhancers, to regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

In some embodiments, it may be desirable to modify the polypeptides of the present invention. One of skill will recognize many ways of generating alterations in a given nucleic acid construct to generate variant polypeptides Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, e.g., Gillam and Smith, Gene 8:81-97, 1979; Roberts et al., Nature 328:731-734, 1987, which is incorporated by reference in its entirety for all purposes). In some embodiments, the recombinant nucleic acids encoding the polypeptides of the invention are modified to provide preferred codons which enhance translation of the nucleic acid in a selected organism.

The polynucleotides of the invention also include polynucleotides including nucleotide sequences that are substantially equivalent to the polynucleotides of the invention. Polynucleotides according to the invention can have at least about 80%, more typically at least about 90%, and even more typically at least about 95%, sequence identity to a polynucleotide of the invention. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

Nucleic acids which encode protein analogs or variants in accordance with this invention (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989) and/or Current Protocols in Molecular Biology, Ausubel et al., eds, Green Publishers Inc. and Wiley and Sons, N.Y (1994), each of which is incorporated by reference in its entirety for all purposes. Chemical synthesis using methods well known in the art, such as that described by Engels et al., *Angew Chem Intl Ed.* 28:716-34, 1989 (which is incorporated by reference in its entirety for all purposes), may also be used to prepare such nucleic acids.

In some embodiments, amino acid "substitutions" for creating variants are preferably the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

The present invention provides a nucleic acid encoding the Smart CAR, DE-CAR, Smart-DE-CAR, and/or Side CAR of the invention. The nucleic acid encoding the Smart CAR, DE-CAR, Smart-DE-CAR, and/or Side CAR can be easily prepared from an amino acid sequence of the specified CAR combined with the sequence of the RNA control device by a conventional method. A base sequence encoding an amino acid sequence can be obtained from the aforementioned NCBI RefSeq IDs or accession numbers of GenBenk for an amino acid sequence of each element, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acid of the present invention can be linked to another nucleic acid so as to be expressed under control of a suitable promoter. The nucleic acid of the present invention can be also linked to, in order to attain efficient transcription of the nucleic acid, other regulatory elements that cooperate with a promoter or a transcription initiation site, for example, a nucleic acid comprising an enhancer sequence, a polyA site, or a terminator sequence. In addition to the nucleic acid of the present invention, a gene that can be a marker for confirming expression of the nucleic acid (e.g. a drug resistance gene, a gene encoding a reporter enzyme, or a gene encoding a fluorescent protein) may be incorporated.

When the nucleic acid of the present invention is introduced into a cell ex vivo, the nucleic acid of the present invention may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid of the present invention is also useful. Particularly, a composition in a form suitable for administration to a living body which contains the nucleic acid of the present invention carried by a suitable vector is suitable for in vivo gene therapy.

Process for Producing Eukaryotic Cells Expressing Smart CAR, DE-CAR, Smart-DE-CAR, and/or Side CAR A process for producing a cell expressing the Smart CAR, DE-CAR, Smart-DE-CAR, and/or Side CAR of the present invention includes a step of introducing the nucleic acid encoding a Smart CAR, DE-CAR, Smart-DE-CAR, and/or Side CAR described above into a eukaryotic cell. In some embodiments, this step is carried out ex vivo. For example, a cell can be transformed ex vivo with a virus vector or a non-virus vector carrying the nucleic acid of the present invention to produce a cell expressing the Smart CAR, DE-CAR, Smart-DE-CAR, and/or Side CAR of the present invention.

In the process of the present invention, a eukaryotic cell as describe above is used. In some embodiments, a eukaryotic cell derived from a mammal, for example, a human cell, or a cell derived from a non-human mammal such as a monkey, a mouse, a rat, a pig, a horse, or a dog can be used. The cell used in the process of the present invention is not particularly limited, and any cell can be used. For example, a cell collected, isolated, purified or induced from a body fluid, a tissue or an organ such as blood (peripheral blood, umbilical cord blood etc.) or bone marrow can be used. A peripheral blood mononuclear cell (PBMC), an immune cell, a dendritic cell, a B cell, a hematopoietic stem cell, a macrophage, a monocyte, a NK cell or a hematopoietic cell, an umbilical cord blood mononuclear cell, a fibroblast, a precursor adipocyte, a hepatocyte, a skin keratinocyte, a mesenchymal stem cell, an adipose stem cell, various cancer cell strains, or a neural stem cell can be used. In the present invention, particularly, use of a T cell, a precursor cell of a T cell (a hematopoietic stem cell, a lymphocyte precursor cell etc.) or a cell population containing them is preferable. Examples of the T cell include a CD8-positive T cell, a CD4-positive T cell, a regulatory T cell, a cytotoxic T cell, and a tumor infiltrating lymphocyte. The cell population containing a T cell and a precursor cell of a T cell includes a PBMC. The aforementioned cells may be collected from a living body, obtained by expansion culture of a cell collected from a living body, or established as a cell strain. When transplantation of the produced Smart CAR, DE-CAR, Smart-DE-CAR, and/or Side CAR expressing cell or a cell differentiated from the produced Smart CAR, DE-CAR, Smart-DE-CAR, and/or Side CAR expressing cell into a living body is desired, it is preferable to introduce the nucleic acid into a cell collected from the living body itself.

In some embodiments, the nucleic acid encoding the Smart CAR, DE-CAR, Smart-DE-CAR, and/or Side CAR of the present invention is inserted into a vector, and the vector is introduced into a cell. In some embodiments, the nucleic acid encoding the Smart CAR, DE-CAR, Smart-DE-CAR, and/or Side CAR is introduced to the eukaryotic cell by transfection (e.g., Gorman, et al. Proc. Natl. Acad. Sci. 79.22 (1982): 6777-6781, which is incorporated by reference in its entirety for all purposes), transduction (e.g., Cepko and Pear (2001) Current Protocols in Molecular Biology unit 9.9; DOI: 10.1002/0471142727.mb0909s36, which is incorporated by reference in its entirety for all purposes), calcium phosphate transformation (e.g., Kingston, Chen and Okayama (2001) Current Protocols in Molecular Biology Appendix 1C; DOI: 10.1002/0471142301.nsa01cs01, which is incorporated by reference in its entirety for all purposes), cell-penetrating peptides (e.g., Copolovici, Langel, Eriste, and Langel (2014) ACS Nano 2014 8 (3), 1972-1994; DOI: 10.1021/nn4057269, which is incorporated by reference in its entirety for all purposes), electroporation (e.g Potter (2001) Current Protocols in Molecular Biology unit 10.15; DOI: 10.1002/0471142735.im1015s03 and Kim et al (2014) Genome 1012-19. doi:10.1101/gr.171322.113, Kim et al. 2014 describe the Amaza Nucleofector, an optimized electroporation system, both of these references are incorporated by reference in their entirety for all purposes), microinjection (e.g., McNeil (2001) Current Protocols in Cell Biology unit 20.1; DOI: 10.1002/0471143030.cb2001s18, which is incorporated by reference in its entirety for all purposes), liposome or cell fusion (e.g., Hawley-Nelson and Ciccarone (2001) Current Protocols in Neuroscience Appendix 1F; DOI: 10.1002/0471142301.nsa01fs10, which is incorporated by reference in its entirety for all purposes), mechanical manipulation (e.g. Sharon et al. (2013) PNAS 2013 110(6); DOI: 10.1073/pnas.1218705110, which is incorporated by reference in its entirety for all purposes) or other well-known technique for delivery of nucleic acids to eukaryotic cells. Once introduced, Smart CAR, DE-CAR, Smart-DE-CAR, and/or Side CAR nucleic acid can be transiently expressed episomally, or can be integrated into the genome of the eukaryotic cell using well known techniques such as recombination (e.g., Lisby and Rothstein (2015) Cold Spring Harb Perspect Biol. March 2; 7(3). pii: a016535. doi: 10.1101/cshperspect.a016535, which is incorporated by reference in its entirety for all purposes), or non-homologous integration (e.g., Deyle and Russell (2009) Curr Opin Mol Ther. 2009 August; 11(4):442-7, which is incorporated by reference in its entirety for all purposes). The efficiency of homologous and non-homologous recombination can be facilitated by genome editing technologies that introduce targeted double-stranded breaks (DSB). Examples of DSB-generating technologies are CRISPR/Cas9, TALEN, Zinc-Finger Nuclease, or equivalent systems (e.g., Cong et al. Science 339.6121 (2013): 819-823, Li et al. Nucl. Acids Res (2011): gkr188, Gajet al. Trends in Biotechnology 31.7 (2013): 397-405, all of which are incorporated by reference in their entirety for all purposes), transposons such as Sleeping Beauty (e.g., Singh et al (2014) Immunol Rev. 2014 January; 257(1):181-90. doi: 10.1111/imr.12137, which is incorporated by reference in its entirety for all purposes), targeted recombination using, for example, FLP recombinase (e.g., O'Gorman, Fox and Wahl Science (1991) 15:251(4999):1351-1355, which is incorporated by reference in its entirety for all purposes), CRE-LOX (e.g., Sauer and Henderson *PNAS* (1988): 85; 5166-5170), or equivalent systems, or other techniques known in the art for integrating the nucleic acid encoding the Smart CAR, DE-CAR, Smart-DE-CAR, and/or Side CAR into the eukaryotic cell genome.

In an embodiment, the nucleic acid encoding the Smart CAR, DE-CAR, Smart-DE-CAR, and/or Side CAR is integrated into the eukaryotic cell chromosome at a genomic safe harbor site, such as, for example, the CCR5, AAVS1, human ROSA26, or PSIP1 loci. (Sadelain et al., Nature Rev. 12:51-58 (2012); Fadel et al., J. Virol. 88(17):9704-9717 (2014); Ye et al., PNAS 111(26):9591-9596 (2014), all of which are incorporated by reference in their entirety for all purposes.) In an embodiment, the integration of the nucleic acid encoding the Smart CAR, DE-CAR, Smart-DE-CAR, and/or Side CAR at the CCR5 or PSIP1 locus is done using a gene editing system, such as, for example, CRISPR, TALEN, or Zinc-Finger nuclease systems. In an embodiment, the eukaryotic cell is a human, T-lymphocyte and a CRISPR system is used to integrate the Smart CAR, DE-CAR, Smart-DE-CAR, and/or Side CAR at the CCR5 or PSIP1 locus. In an embodiment, integration of the nucleic acid at CCR5 or PSIP1 using the CRISPR system also deletes a portion, or all, of the CCR5 gene or PSIP1 gene. In an embodiment, Cas9 in the eukaryotic cell may be derived from a plasmid encoding Cas9, an exogenous mRNA encoding Cas9, or recombinant Cas9 polypeptide alone or in a ribonucleoprotein complex. (Kim et al (2014) Genome 1012-19. doi:10.1101/gr.171322.113.; Wang et al (2013) Cell 153 (4). Elsevier Inc.: 910-18. doi:10.1016/j.cell.2013.04.025, both of which are incorporated by reference in their entirety for all purposes.)

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In some embodiments, transduction can be done with a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. As the virus vector, a virus vector lacking the replicating ability so as not to self-replicate in an infected cell is preferably used.

In some embodiments, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+envAm-12 (U.S. Pat. No. 5,278,056, which is incorporated by reference in its entirety for all purposes), and Psi-Crip (Proceedings of the National Academy of Sciences of the United States of America, vol. 85, pp. 6460-6464 (1988), which is incorporated by reference in its entirety for all purposes). A retrovirus particle can also be prepared using a 293 cell or a T cell having high transfection efficiency. Many kinds of retrovirus vectors produced based on retroviruses and packaging cells that can be used for packaging of the retrovirus vectors are widely commercially available from many companies.

A number of viral based systems have been developed for gene transfer into mammalian cells. A selected gene can be inserted into a vector and packaged in viral particles using techniques known in the art. The recombinant virus can then be isolated and delivered to cells of the subject either in vivo or ex vivo. A number of viral systems are known in the art. In some embodiments, adenovirus vectors are used. A number of adenovirus vectors are known in the art. In some embodiments, lentivirus vectors are used.

In some embodiments, a viral vector derived from a RNA virus is used to introduce the Smart CAR, Smart-DE-CAR, and/or Side-CAR encoding polynucleotides. In some embodiments, the RNA virus vector encodes the reverse complement or antisense strand of the polynucleotide encoding the RNA control device and CAR construct (the complementary strand encodes the sense strand for the RNA control device, DE, CAR and/or Side-CAR construct). In this embodiment, the RNA control device is not active in the single stranded, RNA virus vector. In some embodiments, the sense strand of the RNA control device, DE, CAR and/or Side-CAR construct is encoded in the RNA virus vector, and the viral vector with the RNA control device, DE, CAR and/or Side-CAR construct is maintained and replicated in the presence of ligand for the sensor element of the RNA control device. In some embodiments, the viral vector encoding the sense strand of the RNA control device, DE, CAR and/or Side-CAR construct in the viral vector is maintained and replicated without ligand for the sensor element.

In some embodiments, a non-virus vector is used in combination with a liposome and a condensing agent such as a cationic lipid as described in WO 96/10038, WO 97/18185, WO 97/25329, WO 97/30170 and WO 97/31934 (which are incorporated herein by reference in their entirety for all purposes). The nucleic acid of the present invention can be introduced into a cell by calcium phosphate transduction, DEAE-dextran, electroporation, or particle bombardment.

In some embodiments, chemical structures with the ability to promote stability and/or translation efficiency are used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA. The 5' and 3' UTRs can be the naturally occurring, endogenous 5' and 3' UTRs for the nucleic acid of interest. In some embodiments, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3'UTR sequences can decrease the stability of mRNA. Therefore, 3' UTRs can be selected or designed to increase the stability of the transcribed RNA based on properties of UTRs that are well known in the art.

In some embodiments, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

In the step of introducing a nucleic acid into a cell, a functional substance for improving the introduction efficiency can also be used (e.g. WO 95/26200 and WO 00/01836, which are incorporated herein by reference in their entirety for all purposes). Examples of the substance for improving the introduction efficiency include a substance having ability to bind to a virus vector, for example, fibronectin and a fibronectin fragment. In some embodiments, a fibronectin fragment having a heparin binding site, for example, a fragment commercially available as RetroNectin (registered trademark, CH-296, manufactured by TAKARA BIO INC.) can be used. Also, polybrene which is a synthetic polycation having an effect of improving the efficiency of infection of a retrovirus into a cell, a fibroblast growth factor, V type collagen, polylysine or DEAE-dextran can be used.

In a preferable aspect of the present invention, the functional substance can be used in a state of being immobilized on a suitable solid phase, for example, a container used for cell culture (plate, petri dish, flask or bag) or a carrier (microbeads etc.).

Eukaryotic Cells Expressing the Smart CAR, DE-CAR, Smart-DE-CAR, and/or Side CAR The cell expressing the Smart CAR, DE-CAR, Smart-DE-CAR, and/or Side CAR of the present invention is a cell in which a nucleic acid encoding a Smart CAR, DE-CAR, Smart-DE-CAR, and/or Side CAR is introduced and expressed.

In some embodiments, a eukaryotic cell of the present invention binds to a specific antigen via the CAR, DE-CAR, and/or Side-CAR polypeptide causing the CAR, DE-CAR, and/or Side-CAR polypeptide to transmit a signal into the eukaryotic cell, and as a result, the eukaryotic cell is activated. The activation of the eukaryotic cell expressing the Smart CAR, DE-CAR, Smart-DE-CAR, and/or Side CAR is varied depending on the kind of a eukaryotic cell and the intracellular element of the Smart CAR, DE-CAR, Smart-DE-CAR, and/or Side CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and/or a macrophage.

In some embodiments, eukaryotic cells expressing CAR, Smart CAR, DE-CAR, Smart-DE-CAR, and/or Side CAR constructs are detected using Protein L (a bacterial surface protein isolated from *Peptostreptoccocus magnus* that selectively binds to variable light chains (kappa chain) of immunoglobulins. In some embodiments, Protein L is directly labeled with a reporter (e.g., a light emitting or absorbing moiety) or is labeled with an agent such as biotin. When biotin or related molecule is used to label the Protein L, binding of Protein L to eukaryotic cells displaying CAR, DE-CAR, and/or Side-CAR polypeptide is detected by adding a streptavidin (or similar paired molecule) labeled with reporter (e.g., phycoerythrin). Zheng et al., J. Translational Med., 10:29 (2012), which is incorporated by reference in its entirety for all purposes. Protein L binding to eukaryotic cells containing CAR, Smart CAR, DE-CAR, Smart-DE-CAR, and/or Side CAR constructs demonstrates the presence of antibody light chain, the extracellular domain of a CAR, on the eukaryotic cell. This method of detecting CAR expression on the eukaryotic cell can also be used to quantitate the amount of CAR, DE-CAR, and/or Side-CAR polypeptide on the surface of the eukaryotic cell. In some embodiments, Protein L is used in QC and QA methodologies for making eukaryotic cells with the CAR, Smart CAR, DE-CAR, Smart-DE-CAR, and/or Side CAR constructs of the invention.

In some embodiments, a eukaryotic cell expressing the Smart CAR, DE-CAR, Smart-DE-CAR, and/or Side CAR is used as a therapeutic agent to treat a disease. The therapeutic agent comprises the eukaryotic cell expressing the Smart CAR, DE-CAR, Smart-DE-CAR, and/or Side CAR as an active ingredient, and may further comprise a suitable excipient. Examples of the excipient include pharmaceutically acceptable excipients for the composition. The disease against which the eukaryotic cell expressing the Smart CAR, DE-CAR, Smart-DE-CAR, and/or Side CAR is administered is not particularly limited as long as the disease shows sensitivity to the eukaryotic cell. Examples of diseases of the invention include a cancer (blood cancer (leukemia), solid tumor etc.), an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis. The eukaryotic cell expressing the Smart CAR, DE-CAR, Smart-DE-CAR, and/or Side CAR of the present invention is administered for treatment of these diseases. The eukaryotic cell of the present invention can also be utilized for prevention of an infectious disease after bone marrow transplantation or exposure to radiation, donor lymphocyte transfusion for the purpose of remission of recurrent leukemia, and the like. The therapeutic agent comprising the eukaryotic cell expressing the Smart CAR, DE-CAR, Smart-DE-CAR, and/or Side CAR as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

In some embodiments, the eukaryotic cells with Smart CAR, DE-CAR, Smart-DE-CAR, and/or Side CAR are characterized prior to administration to the subject. In some embodiments, the eukaryotic cells with Smart CAR, DE-CAR, Smart-DE-CAR, and/or Side CAR are tested to confirm Smart CAR, DE-CAR, Smart-DE-CAR, and/or Side CAR expression. In some embodiments, the eukaryotic cells with Smart CAR, DE-CAR, Smart-DE-CAR, and/or Side CAR are exposed to a level of ligand(s) that results in a desired level of CAR, DE-CAR, and/or Side-CAR polypeptide expression in the eukaryotic cell. In some embodiments, this desired level of CAR, DE-CAR, and/or Side-CAR polypeptide produces eukaryotic cells with a desired level of anti-target cell activity, and/or a desired level of proliferative activity when placed in a subject.

In some embodiments, the Smart CAR, DE-CAR, Smart-DE-CAR, and/or Side CAR is used with a T-lymphocyte that has aggressive anti-tumor properties, such as those described in Pegram et al, CD28z CARs and armored CARs, 2014, Cancer J. 20(2):127-133, which is incorporated by reference in its entirety for all purposes. In some embodiments, the RNA control device of the invention is used with an armored CAR, DE-CAR, and/or Side-CAR polypeptide in a T-lymphocyte.

In some embodiments, any of the above Smart CAR, DE-CAR, Smart-DE-CAR, and/or Side CAR embodiments can also include a DE-LEM, Smart LEM or Smart-DE-LEM to provide controlled expression of LEM or DE-LEM. In these embodiments, the amount of LEM or DE-LEM is controlled so that its expansion signal is provided at a desired time. This control of the expansion signal is achieved by altering the amount of ligand (s) for the DE(s) and/or RNA control devices associated with the LEM or DE-LEM whereby the amount of LEM or DE-LEM is altered. In some embodiments, control of the LEM expansion signal is achieved by adding exogenous LEM to the eukaryotic cells at a desired time.

Pharmaceutical Compositions

Pharmaceutical compositions of the present invention may comprise a Smart CAR, DE-CAR, Smart-DE-CAR, and/or Side CAR expressing cell, e.g., a plurality of Smart CAR, DE-CAR, Smart-DE-CAR, and/or Side CAR expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

Suitable pharmaceutically acceptable excipients are well known to a person skilled in the art. Examples of the pharmaceutically acceptable excipients include phosphate buffered saline (e.g. 0.01 M phosphate, 0.138 M NaCl, 0.0027 M KCl, pH 7.4), an aqueous solution containing a mineral acid salt such as a hydrochloride, a hydrobromide, a phosphate, or a sulfate, saline, a solution of glycol or ethanol, and a salt of an organic acid such as an acetate, a propionate, a malonate or a benzoate. In some embodiments, an adjuvant such as a wetting agent or an emulsifier, and a pH buffering agent can also be used. In some embodiments, the pharmaceutically acceptable excipients described in Remington's Pharmaceutical Sciences (Mack Pub. Co., N.J. 1991) (which is incorporated herein by reference in its entirety for all purposes) can be appropriately used. The composition of the present invention can be formulated into a known form suitable for parenteral administration, for example, injection or infusion. In some embodiments, the composition of the present invention may comprise formulation additives such as a suspending agent, a preservative, a stabilizer and/or a dispersant, and a preservation agent for extending a validity term during storage.

A composition comprising the eukaryotic cells of the present invention as an active ingredient can be administered for treatment of, for example, a cancer (blood cancer (leukemia), solid tumor etc.), an inflammatory disease/autoimmune disease (asthma, eczema), hepatitis, and an infectious disease the cause of which is a virus such as influenza and HIV, a bacterium, or a fungus, for example, a disease such as tuberculosis, MRSA, VRE, or deep mycosis, depending on an antigen to which a CAR, DE-CAR, and/or Side-CAR polypeptide binds.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, intranasally, intraarterially, intratumorally, into an afferent lymph vessel, by intravenous (i.v.) injection, or intraperitoneally. In one aspect, the T cell compositions of the present invention are administered to a patient by intradermal or subcutaneous injection. In one aspect, the T-cell compositions of the present invention are administered by i.v. injection. The compositions of T-cells may be injected directly into a tumor, lymph node, or site of infection. In some embodiments, the administration is adoptive transfer.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). In some embodiments, a pharmaceutical composition comprising the eukaryotic cells described herein may be administered at a dosage of $10^4$ to $10^9$ cells/kg body weight, in some instances $10^5$ to $10^6$ cells/kg body weight, including all integer values within those ranges. In some embodiments, a eukaryotic cell composition may also be administered multiple times at these dosages. In some embodiments, eukaryotic cells can be administered by using infusion techniques that are commonly known in immunotherapy (see, e.g., Rosenberg et al., New Eng. J. of Med. 319:1676, 1988, which is incorporated by reference in its entirety for all purposes).

Uses of Eukaryotic Cells with Smart CAR, DE-CAR, Smart-DE-CAR, and/or Side CAR

In some embodiments, nucleic acids encoding Smart CAR(s), DE-CAR(s), Smart-DE-CAR(s), and/or Side CAR(s) of the invention are used to express CAR, DE-CAR, and/or Side-CAR polypeptides in eukaryotic cells. In some embodiments, nucleic acids encoding Smart CAR(s), DE-CAR(s), Smart-DE-CAR(s), and/or Side CAR(s) of the invention are used to express CAR, DE-CAR, and/or Side-CAR polypeptides in mammalian cells. In some embodiments, nucleic acids encoding Smart CAR(s), DE-CAR(s), Smart-DE-CAR(s), and/or Side CAR(s) of the invention are used to express CAR, DE-CAR, and/or Side-CAR polypeptides in human cells or murine cells. In some embodiments, nucleic acids encoding Smart CAR(s), DE-CAR(s), Smart-DE-CAR(s), and/or Side CAR(s) of the invention are used to express CAR, DE-CAR, and/or Side-CAR polypeptide in hematopoietic cells. In some embodiments, nucleic acids encoding Smart CAR(s), DE-CAR(s), Smart-DE-CAR(s), and/or Side CAR(s) of the invention are used to express CAR, DE-CAR, and/or Side-CAR polypeptides in T-cells, natural killer cells, B-cells, or macrophages. In some embodiments, nucleic acids encoding Smart CAR(s), DE-CAR(s), Smart-DE-CAR(s), and/or Side CAR(s) of the invention are used to express CAR, DE-CAR, and/or Side-CAR polypeptides in T-cells or natural killer cells.

In some embodiments, the nucleic acids encoding the Smart CAR(s), DE-CAR(s), Smart-DE-CAR(s), and/or Side CAR(s) of the invention are used to express a desired level of CAR, DE-CAR, and/or Side-CAR polypeptide on the surface of the eukaryotic cell. In this embodiment, the DE, RNA control device, and/or Side-CAR controls the level of CAR, DE-CAR, and/or Side-CAR polypeptide expression, at least in part, and by modulating the level of activity of the DE, RNA control device, and/or Side-CAR, a desired amount of CAR, DE-CAR, and/or Side-CAR polypeptide is expressed and displayed on the surface of the eukaryotic cell. In some embodiments, the DE increases the degradation rate of DE-CAR polypeptide in the eukaryotic cell and when ligand is bound by the DE, the rate of degradation decreases. In some embodiments, the DE increases degradation of the DE-CAR polypeptide when ligand is bound by the DE. In some embodiments, the RNA control device inhibits translation of the DE-CAR mRNA and when ligand binds to the sensor element of the RNA control device this inhibition of translation is reduced so that DE-CAR polypeptide expression is increased. In some embodiments, ligand for the Side-CAR causes the two Side-CAR polypeptides to form an active CAR. In some embodiments, ligand for the DE, the ligand for the RNA control device sensor, and/or the ligand for the Side-CAR is added in increasing amounts to the eukaryotic cells with the Smart CAR(s), DE-CAR(s), Smart-DE-CAR(s), and/or Side CAR(s) until a desired level of CAR, DE-CAR, and/or Side-CAR polypeptide is made in the eukaryotic cell. In some embodiments, the amount of CAR, DE-CAR, and/or Side-CAR polypeptide is measured using antibodies specific for the CAR, DE-CAR, and/or Side-CAR polypeptide. In some embodiments, the amount of CAR, DE-CAR, and/or Side-CAR polypeptide is measured using the antigen recognized by the extracellular element. In some embodiments, the amount of CAR, DE-CAR, and/or Side-CAR polypeptide is measured in a functional assay of target cell killing. In some embodiments, the amount of CAR, DE-CAR, and/or Side-CAR polypeptide is measured in a functional assay for eukaryotic cell proliferation (induced by the CAR, DE-CAR, and/or Side-CAR polypeptide). In some embodiments, the above eukaryotic cell is a T-lymphocyte or a natural killer cell or a macrophage or other phagocytic cell type.

In some embodiments, the ligand for the DE, the ligand for the RNA control device sensor, and/or the ligand for the Side-CAR is added in increasing amounts until a desired level of eukaryotic cell activity is obtained. In some embodiments, the desired eukaryotic cell activity is killing of a target cell. In some embodiments, target cell killing occurs over a desired time period, e.g., the killing of a certain number of target cells in 12 hours, or 24 hours, or 36 hours, or two days, or 3, 4, 5, 6, 7, 8, 9, 10, 11, 12, 13, 14, 15, 16, 17, 18, 19, 20, 21, 22, 23, 24, 25, 26, 27, or 28 days, or two months, or 3, 4, 5, or 6 months. In some embodiments, target cell killing is expressed as a half-life for a standardized number of target cells. In this embodiment, the half-life of target cell killing can be 12 hours, 24 hours, 36 hours, or 2, 3, 4, 5, 6, 7, 8, 9, 10, 11, 12, 13, 14, 15, 16, 17, 18, 19, 20, 21, 22, 23, 24, 25, 26, 27, or 28 days, or two months, or 3, 4, 5, or 6 months. In some embodiments, the desired eukaryotic cell activity is proliferation. In some embodiments, the cell proliferation occurs with a doubling time of 12 hours, 24 hours, 36 hours, two days, or 3, 4, 5, 6, or 7 days. In some embodiments, the above eukaryotic cell is a T-lymphocyte or a natural killer cell or a macrophage or other phagocytic cell type.

In some embodiments, a regime of different amounts of ligand (for the sensor, DE, and/or Side-CAR) is added over time so that different desired levels of CAR, DE-CAR, and/or Side-CAR polypeptide are present on the eukaryotic cell at different times. For example, in the treatment of cancer in patients with Smart CAR, DE-CAR, Smart-DE-CAR, and/or Side CAR T-cells or Smart CAR, DE-CAR, Smart-DE-CAR, and/or Side CAR natural killer cells, the amount of CAR, DE-CAR, and/or Side-CAR polypeptide expression may be reduced initially to reduce toxicity from tumor lysis, and as tumor mass is cleared, the amount of CAR, DE-CAR, and/or Side-CAR polypeptide expression can be increased to kill the remaining tumor cells as these become more rare within the body. In some embodiments, the CAR, DE-CAR, and/or Side-CAR polypeptide expression may be increased initially, and as tumor mass is reduced the CAR, DE-CAR, and/or Side-CAR polypeptide expression level is reduced to reduce killing of healthy tissue that also may express target antigen. In some embodiments, the reactivity towards tumor cells can be modulated so that the ratio of tumor cell killing to killing of normal tissue is maintained within a desired range. In some embodiments, the amount of CAR, DE-CAR, and/or Side-CAR polypeptide expressed on the surface of the eukaryotic cell is reduced by eukaryotic cell proliferation. As the eukaryotic cells proliferate, CAR, DE-CAR, and/or Side-CAR polypeptide will be diluted if the expression level from the Smart CAR, DE-CAR, Smart-DE-CAR, and/or Side CAR nucleic acid is insufficient to keep the CAR, DE-CAR, and/or Side-CAR polypeptide copy number at the level found in the parent eukaryotic cell (i.e., if the parent cell does not double its amount of CAR, DE-CAR, and/or Side-CAR polypeptide then each daughter cell will have a decreased amount CAR, DE-CAR, and/or Side-CAR polypeptide compared to the parent cell). In some embodiments, the CAR, DE-CAR, and/or Side-CAR polypeptide is designed to have a short half-life, in comparison to the doubling time for the eukaryotic cell in the subject. In some embodiments, the ligand(s) has a short half-life in the subject when compared to the doubling time of the eukaryotic cell in the subject. In some embodiments, an anti-ligand antibody or a different ligand binding molecule is administered to the subject or given to the eukaryotic cells (in vitro) so that the ligand binds to the antibody or ligand binding molecule and cannot react with the DE, RNA control device sensor, and/or Side-CAR. In some embodiments, the above eukaryotic cell is a T-lymphocyte or a natural killer cell or a macrophage or other phagocytic cell type.

In some embodiments, eukaryotic cells with Smart CAR(s), DE-CAR(s), Smart-DE-CAR(s), and/or Side CAR(s) of the invention expressed a desired amount of CAR, DE-CAR, and/or Side-CAR polypeptide so that a subject containing the eukaryotic cells with the CAR, DE-CAR, and/or Side-CAR polypeptide produce a therapeutic level of target cell killing while keeping toxicity and adverse events at acceptable levels. In some embodiments, the above eukaryotic cell is a T-lymphocyte or a natural killer cell or a macrophage or other phagocytic cell type. For example, Smart CAR(s), DE-CAR(s), Smart-DE-CAR(s), and/or Side CAR(s) of the invention can be used to reduce tumor lysis syndrome, cytokine storms, or healthy tissue killing by T-lymphocytes with Smart CAR, DE-CAR, Smart-DE-CAR, and/or Side CAR. In some embodiments, the amount of CAR, DE-CAR, and/or Side-CAR polypeptide expressed on the T-lymphocyte or other eukaryotic cell is individualized such that severe adverse events are prevented.

In some embodiments, the amount of CAR, DE-CAR, and/or Side-CAR polypeptide expressed by the eukaryotic cell is individualized for the subject by measuring the amount of target antigen on the subjects diseased tissue (or cells) and/or the amount of target antigen expressed on the subjects healthy tissue (or cells). In some embodiments, a biopsy of diseased and healthy tissue (or cells) is taken from the subject, and the amount of target antigen is measured using routine methods, e.g., antibodies to the target can be used to quantify target antigen expression. Based on the relative amount of target antigen expressed on diseased and healthy tissues (or cells) of the subject a desired level of Smart CAR, DE-CAR, Smart-DE-CAR, and/or Side CAR for the eukaryotic cell can be determined. Eukaryotic cells with the Smart CAR(s), DE-CAR(s), Smart-DE-CAR(s), and/or Side CAR(s) of the invention can then be programmed to express the desired amount of CAR, DE-CAR, and/or Side-CAR to give the desired level of CAR, DE-CAR, and/or Side-CAR activity. In some embodiments, the above eukaryotic cell is a T-lymphocyte or a natural killer cell or a macrophage or other phagocytic cell type.

In some embodiments, the Smart CAR, Smart-DE-CAR, and/or Side CAR of the invention is associated with two or more RNA control devices. In some embodiments, different amounts of the two or more ligands for the DE, Side-CAR, and/or two or more RNA control devices are added to the eukaryotic cells to produce a desired amount of CAR, DE-CAR, and/or Side-CAR polypeptide in the eukaryotic cell. In some embodiments, different regimes of combinations of the ligands are applied to the eukaryotic cells to produce a desired profile over time of the amount of CAR, DE-CAR, and/or Side-CAR polypeptide on the surface of the eukaryotic cell. In some embodiments, some of the RNA control devices increase expression of CAR, DE-CAR, and/or Side-CAR polypeptide when ligand for the sensor element is bound, and some of the RNA control devices decrease CAR, DE-CAR, and/or Side-CAR polypeptide expression when ligand for the sensor element is bound. In some embodiments, the above eukaryotic cell is a T-lymphocyte or a natural killer cell or a macrophage or other phagocytic cell type.

In some embodiments, Smart CAR(s), DE-CAR(s), Smart-DE-CAR(s), and/or Side CAR(s) are used for genetically engineering T-cells for cancer immunotherapy. When used for immunotherapy applications, T-cells are removed from a patient through leukopheresis and T-cells are preferentially sorted and saved. T cells are subjected to lentiviral or retroviral introduction (or other means of nucleic acid introduction) of the transgene that encodes the Smart CAR, DE-CAR, Smart-DE-CAR, and/or Side CAR, expanded to target therapeutic cell concentrations and infused into the patient, resulting in an autologous treatment with little graft vs host complications. Although CARs have been shown to be very effective at achieving and sustaining remissions for refractory/relapsed acute lymphoblastic leukemia (Maude et al., NEJM, 371:1507, 2014, which is incorporated by reference in its entirety for all purposes), dangerous side effects related to cytokine release syndrome (CRS), tumor lysis syndrome (TLS), B cell aplasia or "on-tumor, off-target" toxicities occur. Modulating CAR expression via the incorporation of DEs, RNA control devices, and/or Side-CARs in the Smart CAR(s), DE-CAR(s), Smart-DE-CAR(s), and/or Side CAR(s) of the invention can control these toxicities.

In some embodiments the nucleic acid sequences encoding a cognate RNA control device or devices are present in a nucleic acid locus encoding a chimeric antigen receptor transgene. In some embodiments, RNA control devices are encoded for as nucleic acid sequence in the vector proximal, distal, or within the ORF encoding a CAR, DE-CAR, and/or Side-CAR polypeptide. An example of a schematic of a vector is included in FIG. 1, adapted from (Budde et al., PLoS1, 2013, doi:10.1371/journal.pone.0082742, which is incorporated by reference in its entirety for all purposes). In some embodiments nucleic acid sequences encoding an RNA control device or devices are located within the 3' UTR region of the transgene. In some embodiments nucleic acid sequences encoding an RNA control device or devices are located in the 5' UTR region of the DE-CAR transgene. In some embodiments nucleic acid sequences encoding an RNA control device or devices are located within synthetic or natural introns flanked by coding or noncoding exons within the CAR transgene, or at intron/exon boundaries.

In some embodiments RNA control devices are present in cis within a mRNA encoding a CAR, DE-CAR, and/or Side-CAR polypeptide. In some embodiments, the CAR, DE-CAR, and/or Side-CAR polypeptide is encoded by an mRNA. The Smart CAR, DE-CAR, Smart-DE-CAR, and/or Side CAR mRNA may be delivered to T-cells via electroporation, transfection, or other methods known to those skilled in the art to create a transiently translated Smart CAR, DE-CAR, Smart-DE-CAR, and/or Side CAR T-cell. The RNA control device may act to modulate cognate mRNA stability or translation. The DE with its ligand may modulate the amount of DE-CAR and/or Side-CAR polypeptide in the eukaryotic cell. In some embodiments, these Smart CAR, DE-CAR, Smart-DE-CAR, and/or Side CAR mRNAs may be derived from in vitro transcription with a prokaryotic or bacteriophage RNA polymerase. In some embodiments, these Smart CAR, DE-CAR, Smart-DE-CAR, and/or Side CAR mRNAs may be derived from chemical synthesis of RNAs, enzymatic manipulation of chemically synthesized RNAs, or a combination of chemical synthesis and in vitro transcription of mRNAs. In some embodiments, Smart CAR, DE-CAR, Smart-DE-CAR, and/or Side CAR mRNAs may contain chemical modifications to base, sugar or backbone moieties, which may increase or decrease mRNA stability, alter the base-pairing characteristics of canonical RNA bases, or alter the translated polypeptide sequence by facilitating interactions between modified mRNA codons and charged non-cognate tRNAs.

In some embodiments, T-cells comprise DE-CARs and/or Side-CARs with integrated RNA control devices. In some embodiments, combinational Smart DE-CAR and/or Side-CAR T-cells are used, wherein independent T-cells express orthogonal Smart CAR(s), DE-CAR(s), Smart-DE-CAR(s), and/or Side CAR(s), that target distinct tumor-associated antigens (TAAs). Targeting multiple TAAs simultaneously can direct a greater CTL response against the primary tumor or metastases and prevent relapse. A potential disadvantage of using CAR, DE-CAR and/or Side-CAR polypeptide T-cells is that there may be a higher probability of eliciting on-target, off-tumor effects, leading to toxicity. The coupling of DEs, RNA control devices, and/or Side-CARs to CARs in Smart CAR(s), DE-CAR(s), Smart-DE-CAR(s), and/or Side CAR(s) T-cells mitigates the toxicity concern while enabling the stronger response and relapse prevention of Smart CAR, DE-CAR, Smart-DE-CAR, and/or Side CAR T-cells. In some embodiments, Smart-DE-CAR and/or Side-CAR T-cells are controlled by multiple ligands. In some embodiments, the DE, RNA control devices, and Side-CARs used in combinational Smart CAR, DE-CAR, Smart-DE-CAR, and/or Side CAR T-cells are specific for different ligands, or combinations of ligands, such that expression cross-talk is minimized or eliminated. In some embodiments, the Smart CAR, DE-CAR, Smart-DE-CAR, and/or Side CAR T-cells are used against a single tumor by targeting different tumor-associated surface antigens. In some embodiments, these Smart CAR, DE-CAR, Smart-DE-CAR, and/or Side CAR T-cells are used against a single tumor by targeting the same tumor-associated surface antigen, with different transmembrane, hinge, receptor, costimulatory elements, other aspects of the Smart CAR, DE-CAR, Smart-DE-CAR, and/or Side CAR or combinations thereof. In some embodiments the Smart CAR, DE-CAR, Smart-DE-CAR, and/or Side CAR T-cells are used against clonally heterogeneous tumor types, wherein each population of Smart CAR, DE-CAR, Smart-DE-CAR, and/or Side CAR T-cell is specific for a particular TAA. In some embodiments, the relative populations of Smart CAR, DE-CAR, Smart-DE-CAR, and/or Side CAR T-cells is controlled. In some embodiments, combinations of ligands are dosed to induce expression of a specific population of Smart CAR, DE-CAR, Smart-DE-CAR, and/or Side CAR T-cells. In some embodiments, universal Smart CAR, DE-CAR, Smart-DE-CAR, and/or Side CAR T-cells are used. Such CAR T-cells are single T-cells that comprise more than one Smart CAR, DE-CAR, Smart-DE-CAR, and/or Side CAR or more than one means for Smart CAR, DE-CAR, Smart-DE-CAR, and/or Side CAR expression. In some embodiments universal CAR T-cells contain more than one, two, three or more Smart CAR(s), DE-CAR(s), Smart-DE-CAR(s), and/or Side CAR(s). In some embodiments, each Smart CAR, DE-CAR, Smart-DE-CAR, and/or Side CAR in the universal-CAR T-cell are controlled by RNA control devices, DEs, and/or Side-CARs. In some embodiments, only a subset of CARs are controlled by RNA control devices, DEs, and/or Side-CARs. In some embodiments, the RNA control devices in an universal-CAR T cell are specific for different ligands, or combinations of ligands, such that expression cross-talk is minimized or eliminated. In some embodiments, the Side-CARs are specific for different ligands, or combinations of ligands, such that expression cross-talk is minimized or eliminated.

In some embodiments, Smart CAR, DE-CAR, Smart-DE-CAR, Side CAR and/or universal-CARs are designed to include receptors against antigens that are of bacterial, fungal or viral origin. Because Smart CAR(s), DE-CAR(s), Smart-DE-CAR(s), and/or Side CAR(s) can be utilized to fight infections, which are a source of toxicity in immunocompromised patients, such anti-pathogen Smart CAR(s), DE-CAR(s), Smart-DE-CAR(s), and/or Side CAR(s) can be used in conjunction with Smart CAR, DE-CAR, Smart-DE-CAR, and/or Side CAR T-cell therapy specific for a TAA.

In some embodiments, multiple orthogonally targeted Smart CAR, DE-CAR, Smart-DE-CAR, and/or Side CAR T-cells are used, where different Smart CAR(s), DE-CAR(s), Smart-DE-CAR(s), and/or Side CAR(s) target separate antigens, or combinational Smart CAR, DE-CAR, Smart-DE-CAR, and/or Side CAR T-cells where a single Smart CAR, DE-CAR, Smart-DE-CAR, or Side CAR T cell targets multiple antigens, whereby tumor cell killing is increased, complete responses and sustained remissions are more likely. This combination CAR, DE-CAR, and/or Side-CAR polypeptide approach will be enhanced by RNA control devices which respond to bio-orthogonal ligands to control individual CAR, DE-CAR, and/or Side-CAR polypeptide expression within a single or population of modified T-cells.

In some embodiments, any of the above DE-CAR or Smart-DE-CAR embodiments can also include a DE-LEM, Smart LEM or Smart-DE-LEM to provide controlled expression of LEM or DE-LEM. In these embodiments, the amount of LEM or DE-LEM is controlled so that its expansion signal is provided at a desired time. This control of the expansion signal is achieved by altering the amount of ligand (s) for the DE(s) and/or RNA control devices associated with the LEM or DE-LEM whereby the amount of LEM or DE-LEM is altered. In some embodiments, control of the LEM expansion signal is achieved by adding exogenous LEM to the eukaryotic cells at a desired time.

The inventions disclosed herein will be better understood from the experimental details which follow. However, one skilled in the art will readily appreciate that the specific methods and results discussed are merely illustrative of the inventions as described more fully in the claims which follow thereafter. Unless otherwise indicated, the disclosure is not limited to specific procedures, materials, or the like, as such may vary. It is also to be understood that the terminology used herein is for the purpose of describing particular embodiments only and is not intended to be limiting.

EXAMPLES

Example 1. Control of T-Cell Effector Activity with a Smart-CAR

A Smart Car is made using the third generation anti-CD20 CAR cassette described in Budde 2013 (Budde et al. PLoS1, 2013 doi:10.1371/journal.pone.0082742, which is hereby incorporated-by-reference in its entirety for all purposes), and the RNA control device, 3XL2bulge9 (Win and Smolke 2007 Proc. Natl. Acad. Sci. 104 (36): 14283-88, which is hereby incorporated by reference in its entirety for all purposes). A nucleic acid encoding the 3XL2bulge9 control device is engineered into the anti-CD20 CAR cassette in an appropriate expression vector.

This anti-CD20 Smart CAR is transfected by routine methods into T-cells (Jurkat cells and/or primary human T-cells), and stable populations of T-cells are selected using appropriate antibiotics (or other selection schemes). T-cell populations with anti-CD20 Smart CARs (CD20$^-$/CD22$^-$/CD3$^+$) are activated by co-incubation with anti-CD3/CD28 beads.

Activated anti-CD20 Smart CAR T-cells are co-cultured with CD20$^+$/CD22$^+$/CD3$^-$ Ramos target cells at Smart CAR T-cell:Ramos target ratios of 2:1, 5:1, and 10:1. Ligand for the RNA control device, theophylline is added to the culture medium at concentrations in the range of 500 µM to 1 mM (lower or greater concentrations can be used to titrate Smart-CAR activity to the desired level). The Smart-CAR T-cells and the Ramos cells are grown together for 48 hours. Cultures are washed, and then stained with anti-CD22 and anti-CD3 reagents, followed by counting of CD22$^+$ (Ramos target cells) and CD3$^+$ cells (Smart CAR T-cells). These measurements will identify the target cell killing rate (e.g., half-life) and the proliferation rate of the Smart-CAR T-cells at different levels of Smart-CAR expression.

Example 2. Control of T-Cell Effector Activity with Combination Smart-CARs in a Human Subject Nucleic acids encoding orthogonal Smart CARs that have specificity for distinct TAAs and respond to distinct small molecule ligands are constructed and are packaged into lentiviral vectors. Each of these Smart CARs demonstrate in vitro cytotoxic T-cell effector function and antigen-dependent expansion in response to cognate ligand exposure, and individually have known therapeutic windows in human patients.

To treat a human subject with tumors that express the defined set of multiple TAAs that are recognized by this Smart CAR pool, autologous T-cells are harvested from a patient's peripheral blood by apheresis and transduced ex vivo with lentivirus encoding the cognate Smart CARs, either individually or in pools. Expanded Smart CAR CD4+ and/or CD8+ T-cells are then adoptively transferred back into the patient. Each Smart CAR is individually activated with its own cognate small molecule ligand to initiate tumor recognition and elimination. As each Smart CAR is individually controlled, therapeutic windows for each Smart CAR are adjusted to enforce maximal graft vs. tumor response, with tolerable graft vs. host response. If the escape phase of tumor immunoediting is reached, the Smart CAR targeting the lost TAA is inactivated by removal of its cognate ligand to limit further graft vs. host response for a Smart CAR that no longer provides graft vs. tumor benefits. By controlling Smart CAR toxicity and parallelizing a distributed attack on TAAs quickly, durable remissions for any tumor type are achieved.

Example 3. Control of T-Cell Effector Activity with a DE-CAR

A DE-CAR is made using the anti-CD20 CAR cassette described in Budde 2013 (Budde et al. PLoS1, 2013 doi: 10.1371/journal.pone.0082742, which is hereby incorporated-by-reference in its entirety for all purposes), and the destabilizing element (DE) ecDHFR described in Iwamoto 2010 (Iwamoto et al. Chemistry and Biology, 2010 doi: 10.1016/j.chembiol.2010.07.009, which is hereby incorporated by reference in its entirety for all purposes). In an embodiment, the DE-CAR also encodes the RNA control device, 3XL2bulge9 (Win and Smolke 2007 Proc. Natl Acad. Sci. 104 (36): 14283-88, which is hereby incorporated by reference in its entirety for all purposes). A nucleic acid encoding the DE of mutant scDHFR is engineered into the anti-CD20 CAR cassette in an appropriate expression vector. In an alternate embodiment, a nucleic acid encoding the 3XL2bulge9 control device is further engineered into the DE-anti-CD20 CAR cassette.

This anti-CD20 DE-CAR is transfected by routine methods into T-cells (Jurkat cells and/or primary human T-cells), and stable populations of T-cells are selected using appropriate antibiotics (or other selection schemes). T-cell populations with anti-CD20 DE-CARs or anti-CD20 Smart-DE-CARs (CD20$^-$/CD22$^-$/CD3$^+$) are activated by co-incubation with anti-CD3/CD28 beads.

Activated anti-CD20 DE-CAR T-cells or anti-CD20 Smart-DE-CAR T-cells are co-cultured with CD20$^+$/CD22$^+$/CD3$^-$ Ramos target cells at DE-CAR T-cell (or Smart-DE-CAR T-cell):Ramos target ratios of 2:1, 5:1, and 10:1. Ligand for the DE, trimethoprim, and/or ligand for the RNA control device, theophylline, is added to the culture medium at concentrations in the range of 500 µM to 1 mM (lower or greater concentrations can be used to titrate Smart-CAR activity to the desired level). The DE-CAR T-cells or Smart-DE-CAR T-cells and the Ramos cells are grown together for 48 hours. Cultures are washed, and then stained with anti-CD22 and anti-CD3 reagents, followed by counting of CD22$^+$ (Ramos target cells) and CD3$^+$ cells (DE-CAR and/or Smart-DE-CAR T-cells). These measurements will identify the target cell killing rate (e.g., half-life) and the proliferation rate of the Smart-CAR T-cells at different levels of Smart-CAR expression.

Example 4: Control of T-Cell Effector Activity with Combination DE-CARs and/or Smart-DE-CARs in a Human Subject Nucleic acids encoding orthogonal DE-CARs and/or Smart-DE-CARs that have specificity for distinct TAAs and respond to distinct small molecule ligands are constructed and are packaged into lentiviral vectors. Each of these DE-CARs and/or Smart-DE-CARs demonstrate in vitro cytotoxic T-cell effector function and antigen-dependent expansion in response to cognate ligand exposure, and individually have known therapeutic windows in human patients.

To treat a human subject with tumors that express the defined set of multiple TAAs that are recognized by this DE-CAR and/or Smart-DE-CAR pool, autologous T-cells are harvested from a patient's peripheral blood by apheresis and transduced ex vivo with lentivirus encoding the cognate DE-CARs and/or Smart-DE-CARs, either individually or in pools. Expanded DE-CAR and/or Smart-DE-CAR CD4+ and/or CD8+ T-cells are then adoptively transferred back into the patient. Each DE-CAR and/or Smart-DE-CAR is individually activated with its own cognate small molecule ligand(s) to initiate tumor recognition and elimination. As each DE-CAR and/or Smart-DE-CAR is individually controlled, therapeutic windows for each DE-CAR and/or Smart-DE-CAR are adjusted to enforce maximal graft vs. tumor response, with tolerable graft vs. host response. If the escape phase of tumor immunoediting is reached, the DE-CAR and/or Smart-DE-CAR targeting the lost TAA is inactivated by removal of its cognate ligand to limit further graft vs. host response for a DE-CAR and/or Smart-DE-CAR that no longer provides graft vs. tumor benefits. By controlling DE-CAR and/or Smart-DE-CAR toxicity and parallelizing a distributed attack on TAAs quickly, durable remissions for any tumor type are achieved.

Example 5: Integration of a Nucleic Acid Encoding a DE-CAR and/or Smart-DE-CAR at the CCR5 Locus of a Human T-Lymphocyte The CRISPR system is used to engineer human T-lymphocyte with a nucleic acid encoding a DE-CAR and/or Smart-DE-CAR of the invention downstream from an appropriate control region comprising, e.g., a promoter from SV40, CMV, UBC, EF1A, PGK or CAGG (Qin et al (2010) PLoS ONE. doi:10.1371/journal.pone.0010611, which is incorporated by reference in its entirety for all purposes), optionally a suitable enhancer, e.g., CMV early enhancer, and optionally other suitable regulatory sequences, e.g., woodchuck hepatitis B virus post-transcriptional regulatory element (WPRE; Donello, Loeb, and Hope (1998) Journal of Virology, which is incorporated by reference in its entirety for all purposes) translation initiator at short UTR (TISU; Elfakess et al (2011) NAR 39 (17): 7598-7609. doi:10.1093/nar/gkr484, which is incorporated by reference in its entirety for all purposes), A-U rich elements, beta-globin 3' UTR and poly-A sequence, SV40 3' UTR and poly-A sequence. This expression cassette is flanked on the 3' and 5' sides by appropriate CCR5 sequences for break point(s) associated with synthetic guide sequences obtained using the methodology of, for example, U.S. Pat. No. 8,697,359 (which is incorporated by reference in its entirety for all purposes).

Cas9 is introduced to the T-lymphocyte by electroporation of Cas9 mRNA, sgRNA, and donor nucleic acid encoding the DE-CAR and/or Smart-DE-CAR with appropriate control sequences and CCR5 flanking sequences paired to the sgRNA(s). (See, e.g., Qin et al., Genetics 115:176594 (2015); Qin et al., Genetics 115:176594 (2015), Kim et al (2014) Genome 1012-19, Kim et al. 2014 describe the Amaza Nucleofector, an optimized electroporation system, all three of these references are incorporated by reference in their entirety for all purposes.) Electroporated cells are deposited into multiwell plates and cultured in suitable media.

Representative cells are obtained and assayed by RFLP and/or sequencing to identify T-lymphocytes with DE-CAR and/or Smart-DE-CAR constructs integrated at the CCR5 locus.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of controlling expression of a chimeric antigen receptor, comprising the steps of: transcribing a polynucleotide encoding a chimeric antigen receptor and a RNA control device comprised of a sensor element and a ribozyme element whereby a RNA transcript is made that encodes the RNA control device operably linked to a portion of the transcript encoding the chimeric antigen receptor, wherein a promoter is operably linked to the polynucleotide encoding the RNA control device and the polynucleotide encoding the chimeric antigen receptor, and wherein the chimeric antigen receptor is comprised of an extracellular element, a transmembrane element, and an intracellular element, and wherein the transmembrane element is between the extracellular element and the intracellular element; and exposing the transcript to a ligand for the sensor domain of the RNA control device, wherein ligand binding by the sensor domain changes the activity of the ribozyme whereby the expression of the chimeric antigen receptor is changed.

2. The method of claim 1, wherein the expression of the chimeric antigen receptor is increased.

3. The method of claim 1, wherein the expression of the chimeric antigen receptor is decreased.

4. The method of claim 1, wherein the polynucleotide encoding the chimeric antigen receptor further comprises a polynucleotide encoding a costimulatory element, wherein the transmembrane element is between the extracellular element and the costimulatory element.

5. The method of claim 4, wherein the costimulatory element is in a domain with the intracellular element.

6. The method of claim 4, wherein the costimulatory element is in a domain separate from the intracellular element.

7. The method of claim 1, further comprising a polynucleotide encoding a hinge element, wherein the hinge element is associated with the transmembrane element or the extracellular element.

8. The method of claim 1, wherein the polynucleotide further comprises a second RNA control device comprised of a sensor element and a ribozyme element wherein the RNA control device is operably linked to the polynucleotide encoding the chimeric antigen receptor.

9. The method of claim 8, wherein the first sensor element binds to a first ligand and the second sensor element binds to a second ligand, wherein the first ligand and the second ligand are different.

10. The method of claim 9, further comprising the step of exposing the transcript to the second ligand for the sensor domain of the second RNA control device, wherein ligand binding by the sensor domain for the second RNA control device changes the activity of the ribozyme of the second RNA control device whereby the expression of the chimeric antigen receptor is changed.

11. The method of claim 10, wherein at least some of the time the transcript is exposed to the ligand for the first sensor element of the first RNA control device without ligand for the second sensor element of the second RNA control device.

12. The method of claim 10, wherein the second RNA control device decreases ribozyme activity upon binding of the second ligand.

13. The method of claim 10, wherein the second RNA control device increases ribozyme activity upon binding of the second ligand.

14. The method of claim 1, wherein the transcription of the polynucleotide occurs in a hematopoietic cell.

15. The method of claim 14, wherein the hematopoietic cell is a T-lymphocyte.

16. The method of claim 14, wherein the hematopoietic cell is a natural killer cell.

17. The method of claim 14, wherein the ligand is secreted by a target cell and wherein the extracellular domain of the chimeric antigen receptor binds a molecule found on the target cell.

18. The method of claim 17, wherein the polynucleotide further comprises a second RNA control device comprised of a sensor element and a ribozyme element wherein the second ribozyme element is operably linked to the polynucleotide encoding the chimeric antigen receptor.

19. The method of claim 18, wherein the first sensor element binds to a first ligand and the second sensor element binds to a second ligand, wherein the first ligand and the second ligand are different.

20. The method of claim 19, further comprising the step of exposing the eukaryotic cell to the second ligand for the sensor domain of the second RNA control device, wherein ligand binding by the sensor domain for the second RNA control device changes the activity of the ribozyme of the second RNA control device whereby the expression of the chimeric antigen receptor is changed.

* * * * *